(12) United States Patent
DeFrees et al.

(10) Patent No.: US 8,791,070 B2
(45) Date of Patent: *Jul. 29, 2014

(54) GLYCOPEGYLATED FACTOR IX

(71) Applicant: Novo Nordisk A/S, Bagsvaerd (DK)

(72) Inventors: Shawn DeFrees, North Wales, PA (US);
Robert J. Bayer, San Diego, CA (US);
Caryn Bowe, Doylestown, PA (US);
Krishnasamy Paneerselvam, Poway, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,442

(22) Filed: Oct. 11, 2013

(65) Prior Publication Data

US 2014/0112903 A1 Apr. 24, 2014

Related U.S. Application Data

(63) Continuation of application No. 13/897,529, filed on May 20, 2013, now abandoned, which is a continuation of application No. 13/837,850, filed on Mar. 15, 2013, now abandoned, which is a continuation-in-part of application No. 11/915,239, filed as application No. PCT/US2006/020230 on Mar. 25, 2006, now abandoned, said application No. 13/837,850 is a continuation-in-part of application No. 11/867,553, filed on Oct. 4, 2007, and a continuation-in-part of application No. 13/246,512, filed on Sep. 27, 2011, which is a continuation of application No. 12/496,595, filed on Jul. 1, 2009, now Pat. No. 8,063,015, which is a continuation of application No. 10/552,896, filed as application No. PCT/US2004/011494 on Apr. 9, 2004, now abandoned, which is a continuation of application No. 10/411,012, filed on Apr. 9, 2003, now Pat. No. 7,265,084, and a continuation of application No. 10/411,026, filed on Apr. 9, 2003, now Pat. No. 7,795,210, and a continuation of application No. 10/410,962, filed on Apr. 9, 2003, now Pat. No. 7,173,003, and a continuation of application No. 10/411,049, filed on Apr. 9, 2003, now Pat. No. 7,297,511, and a continuation of application No. 10/410,930, filed on Apr. 9, 2003, now Pat. No. 7,226,903, and a continuation of application No. 10/410,897, filed on Apr. 9, 2003, now Pat. No. 7,179,617, and a continuation of application No. 10/410,997, filed on Apr. 9, 2003, now Pat. No. 7,157,277, and a continuation of application No. 10/411,044, filed on Apr. 9, 2003, now Pat. No. 8,008,252, and a continuation of application No. 10/410,980, filed on Apr. 9, 2003, now Pat. No. 7,399,613, and a continuation of application No. 10/410,945, filed on Apr. 9, 2003, now Pat. No. 7,214,660, and a continuation of application No. 10/410,913, filed on Apr. 9, 2003, now Pat. No. 7,265,085, and a continuation of application No. 10/411,037, filed on Apr. 9, 2003, now Pat. No. 7,125,843, and a continuation of application No. 10/411,043, filed on Apr. 9, 2003, now Pat. No. 7,439,043.

(60) Provisional application No. 60/684,729, filed on May 25, 2005, provisional application No. 60/707,994, filed on Aug. 12, 2005, provisional application No. 60/710,535, filed on Aug. 23, 2005, provisional application No. 60/828,208, filed on Oct. 4, 2006.

(51) Int. Cl.
*A61K 38/00* (2006.01)
*A61P 7/00* (2006.01)
*C12N 9/64* (2006.01)

(52) U.S. Cl.
CPC ..................................... *C12N 9/644* (2013.01)
USPC ........................................................ 514/13.5

(58) Field of Classification Search
CPC .... C07K 14/505; A61K 38/00; C12P 21/005; C12P 21/02; C12N 9/6437; C12N 9/22; C07H 19/00; C23C 18/1601; H05K 2203/072; H05K 2203/073; H05K 3/244
See application file for complete search history.

(56) References Cited

U.S. PATENT DOCUMENTS

| | | | |
|---|---|---|---|
| 4,055,635 A | 10/1977 | Green et al. | |
| 4,088,538 A | 5/1978 | Schneider | |
| 4,179,337 A | 12/1979 | Davis et al. | |
| 4,385,260 A | 5/1983 | Watts | |

(Continued)

FOREIGN PATENT DOCUMENTS

| | | |
|---|---|---|
| CA | 2397347 A1 | 8/2001 |
| CA | 2500389 A1 | 4/2004 |

(Continued)

OTHER PUBLICATIONS

U.S. Appl. No. 10/360,779, DeFress.

(Continued)

*Primary Examiner* — Thomas Heard
(74) *Attorney, Agent, or Firm* — Michael J. Brignati

(57) ABSTRACT

Conjugates between Factor IX and PEG moieties. are disclosed in the present application. The conjugates are linked via a glycosyl linking group interposed between and covalently attached to the peptide and the modifying group. Conjugates are formed from glycosylated peptides by the action of a glycosyltransferase. The glycosyltransferase ligates a modified sugar moiety onto a glycosyl residue on the peptide. Also provided are methods for preparing the conjugates, methods for treating various disease conditions with the conjugates, and pharmaceutical formulations including the conjugates.

20 Claims, 29 Drawing Sheets

(56) References Cited

U.S. PATENT DOCUMENTS

| | | | |
|---|---|---|---|
| 4,412,989 | A | 11/1983 | Iwashita et al. |
| 4,414,147 | A | 11/1983 | Klibanov et al. |
| 4,438,253 | A | 3/1984 | Casey et al. |
| 4,496,689 | A | 1/1985 | Mitra |
| 4,565,653 | A | 1/1986 | Ives et al. |
| 4,806,595 | A | 2/1989 | Noishiki et al. |
| 4,826,945 | A | 5/1989 | Cohn et al. |
| 4,847,325 | A | 7/1989 | Shadle et al. |
| 4,879,236 | A | 11/1989 | Smith et al. |
| 4,904,584 | A | 2/1990 | Shaw |
| 4,925,796 | A | 5/1990 | Bergh et al. |
| 4,980,502 | A | 12/1990 | Felder et al. |
| 5,032,519 | A | 7/1991 | Paulson et al. |
| 5,047,335 | A | 9/1991 | Paulson et al. |
| 5,104,651 | A | 4/1992 | Boone et al. |
| 5,122,614 | A | 6/1992 | Zalipsky |
| 5,147,788 | A | 9/1992 | Page et al. |
| 5,153,265 | A | 10/1992 | Shadle et al. |
| 5,154,924 | A | 10/1992 | Friden |
| 5,166,322 | A | 11/1992 | Shaw et al. |
| 5,169,933 | A | 12/1992 | Anderson et al. |
| 5,182,107 | A | 1/1993 | Friden |
| 5,194,376 | A | 3/1993 | Kang |
| 5,202,413 | A | 4/1993 | Spinu |
| 5,206,344 | A | 4/1993 | Katre et al. |
| 5,219,564 | A | 6/1993 | Zalipsky et al. |
| 5,281,698 | A | 1/1994 | Nitecki |
| 5,324,663 | A | 6/1994 | Lowe |
| 5,324,844 | A | 6/1994 | Zalipsky |
| 5,342,940 | A | 8/1994 | Ono et al. |
| 5,346,696 | A | 9/1994 | Kim et al. |
| 5,352,670 | A | 10/1994 | Venot et al. |
| 5,369,017 | A | 11/1994 | Wong et al. |
| 5,374,541 | A | 12/1994 | Wong et al. |
| 5,374,655 | A | 12/1994 | Kashem et al. |
| 5,399,345 | A | 3/1995 | Schumacher et al. |
| 5,405,753 | A | 4/1995 | Brossmer et al. |
| 5,410,016 | A | 4/1995 | Hubbell et al. |
| 5,432,059 | A | 7/1995 | Bean et al. |
| 5,446,090 | A | 8/1995 | Harris |
| 5,492,821 | A | 2/1996 | Callstrom et al. |
| 5,492,841 | A | 2/1996 | Craig |
| 5,527,527 | A | 6/1996 | Friden |
| 5,529,914 | A | 6/1996 | Hubbell et al. |
| 5,545,553 | A | 8/1996 | Gotschlich |
| 5,580,560 | A | 12/1996 | Nicolaisen et al. |
| 5,583,042 | A | 12/1996 | Roth |
| 5,605,793 | A | 2/1997 | Stemmer |
| 5,614,184 | A | 3/1997 | Sytkowski et al. |
| 5,621,039 | A | 4/1997 | Hallahan et al. |
| 5,629,384 | A | 5/1997 | Veronese et al. |
| 5,635,603 | A | 6/1997 | Hansen et al. |
| 5,643,575 | A | 7/1997 | Martinez et al. |
| 5,646,113 | A | 7/1997 | Attie et al. |
| 5,672,662 | A | 9/1997 | Harris et al. |
| 5,672,683 | A | 9/1997 | Friden et al. |
| 5,705,367 | A | 1/1998 | Gotschlich |
| 5,716,812 | A | 2/1998 | Withers et al. |
| 5,723,121 | A | 3/1998 | Takenaga et al. |
| 5,728,554 | A | 3/1998 | Bayer et al. |
| 5,739,208 | A | 4/1998 | Harris |
| 5,762,920 | A | 6/1998 | Yung et al. |
| 5,770,420 | A | 6/1998 | Lowe et al. |
| 5,798,233 | A | 8/1998 | Gotschlich |
| 5,811,238 | A | 9/1998 | Stemmer et al. |
| 5,824,639 | A | 10/1998 | Berkner |
| 5,824,778 | A | 10/1998 | Ishikawa et al. |
| 5,824,864 | A | 10/1998 | Fox et al. |
| 5,830,721 | A | 11/1998 | Stemmer et al. |
| 5,833,988 | A | 11/1998 | Friden |
| 5,834,251 | A | 11/1998 | Maras et al. |
| 5,837,458 | A | 11/1998 | Minshull et al. |
| 5,849,535 | A | 12/1998 | Cunningham et al. |
| 5,858,751 | A | 1/1999 | Paulson et al. |
| 5,858,752 | A | 1/1999 | Seed et al. |
| 5,861,374 | A | 1/1999 | Berkner et al. |
| 5,874,075 | A | 2/1999 | Collins et al. |
| 5,876,980 | A | 3/1999 | DeFrees et al. |
| 5,922,577 | A | 7/1999 | Defrees et al. |
| 5,932,462 | A | 8/1999 | Harris et al. |
| 5,939,290 | A | 8/1999 | Venot et al. |
| 5,945,314 | A | 8/1999 | Prieto et al. |
| 5,945,322 | A | 8/1999 | Gotschlich |
| 5,955,347 | A | 9/1999 | Lowe |
| 5,962,294 | A | 10/1999 | Paulson et al. |
| 5,969,040 | A | 10/1999 | Hallahan et al. |
| 5,977,307 | A | 11/1999 | Friden et al. |
| 5,997,864 | A | 12/1999 | Hart et al. |
| 6,010,999 | A | 1/2000 | Daley et al. |
| 6,015,555 | A | 1/2000 | Friden |
| 6,030,815 | A | 2/2000 | DeFrees et al. |
| 6,034,223 | A | 3/2000 | Maddon et al. |
| 6,037,452 | A | 3/2000 | Minamino et al. |
| 6,048,720 | A | 4/2000 | Dalborg et al. |
| 6,057,292 | A | 5/2000 | Cunningham et al. |
| 6,075,134 | A | 6/2000 | Bertozzi et al. |
| 6,087,325 | A | 7/2000 | Meers et al. |
| 6,096,512 | A | 8/2000 | Elhammer et al. |
| 6,113,906 | A | 9/2000 | Greenwald et al. |
| 6,117,651 | A | 9/2000 | Schultz et al. |
| 6,127,153 | A | 10/2000 | Johnson et al. |
| 6,156,547 | A | 12/2000 | Roth |
| 6,166,183 | A | 12/2000 | Ishikawa et al. |
| 6,183,738 | B1 | 2/2001 | Clark |
| 6,188,738 | B1 | 2/2001 | Sakamoto et al. |
| 6,251,864 | B1 | 6/2001 | Dower et al. |
| 6,261,805 | B1 | 7/2001 | Wood |
| 6,268,193 | B1 | 7/2001 | Lowe |
| 6,319,695 | B1 | 11/2001 | Wong et al. |
| 6,342,382 | B1 | 1/2002 | Gotschlich |
| 6,348,558 | B1 | 2/2002 | Harris et al. |
| 6,362,254 | B2 | 3/2002 | Harris et al. |
| 6,376,604 | B2 | 4/2002 | Kozlowski |
| 6,379,933 | B1 | 4/2002 | Johnson et al. |
| 6,399,336 | B1 | 6/2002 | Paulson et al. |
| 6,399,337 | B1 | 6/2002 | Taylor et al. |
| 6,440,703 | B1 | 8/2002 | DeFrees |
| 6,458,937 | B1 | 10/2002 | Bertozzi et al. |
| 6,465,220 | B1 | 10/2002 | Hassan et al. |
| 6,495,365 | B1 | 12/2002 | Saito et al. |
| 6,531,121 | B2 | 3/2003 | Brines et al. |
| 6,555,346 | B1 | 4/2003 | Kretzdorn et al. |
| 6,555,660 | B2 | 4/2003 | Nissen et al. |
| 6,586,398 | B1 | 7/2003 | Kinstler et al. |
| 6,692,931 | B1 | 2/2004 | Reutter et al. |
| 6,693,183 | B2 | 2/2004 | Natsuka et al. |
| 6,716,626 | B1 | 4/2004 | Itoh et al. |
| 6,743,896 | B2 | 6/2004 | Filpula et al. |
| 6,780,624 | B2 | 8/2004 | Gotschlich |
| 6,800,740 | B1 | 10/2004 | Cunningham et al. |
| 6,949,372 | B2 | 9/2005 | Betenbaugh et al. |
| 7,094,530 | B1 | 8/2006 | Sasaki et al. |
| 7,125,843 | B2 | 10/2006 | DeFrees et al. |
| 7,138,371 | B2 | 11/2006 | DeFrees et al. |
| 7,157,277 | B2 | 1/2007 | DeFrees et al. |
| 7,173,003 | B2 | 2/2007 | DeFrees et al. |
| 7,179,617 | B2 | 2/2007 | DeFrees et al. |
| 7,199,223 | B2 | 4/2007 | Bossard et al. |
| 7,202,208 | B2 | 4/2007 | Papadimitriou |
| 7,214,660 | B2 | 5/2007 | DeFrees et al. |
| 7,226,903 | B2 | 6/2007 | DeFrees et al. |
| 7,229,962 | B2 | 6/2007 | Chung et al. |
| 7,235,638 | B2 | 6/2007 | Persson |
| 7,265,084 | B2 | 9/2007 | DeFrees et al. |
| 7,265,085 | B2 | 9/2007 | DeFrees et al. |
| 7,276,475 | B2 | 10/2007 | DeFrees et al. |
| 7,297,511 | B2 | 11/2007 | DeFrees et al. |
| 7,304,150 | B1 | 12/2007 | Egrie et al. |
| 7,338,933 | B2 | 3/2008 | DeFrees et al. |
| 7,368,108 | B2 | 5/2008 | DeFrees et al. |
| 7,399,613 | B2 | 7/2008 | DeFrees et al. |
| 7,405,198 | B2 | 7/2008 | DeFrees et al. |
| 7,416,858 | B2 | 8/2008 | DeFrees et al. |
| 7,439,043 | B2 | 10/2008 | DeFrees et al. |

(56) References Cited

U.S. PATENT DOCUMENTS

| | | |
|---|---|---|
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,008,252 B2 | 8/2011 | DeFrees et al. |
| 8,063,015 B2 | 11/2011 | DeFrees et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0115833 A1 | 8/2002 | Burg et al. |
| 2002/0137134 A1 | 9/2002 | Gerngross |
| 2002/0142370 A1 | 10/2002 | Paulson et al. |
| 2002/0148791 A1 | 10/2002 | DeFrees |
| 2002/0150981 A1 | 10/2002 | Canfield |
| 2002/0168323 A1 | 11/2002 | Gonda |
| 2002/0182586 A1 | 12/2002 | Morris et al. |
| 2003/0003529 A1 | 1/2003 | Bayer |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186580 A1 | 10/2003 | Dambach et al. |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0043446 A1 | 3/2004 | DeFrees et al. |
| 2004/0043464 A1 | 3/2004 | Gotschlich |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0032742 A1 | 2/2005 | DeFrees et al. |
| 2005/0058620 A1 | 3/2005 | Nakamoto et al. |
| 2005/0064540 A1 | 3/2005 | Defrees et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0177892 A1 | 8/2006 | De Frees |
| 2006/0182714 A1 | 8/2006 | Behrens et al. |
| 2006/0198819 A1 | 9/2006 | Behrens et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees |
| 2007/0037966 A1 | 2/2007 | Rasmussen et al. |
| 2007/0037996 A1 | 2/2007 | Hogg et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | Defrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | Defrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | Defrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | Defrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174059 A1 | 7/2010 | DeFrees et al. |

(56) References Cited

U.S. PATENT DOCUMENTS

| | | |
|---|---|---|
| 2010/0210507 A9 | 8/2010 | DeFrees et al. |
| 2010/0261872 A1 | 10/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0064719 A1 | 3/2011 | Rasmussen et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |

FOREIGN PATENT DOCUMENTS

| | | |
|---|---|---|
| CA | 2511814 A1 | 7/2004 |
| DE | 19852729 A1 | 5/2000 |
| EP | 154316 A2 | 9/1985 |
| EP | 200421 A2 | 11/1986 |
| EP | 0370205 A2 | 5/1990 |
| EP | 0459630 A2 | 12/1991 |
| EP | 474313 A2 | 3/1992 |
| EP | 585109 A2 | 3/1994 |
| EP | 605963 A2 | 7/1994 |
| EP | 1260582 A1 | 11/2002 |
| EP | 1270642 A1 | 1/2003 |
| EP | 1428878 A1 | 6/2004 |
| JP | 59-172425 A | 9/1984 |
| JP | 03-503759 T | 8/1991 |
| JP | 6-504678 T | 6/1994 |
| JP | 9503905 T | 4/1997 |
| JP | 10-307356 A | 11/1998 |
| JP | 2001061479 A | 3/2001 |
| JP | 2001-508783 T | 7/2001 |
| JP | 2001-519784 | 10/2001 |
| JP | 2003-521930 T | 7/2003 |
| WO | 87/00056 | 1/1987 |
| WO | 87/00056 A1 | 1/1987 |
| WO | 87/05330 | 9/1987 |
| WO | 87/05330 A1 | 9/1987 |
| WO | 88/10295 A1 | 12/1988 |
| WO | 89/06546 | 7/1989 |
| WO | 89/10134 | 11/1989 |
| WO | 90/07572 | 7/1990 |
| WO | 90/08164 | 7/1990 |
| WO | 90/08823 | 8/1990 |
| WO | 90/13540 A1 | 11/1990 |
| WO | 91/11514 A1 | 8/1991 |
| WO | 91/14697 | 10/1991 |
| WO | 92/01055 A1 | 1/1992 |
| WO | 92/15686 | 9/1992 |
| WO | 92/16555 | 10/1992 |
| WO | 92/22310 A1 | 12/1992 |
| WO | 92/18135 | 3/1993 |
| WO | 93/15189 A1 | 8/1993 |
| WO | 94/04193 A1 | 3/1994 |
| WO | 94/05332 | 3/1994 |
| WO | 94/05332 A2 | 3/1994 |
| WO | 94/09027 A1 | 4/1994 |
| WO | 94/15625 | 7/1994 |
| WO | 94/17039 A1 | 8/1994 |
| WO | 94/18247 A1 | 8/1994 |
| WO | 94/27631 | 12/1994 |
| WO | 94/28024 A1 | 12/1994 |
| WO | 95/02421 | 1/1995 |
| WO | 95/04278 A1 | 2/1995 |
| WO | 96/10089 | 4/1996 |
| WO | 96/11953 A1 | 4/1996 |
| WO | 96/12800 | 5/1996 |
| WO | 96/40731 | 6/1996 |
| WO | 96/21468 A2 | 7/1996 |
| WO | 96/21469 | 7/1996 |
| WO | 96/21469 A1 | 7/1996 |
| WO | 96/32491 | 10/1996 |
| WO | 96/36357 A1 | 11/1996 |
| WO | 96/40881 A1 | 12/1996 |
| WO | 97/05330 | 2/1997 |
| WO | 97/47651 | 12/1997 |
| WO | 98/05363 | 2/1998 |
| WO | 98/31826 | 7/1998 |
| WO | 98/31826 A1 | 7/1998 |
| WO | 98/32466 | 7/1998 |
| WO | 98/41562 A1 | 9/1998 |
| WO | 98/51784 | 11/1998 |
| WO | 98/58964 | 12/1998 |
| WO | 98/58964 A1 | 12/1998 |
| WO | 99/00150 | 1/1999 |
| WO | 99/03887 | 1/1999 |
| WO | 99/13063 | 3/1999 |
| WO | 99/14259 A1 | 3/1999 |
| WO | 99/22764 | 5/1999 |
| WO | 99/22764 A1 | 5/1999 |
| WO | 99/34833 A1 | 7/1999 |
| WO | 99/45964 | 9/1999 |
| WO | 99/48515 A1 | 9/1999 |
| WO | 99/54342 | 10/1999 |
| WO | 99/54342 A1 | 10/1999 |
| WO | 99/55376 A1 | 11/1999 |
| WO | 00/23114 A2 | 4/2000 |
| WO | 00/26354 A1 | 5/2000 |
| WO | 00/29558 A1 | 5/2000 |
| WO | 00/29603 A2 | 5/2000 |
| WO | 00/65087 A1 | 11/2000 |
| WO | 01/02017 A2 | 1/2001 |
| WO | 01/05434 A2 | 1/2001 |
| WO | 01/39788 A2 | 6/2001 |
| WO | 01/49830 A2 | 7/2001 |
| WO | 01/51510 A2 | 7/2001 |
| WO | 01/58493 A1 | 8/2001 |
| WO | 01/58935 A2 | 8/2001 |
| WO | 01/60411 A1 | 8/2001 |
| WO | 01/68565 A2 | 9/2001 |
| WO | 01/76640 A2 | 10/2001 |
| WO | 01/83725 A1 | 11/2001 |
| WO | 01/88117 A2 | 11/2001 |
| WO | 02/02597 A2 | 1/2002 |
| WO | 02/02764 A2 | 1/2002 |
| WO | 02/03075 A2 | 1/2002 |
| WO | 02/13843 A2 | 2/2002 |
| WO | 02/13873 A2 | 2/2002 |
| WO | 02/29025 A2 | 4/2002 |
| WO | 02/44196 A1 | 6/2002 |
| WO | 02/053580 A2 | 7/2002 |
| WO | 02/074806 A2 | 9/2002 |
| WO | 02/077218 | 10/2002 |
| WO | 02/077218 A1 | 10/2002 |
| WO | 02/092619 A2 | 11/2002 |
| WO | 03/017949 A2 | 3/2003 |
| WO | 03/027147 A2 | 4/2003 |
| WO | 03/031464 A2 | 4/2003 |
| WO | 03/037932 A2 | 5/2003 |
| WO | 03/045980 A2 | 6/2003 |
| WO | 03/046150 | 6/2003 |
| WO | 03/093448 | 11/2003 |
| WO | 04/000366 A1 | 12/2003 |
| WO | 2004/009838 | 1/2004 |
| WO | 2004/010327 A2 | 1/2004 |
| WO | 2004/022004 | 3/2004 |
| WO | 2004/029091 A2 | 4/2004 |
| WO | 2004/033651 A2 | 4/2004 |
| WO | 2004/046222 | 6/2004 |
| WO | 2004/067566 A1 | 8/2004 |
| WO | 2004/083258 | 9/2004 |
| WO | 2004/083258 A2 | 9/2004 |
| WO | 2004/083259 | 9/2004 |
| WO | 2004/091499 | 10/2004 |
| WO | 2004/091499 A2 | 10/2004 |
| WO | 2004/093823 A2 | 11/2004 |
| WO | 2004/096148 A2 | 11/2004 |
| WO | 2004/099231 A2 | 11/2004 |
| WO | 2004/103275 A2 | 12/2004 |
| WO | 2005/012484 | 2/2005 |

(56) References Cited

FOREIGN PATENT DOCUMENTS

| | | |
|---|---|---|
| WO | 2005/025606 A1 | 3/2005 |
| WO | 2005/051327 | 6/2005 |
| WO | 2005/051327 A2 | 6/2005 |
| WO | 2005/055946 | 6/2005 |
| WO | 2005/055946 A2 | 6/2005 |
| WO | 2005/055950 | 6/2005 |
| WO | 2005/055950 A2 | 6/2005 |
| WO | 2005/056760 | 6/2005 |
| WO | 2005/067601 A2 | 7/2005 |
| WO | 2005/070138 A2 | 8/2005 |
| WO | 2005/072371 | 8/2005 |
| WO | 2005/079363 A2 | 9/2005 |
| WO | 2005/091944 | 10/2005 |
| WO | 2005/121331 A2 | 12/2005 |
| WO | 2006/010143 | 1/2006 |
| WO | 2006/014349 A2 | 2/2006 |
| WO | 2006/014466 A2 | 2/2006 |
| WO | 2006/020372 | 2/2006 |
| WO | 2006/031811 A2 | 3/2006 |
| WO | 2006/050247 | 5/2006 |
| WO | 2006/074279 A1 | 7/2006 |
| WO | 2006/074467 | 7/2006 |
| WO | 2006/078645 A2 | 7/2006 |
| WO | 2006/105426 | 10/2006 |
| WO | 2006/119987 A2 | 11/2006 |
| WO | 2006/121569 | 11/2006 |
| WO | 2006/127910 | 11/2006 |
| WO | 2007/022512 | 2/2007 |
| WO | 2007/056191 | 5/2007 |
| WO | 2008/011633 A2 | 1/2008 |
| WO | 2008/057683 | 5/2008 |
| WO | 2008/060780 | 5/2008 |
| WO | 2008/073620 | 6/2008 |
| WO | 2008/116633 A1 | 10/2008 |
| WO | 2008/124406 | 10/2008 |
| WO | 2008/151258 | 12/2008 |
| WO | 2008/154639 | 12/2008 |
| WO | 2009/089396 | 7/2009 |

OTHER PUBLICATIONS

U.S. Appl. No. 10/360,770, DeFrees.
U.S. Appl. No. 60/387,292, Shawn DeFrees.
U.S. Appl. No. 60/328,523, Shawn DeFrees.
Neose Technologies, Inc's 10-K Annual Report to the SEC for . . . , "Neose Technologies. Inc's 10-K Annual Report to the SEC for the Year Ending Dec. 31, 2003".
Neose Technologies, Inc's 2002 Annual Report.
Neose Technologies, Inc's 2003 Annual Report.
Neose Technologies, Inc's Investor Presentation (Jul. 2004).
Neose Technologies, Inc's presentation at the U.S. Bancorp Piper, "Neose Technologies, Inc's Presentation at the U.S. Bancorp Piper Jaffray Health Care Conference" (Jan. 30, 2003).
Neose Technologies, Inc's press release dated Oct. 1, 2002.
Neose Technologies, Inc's press release dated May 13, 2005.
Neose Technologies, Inc's press release dated Nov. 17, 2003.
Neose Technologies, Inc's press release dated Jun. 28, 2006.
Neose Technologies, Inc's press release dated Oct. 29, 2002.
Response of the Applicant to Examining Division of Apr. 19, 2010.
Response of the Applicant to Examining Division of Sep. 28, 2010.
De Graaf et al., Journal of Experimental Medicine, "Inflammation-Induced Expression of Sialyl Lewis X-Containing Glycan Structures on Alpha1-Acid Glycoprotein (Orosomucoid) in Human Sera", 1993, vol. 177, pp. 657-666.
Hedner, U. et al, Journal of Clinical Investigation, "Use of Human Factor VIIA in the Treatment of Two Hemophilia A Patients With High-Titer Inhibitors", 1983, vol. 71, No. 6, pp. 1836-1841.
Hedner et al., "Clinical Experience with Human Plasma-Derived Facotr VIIA in Patients with Hemophilia A and High Titer Inhibitors." Haemostasis, 1989, vol. 19, pp. 335-343.
Johansen et al., "Prolonged effect of GlycoPEGylated rFVIIa (40I-PEG-rFVIIa) in Rabbits Correlates to Activity in Plasma." Thrombosis and Haemostasis, 2010, vol. 104, pp. 157-164.
Klausen et at, Molecular Biotechnology, "Analysis of the Site-Specific Asparagine-Linked Glycosylation of Recombinant Human Coagulation Factor VIIA by Glycosidase Digestions, Liquid Chromatography, and Mass Spectrometry", 1998, vol. 9, pp. 195-204.
Ludlam, "The Evidence Behind Inhibitor Treatment with Recombinant Factor VIIa" Pathophysiology of Haemostasis and Thrombosis, 2002, vol. 32, No. Suppl1, pp. 13-18.
Roberts, M.J et al., Advanced Drug Delivery Reviews, "Chemistry for Peptide and Protein Pegylation", 2002, vol. 54, No. -, pp. 459-476.
Veronese et al., Il Farmaco, "Bioconjugation in Pharmaceutical Chemistry Bioconjugation in Pharmaceutical Chemistry", 1999, vol. 54, No. 8, pp. 497-516.
Rathnam et al. "Conjugation of a Fetuin Glycopeptide to Human Follicile-Stimulating Hormoneand It's Subunits by Photoactivation", Biochemica Et Biophysica Acta, vol. 624, No. 2, pp. 436-442 (1980).
Guo et al."Utilization of Glycosyltransferases to Change Oligosaccharide Structures," Appl. Biochem and Biotech, vol. 68, No. 1/02, pp. 1-20 (1997).
Srivastava et al., "Enzymatic Transfer of a Preassembled Trisaccharide Antigen to Cell Surfaces Using a Fucosyltransferase." J of Biol Chem, vol. 267, No. 31, pp. 22356-22361 (1992).
Schwarz et al., "Transfer of 131i and Fluoresceinyl Sialic Acid Derivatives Into the Oligosaccharide Chains of IgG: A New Method for Site-Specific Labeling of Antibodies," Nuclear Medicine and Biology, vol. 26, pp. 383-388 (1999).
Hallgren et al., "An Animated GDP-Fucose Analog Useful in the Fucosyltransferase Catalyzed Addition of Biological Probes Onto Oligosaccharide Chains," J. Carbo Chem. vol. 14, No. 4-5, pp. 453-464 (1995).
Gross et al., "Enzymatic Introduction of a Fluorescent Sialic Acid Into Oligosaccharide Chains of Glycoproteins," Eur. J. Biochem., vol. 177, No. 3, pp. 583-589 (1988).
Ghose et al., "Cytotoxicity Tests and Cytotoxic Agents," Methods in Enzymology, Academic Press Inc., Sna Diego, CA., vol. 93, 1983, pp. 280-333.
Broxmeyer et al., "Rapid Mobilization of Murine and Human Hematopoietic Stem and Progenitor Cells with AMD3100, a CXCR4 Antagonist." Journal Experimental Medicine, vol. 201, No. 8, pp. 1307-1318 (2005).
Brumeanu et al., "Enzymatically Mediated, Glycosidic Conjugation of Immunoglobulins With Viral Epitopes", Journal of Immunological Methods, vol. 183, pp. 185-197 (1995).
Krystal et al., "Purification of Human Erythroprotein to Homogeneity by a Rapid Five-Step Procedure," Blood, vol. 67, No. 1, pp. 71-79 (1986).
Quelle et al., "High-Level Expression and Purification of a Recombinant Human Erythroprotein Produced Using a Baculovirus Vector," Blood, vol. 74, No. 2, pp. 652-657 (1989).
Tom et al., "Reproducible Production of a Pegylated Dual-Acting Peptide for Diabetes," AASP Journal, vol. 9, No. 2, pp. E227-E234 (2007).
Yin et al., "Effects of Antioxidants on the Hydrogen Peroxide-Mediated Oxidation of Methionine Residues in Granulocyte Colony-Stimulating Factor and Human Parathyroid Hormone Fragment 13-34", Pharmaceutical Research, vol. 21, No. 12, pp. 2377-2383 (2004).
GE Healthcare, "Ion Exchange Chromatography & Chromatofcusing: Principles and Methods," Edition AA, Amersham Biosciences, pp. 7, 11-12, 16-17, 21-23, 26-36, 41, 89, 156, 160, 161 (2004).
Kennedy, "Hydrophobic-Interaction Chromatography," in Current Protocols in Protein Science, pp. 8.4.1-8.4.21, Wiley (1995).
O'Shannessy et al., "Specific Conjugation Reactions of the Oligosaccharide Moieties of Immunoglobulins." J. Appl. Biochem., vol. 7, pp. 347-355 (1985).
Uptima, Detergenst: Solubilization of Biomolecules, Internet Page From www.interchim.com/interchim/bio/produits_uptima/product_line/p1p_detergents.htm, 2001, printed Jun. 11, 2012.
NCBI—Accession No. NP_999299 (2 pgs.).
NCBI Accession No. NCAA26095 (2 pgs.).
NCBI—Accession No. NP_058697 (3 pgs.).
NCBI Database, "NCBI Database Hits for Erythropoietin Protein Sequences", 3 pgs.

(56) References Cited

OTHER PUBLICATIONS

Ethylene Glycol Chemistry:Biotechnical & Biomedical Applications, Poly, 1992.
Machine Translation of Japanese Patent 2001-508783, 2001.
Machine Translation of Japanese Patent 2003-521930, 2003.
PEG Glucocerebrosidase, Internet Page From www.gaucher.org.uk/peg2.prg, 2002.
http://dictionary.reference.com/browse/moiety, "Definition of Moiety From http://dictionary.reference.com/browse/moiety", 2010.
DeFrees et al., Glycobiology, "Glycopegylation of Recombinant Therapeutic Proteins Produced in *Escherichia coli*", 2006, vol. 16, No. 9, pp. 833-843.
Harris et al., Biochemistry, "Identification and Structural Analysis of the Tetrasaccharide NeuAc.Alpha.(2.FwdArw.6)Gal.Beta.(1.FwdArw.4)GlcNAc.Beta.(1.FwdArw.3)Fuc.Alpha.1.FwdArw.O-Linked to Serine 61 of Human Factor IX", 1993, vol. 32, No. 26, pp. 6539-6547.
Harris et al., Nature Reviews. Drug Discovery., "Effects of Pegylation on Pharmaceuticals", 2003, vol. 2, pp. 214-221.
Shapiro et al., Blood, "The Safety and Efficacy of Recombinant Human Blood Coagulation Factor IX in Previously Untreated Patients With Severe or Moderately Severe Hemophilia B", 2005, vol. 105, No. 2, pp. 518-525.
Yoshitake, Biochemistry, "Nucleotide Sequence of the Gene for Human Factor IX", 1985, vol. 24, pp. 3736-3750.
Definition of Moiety From http://dictionary.reference.com/browse/moiety, p. 1-3, Accessed Aug. 26, 2010.
Harris et al., "Identification and Structural Analysis of the Tetrasaccharide NeuAc alpha(2 forward arrow 6)Gal beta(1 forward arrow 4)GlcNAc beta(1 forward arrow 3)Fuc alpha1 forward arrow O-Linked to Serine 61 of Human Factor IX", Biochemistry, 1993, vol. 32, pp. 6539-6547.
Han Jurgen Gross. European Journal of Biochemistry. "Fluorescent CMP-Sialic Acids as a Tool to Study the Specificity of the CMP-Sialic Acid Carrier and the Glyococonjugate Sialylation in Permeabilized Cells." 1992. vol. 230(1-2). pp. 269-275.
Ito Y et al. Pure and Applied Chemistry. "Synthesis of Bioactive Sialosides." 1993. vol. 65(4). pp. 753-762.
Fischer et al. Journal of Thrombosis and Thrombolysis. "Comparison of N-Glycan Pattern of Recombinant Human Coagulation Factors II and IX Expressed in Chinese Hamster Ovary (CHO) and African Green Monkey (VERO) Cells." 1996. vol. 3. pp. 57-62.
Charter N W et al. Glycobiology. "Biosynthetic Incorporation of Unnatural Sialic Acids Into Polysialic Acid on Neural Cells." 2000. vol. 10(10). pp. 1049-1056.
Yarema K J et al. Journal of Biological Chemistry. "Metabolic Delivery of Ketone Groups to Sialic Acid Residues Application to Cell Surface Glycoform Engineering." 1998. vol. 273. pp. 31168-31179.
Hang H C et al. Journal of The American Chemical Society. "Ketone Isosteres of 2-N-Acetamidosugars as Substrates for Metabolic Cell Surface Engineering." 2001. vol. 123(6). pp. 1242-1243.
Saxon et al. Science. "Cell Surface Engineering by a Modified Staudinger ." 2000. vol. 287(5460). pp. 2007-2010.
Mahal L K et al. Science. "Engineering Chemical Reactivity on Cell Surfaces Through Oligosaccharide Biosynthesis." 1997. vol. 276(5315). pp. 1125-1128.
Casares et al. Nature Biotechnology. "Antigen-Specific Downregulation of T Cells by Doxorubicin Delivered Through a Recombinant MHC II-Peptide Chimera." 2001. vol. 19. pp. 142-147.
Tsuboi et al. Journal of Biological Chemistry. "6'-Sulfo Sialyl Lex But Not 6-Sulfo Sialyl Lex Expressed on the Cell Surface Supports L-Selectin-Mediated Adhesion." 1996. vol. 271. pp. 27213-27216.
Gross et al. Analytical Biochemistry. "A Highly Sensitive Fluorometric Assay for Sialyltransferase Activity Using CMP-9-Fluoresceinyl-NeuAc as Donor." 1990. vol. 186(1). pp. 127-134.
Yamamoto K et al. Carbohydrate Research. "Chemoenzymatic Synthesis of a Novel Glycopeptide Using a Microbial Endoglycosidase." 1998. vol. 305(3-4). pp. 415-422.
Witte et al. Journal of The American Chemical Society. "Enzymatic Glycoprotein Synthesis: Preparation of Ribonuclease Glycoforms via Enzymatic Glycopeptide Condensation and Glycosylation." 1997. vol. 119(9). pp. 2114-2118.
Haneda et al. Carbohydrate Research. "Transglycosylation of Intact Sialo Complex-Type Oligosaccharides to the N-Acetylglucosamine Moieties of Glycopeptides by Mucor Hiemalis Endo-Beta-N-Acetylglucosaminidase." 1996. vol. 292. pp. 61-70.
Wang et al. Tetrahedron Letters. "Chemoenzymatic Synthesis of a High-Mannose-Type N-Glycopeptide Analog With C-Glycosidic Linkage." 1996. vol. 37(12). pp. 1975-1978.
Singh et al. Chemical Communications. "Glycosidase-Catalysed Synthesis of Osaccharides: A Two-Step Synthesis of the Core Trisaccharide of N-Linked Glycoproteins Using the Beta-N-Acetylhexosaminidase and the Beta-Mannosidase From *Aspergillus* . . . ." 1996.. vol. 8. pp. 993-994.
Koeller et al. Nature Biotechnology. "Emerging Themes in Medicinal Glycoscience." 2000. vol. 18. pp. 835-841.
Grabenhorst et al. European Journal of Biochemistry. "Biosynthesis and Secretion of Human Interleukin 2 Glycoprotein Varients From Baculovirus Infected SF21 Cells." 1993. vol. 215. pp. 189-197.
Douglas et al. Journal of the American Chemical Society. "Polymer-Supported Synthesis of Oligosaccharides." 1991. vol. 113. pp. 5095-5097.
Ichikawa Y et al. Journal of the Americal Chemical Society. "Chemical-Enzymic Synthesis and Conformational Analysis of Sialyl Lewis X and Derivatives." 1992. vol. 114(24). pp. 9283-9298.
Kevin K C et al. Chemistry—A European Journal. "A Paradigm Case for the Merging of Glycal and Enzymatic Assembly Methods in Glycoconjugate Synthesis: A Highly Efficient Chemo-Enzymatic Synthesis of GM3." 1996. vol. 2(11). pp. 1359-1362.
Wong C H et al. Journal of Organic Chemistry. "Enzyme-Catalyzed Synthesis of N-Acetyllactosamine With In Situ Regeneration of Uridine 5'-Diphosphate Glucose and Uridine 5'-Diphosphate Galactose." 1982. vol. 47(27). pp. 5416-5418.
Crout et al. Current Opinion in Chemical Biology. "Glycosidases and Glycosyl Transferases in Glycoside and Oligosaccharide Synthesis." 1998. vol. 2(1). pp. 98-111.
Abuchowski, A et al. Journal of Biological Chemistry. "Alteration of Immunological Properties of Bovine Serum Albumin by Covalent Attachment of Polyethylene Glycol." 1977. vol. 252(11). pp. 3578-3581.
Udenfriend et al. Annual Review of Biochemistry. "How Glycosyl-Phosphatidylinositol-Anchored Membrane Proteins Are Made." 1995. vol. 64. pp. 591-593.
Takeda et al. Trends in Biochemical Sciences. "GPI-Anchor Biosynthesis." 1995. vol. 20(9). pp. 367-371.
Hounsell E F et al. Glycoconjugate Journal. "O-Linked Protein Glycosylation Structure and Function." 1996. vol. 13(1). pp. 19-26.
Tanner et al. Biochimica et Biophysica Acta. 1987. vol. 906(1). pp. 81-91.
Makino Y et al. Journal of Biolochemistry. "Structural Analysis of N-Linked Sugar Chains of Human Blood Clotting Factor IX." 2000. vol. 128. pp. 175-180.
Abeijon et al., 3'-O-(4-Benzoyl)Benzoylcytidine 5'-Triphosphate, 1986, Journal of Biological Chemistry 261(24):11374-11377.
Abuchowski et al., 1977, "Alteration of Immunological Properties of Bovine Serum Albumin by Covalent Attachment of Polyethylene Glycol," Journal of Biological Chemistry 252(11):3578-3581.
Abuchowski et al., 1977, "Effect of Covalent Attachment of Polyethylene Glycol on Immunogenicity and Circulating Life of Bovine Liver Catalase*", Journal of Biological Chemistry, vol. 252(11):3582-3586.
Abuchowski et al., 1984, "Cancer Therapy With Chemically Modified Enzymes. I. Antitumor Properties of Polyethylene Glycol-Asparaginase Conjugates", Cancer Biochem. Biophys. 7(2):175-186.
Adelhorst et al., Structure-Activity Studies of Glucagon-Like Peptide-1, J. Biol. Chem., vol. 269(9), pp. 6275-6278 (1994).
Ailor et al., 2000, "N-Glycan Patterns of Human Transferrin Produced in Trichoplusia NI Insect Cells: Effects of Mammalian Galactosyltransferase", Glycobiology 10(8):837-847.

(56) References Cited

OTHER PUBLICATIONS

Ajisaka et al., Efficient Synthesis of O-Linked Clycopeptide by a Transglycosylation Using Endo a-N-Acetylgalactosaminidase From *Streptomyces* sp, Biosci. Biotechnol. Biochem, Vol. 65(5), pp. 1240-1243 (2001).

Alam K S M et al, 1998, "Expression and Purification of a Mutant Human Growth Hormone That Is Resistant to Proteolytic Cleavage by Thrombin, Plasmin and Human Plasma In Vitro," Journal of Biotechnology 65(Feb. 3):183-190.

Allegre et al., 2006, "Cholesterol Removal by Nanofiltration: Applications in Nutraceutics and Nutritional Supplements", J. Membrane Science 269(1-2):109-117.

Altmann et al., 1999, "Insect Cells as Hosts for the Expression of Recombinant Glycoproteins", Glycoconjugate Journal 16(2):109-123.

Aplin et al., "Preparation, Properties and Applications of Carbohydrate Conjugates of Proteins and Lipids," 1981, CRC Critical Reviews in Biochemistry, vol. 10(4), pp. 259-306.

Barrios et al., "Length of the Antibody Heavy Chain Complementarity Determining Region 3 as a Specificity-Determining Factor", J. Mol. Recognit., 17(4):332-338 (2004).

Beauchamp et al., 1983, "A New Procedure for the Synthesis of Polyethylene Glycol-Protein Adducts; Effects on Function, Receptor Recognition, and Clearance of Superoxide Dismutase, Lactoferrin, and Alpha2-Macroglobulin", Analytical Biochemistry 131(1)25-33.

Mizugushi et al., 1999, "Structural Elements of Factor VIIa Required for Active Site Formation," Thrombosis and Haemostasis (1474):466.

Mollicone et al., "Acceptor specificity and tissue distribution of three human alpha-3-fucosyltransferases." Eur. J. Biochem., vol. 191(1), pp. 169-176 (1990).

Monaco et al., "Expression of Recombinant Human Granulocyte Colony-Stimulating Factor in CHO DHFR-Cell: New Insights Into the In Vitro Amplification Expression System", Gene, vol. 180, pp. 145-150 (1996).

Morimoto et al., "Biological and physicochemical characterization of recombinant human erythropoietins fractionated by Mono Q column chromatography and their modification with sialyltransferase." 1996, Glycoconjugate J. 13(6):1013-1020.

Muller et al., "Localization of O-Glycosylation Sites on Glycopeptide Fragments From Lactation-Associated MUC1," J. Biol. Chem., 272(40): 24780-24793 (1997).

Muller et al., "High Density O-Glcosylation on Tandem Repeat Peptide From Secretory MUC1 of T47D Breast Cancer Cells," J. Biol. Chem, 274(26): 18165-18172 (1999).

N-Acetylgucosaminetransferase, from http://www.online-medical-dictionary.org/N-Acetylglucosaminyltrasnferases.asp?q=N-Acetylglucosaminyltransferases, pp. 1-2, accessed Apr. 14, 2009.

Nagata et al., "The Chromosomal Gene Structure and Two mRNAs for Human Granulocyte Colony-Stimulating Factor", EMBO J., vol. 5(3), pp. 575-581 (1986).

Natsuka et al., "Molecular Cloning of a cDNA Encoding a Novel Human Leukocyte alpha-1,3-Fucosyltranferase Capable of Synthesizing the Sialyl Lewis X Determinant." J. Biol. Chem., vol. 269(24): pp. 16789-16794 (1994).

NCBI—Accession No. NCAA26095 (2 pgs.) downloaded Nov. 14, 2007.

NCBI—Accession No. NP_058697 (3 pgs.) downloaded Nov. 14, 2007.

NCBI—Accession No. NP_999299 (2 pgs.) downloaded Sep. 27, 2011.

NCBI Database Hits for Erythropoietin Protein Sequences (3 pgs.) downloaded Nov. 14, 2007.

Nelsestuen, G. et al., "Vitamin K-Dependent Proteins." Vitamins and Hormones, 2000, vol. 58, pp. 355-389.

Ngo et al., 1994, "Computational Complexity, Protein Structure Prediction, and the Levinthal Paradox," The Protein Folding Problem and Tertiary Structure Prediction, Chapter 14, pp. 433-440.

Ngo et al., 1994, "The Protein Folding Problem and Tertiary Structure Prediction" Chapter 14: Computational Complexity Protein Structure Prediction, and the Levinthal Paradox, pp. 492-495.

Nilsson et al., "Immobilization of Ligands with Organic Sulfonyl Chlorides." 1984, Methods Enzymol. 104:56-69.

Nucci, M L et al., 1991, "The Therapautic Value of Poly(Ethylene Glycol)-Modified Proteins," Advanced Drug Delivery Reviews 6:133-151.

Nunez et al., "The Synthesis and Characterization of alpha and Beta-L-fucopyranosyl Phosphates and GDP fucose." Can. J. Chem., vol. 59(14), pp. 2086-2095 (1981).

O'Connell et al., "The Influence of Flanking Sequence on the O-Glycosylation of Threonine in Vitro." 1992, J. Biological Chemistry 267(35):25010-25018.

Oetke et al., "Versatile Biosynthetic Engineering of Sialic Acid in Living Cells Using Synthetic Sialic Acid Analogues." 2002, Journal of Biological Chemistry 277(8):6688-6695.

Oh-Eda et al., "O-Linked Sugar Chain of Human Granulocyte Colony-Stimulating Factor Protects It Against Polymerization and Denaturation Allowing It to Retain Its Biological Activity", J. Biol. Chem., vol. 265, pp. 11432-11435 (1990).

Olson et al., "Structural Basis for Recognition of Phosphorylated High Mannose Oligosaccharids by the Cation-dependent Mannose 6-Phosphate Receptor." 1999, J. Biological Chemistry 274(42):29889-29896.

Orlean, "Vol. III: The Molecular and Cellular Biology of the Yeast *Saccharomyces*: Cell Cycle and Cell Biology", in Biogenesis of Yeast Wall and Surface Components, Chapter 3, pp. 229-362, Cold Spring Harbor Laboratory Press (1997).

Orskov et al., "Complete Sequences of Glucogon-Like Peptide-1 From Human and Pig Small Intestine", J. Biol. Chem., vol. 264(22), pp. 12826-12829 (1989).

Palacpac et al., "Stable expression of Human Beta1, 4-galactosyltransferase in plant cells modifies N-linked glycosylation patterns." 1999, PNAS 96(8):4692-4697.

Palcic et al., "Enzymic Synthesis of Oligosaccharides Terminating in the Tumor-Associated Sialyl-Lewis-a Determinant." Carbohydr. Res., vol. 190(1), pp. 1-11 (1989).

Park et al., "Characterization of the Cell Surface Receptor for a Multi-Lineage Conlony-Stimulating Factor (CS-F2a)," 1986, J. Biological Chemistry 261(1):205-210.

Patra et al., "Optimization of Inclusion Body Solubilization and Renaturation of Recombinant Human Growth Hormone from *Escherichia coli*." 2000, Protein Expression and Purification, vol. 18, pp. 182-190.

Paulson et al., "Reactivation of Asialo-Rabbit Liver Binding Protein by Resialylation with Beta-D-Galactoside Alpha-2 -> 6 Sialyltransferase." 1977, J. Biological Chemistry 252(23):8624-8628.

Plummer et al., "Novel, Specific O-Glycosylation of Secreted *Flavobacterium meningosepticum* Proteins." 1995, J. Biological Chemistry 270(22):13192-13196.

PNGase-F Amidase Sequence from *F. meningosepticum* (Registry Nos. 128688-70-0).

PNGase-F Amidase Sequence from *F. meningosepticum* (Registry Nos. 128688-71-1).

Prati et al., "Engineering of Coordinated Up- and Down-Regulation of Two Glycosyltransferases of the O-Glycosylation Pathway in Chines Hamster Ovary (CHO) Cells", Biotech and Bioeng., vol. 79(5), pp. 580-585 (2002).

Prieels et al., "Co-purification of the Lewis Blood Group N-Acetylglucosaminide alpha 1 -> 4 Fucosyltransferase and an N-Acetylglucosaminide alpha 1 -> Fucosyltransferase from Human Milk." J. Biol. Chem., vol. 256(20), pp. 10456-10463 (1981).

Pyatak et al., "Preparation of a Polyethylene Glycol: Superoxide Dismutase Adduct and an Examination of Its Blood Circulating Life and Anti-Inflammatory Activity," 1980, Res. Commun. Chem. Pathol. Pharmacol. 29(1):113-127.

Rabouille et al., "The *Drosophila* GMII gene encodes a Golgi alpha-mannosidase II." 1999, J. Cell. Biol. 112(pt. 19):3319-3330.

Rasko et al., "Cloning and Characterization of the alpha(1,3/4) Fucosyltransferase of *Helicobacter pylori*." J. Biol. Chem., vol. 275(7), pp. 4988-4994 (2000).

(56) References Cited

OTHER PUBLICATIONS

Reff et al., "Future Monoclonal Antibodies in the Treatment of Hematologic Maligancies." 2002, Cancer Control 9(2):152-166.
Reis et al., "Industrial Scale Harvest of Proteins from Mammalian Cell Culture by Tangential Flow Filtration." 1991, Biotechnology and Bioengineering 38:413-422.
Rosenthal et al., "Isolation of Peptidoglycan and Soluble Peptidoglycan Fragments." 1994, Methods Enzymol. 235:253-285.
Rotondaro et al., "Purification and characterization of two recombinant human granulocyte colony-stimulating factor glycoforms." Mol. Biotech., 11: 117-128 (1999).
Rudikoff et al., "Single Amino Acid Substitution Altering Antigenbinding Specificity." Proc. Natl. Acad. Sci. USA, 79(6):1979-1983 (1982).
R&D Systems, Fibroblast Growth Factors (FGFs), Internet Page From www.mdsystems.com/mini_review_detail_objectname_ MR01_FGFs.aspx, 2001, printed Mar. 10, 2011.
Sadler et al., "Purification of Mammalian Glycisyltransferases." 1982, Methods in Enzymology 83:458-514.
Sandberg et al., "Structual and Functional Characterization of B-Domain Deleted Recombinant Factor VII." 2001, Seminars in Hematology 38(2 Suppl. 4):4-12.
Saneyoshi et al., "Equine Follicle-Stimulating Hormone: Molecular Cloning of Beta Subunit and Biological Role of Asparagine-Linked Oligosaccharide at Asparagine of alpha Subunit." 2001, Biology of Reproduction 65(6):1686-1690.
Sasaki et al., "Carbohydrate Structure of Erythropoietin Expressed in Chinese Hamster Ovary Cells by a Human Erythropoietin cDNA", J. Biol. Chem., 262(25): 12059-12076 (1987).
Sasaki et al., "Expression Cloning of a Novel alpha1,3-Fucosyltranferase that is Involved in Biosynthesis of the Sialyl Lewis x Carbohydrate Determinants in Leukocytes." J.Biol. Chem., 269: 14730-14737 (1994).
Saxon et al., "Cell Surface Engineering by a Modified Staudinger Reaction." 2000, Science 287(5460):2007-2010.
Bedard et al., 1994, "Maximization of Recombinant Protein Yield in the Insect Cell/Baculovirus System by One-Time Addition of Nutrients to High-Density Batch Cultures", Cytotechnology 15(1-3):129-138.
Bennett et al., "Cloning of a Human UDP-N-Acetyl-a-D-Galactosamine: Polypeptide N-Acetylgalactosaminyltransferase That Complements Other GalNAc-Transferases in Complete O-Glycosylation of the MUC1 Tandem Repeat," 1998, Journal of Biological Chemistry 273(46):30472-30481.
Bennett et al., "A Novel Human UDP-N-Acetyl-D-Galactosamine: Polypeptide N-Acetylgalactosaminyltransferase, GalNAc-T7 With Specificity for Partial GalNAc-Glycosylated Acceptor Substrates," 1999, FEBS Letters 460(2):226-230.
Berger et al., 1988, "Preparation of Polyethylene Glycol-Tissue Plasminogen Activator Adducts That Retain Functional Activity: Characteristics and Behavior in Three Animal Species", Blood 71(6):1641-1647.
Berg-Fussman et al., 1993, "Human Acid Beta-Glucosidase", Journal of Biological Chemistry 268(20):14861-14866.
Bhadra et al., "PEGnology: A Review of PEG-Ylated Systems," 2002, Pharmazie 57(1):5-29.
Bhatia et al., 1989, "Use of Thiol-Terminal Silanes and Heterobifunctional Crosslinkers for Immobilization of Antibodies on Silica Surfaces", Analytical Biochemistry 178(2):408-413.
Bickel et al., 2001, "Delivery of Peptides and Proteins Through the Blood-Brain Barrier", Advanced Drug Delivery Reviews 46(1-3):247-279.
Bishop et al., "Both of the Beta-Subunit Carbohydrate Residues of Follicle-Stimulating Hormone Determine the Metabolic Clearance Rate and In Vivo Potency*", Endocrinology 136(6):2635-2640 (1995).
Bjoern et al., 1992, "Human Plasma and Recombinant Factor VII", Journal of Biological Chemistry 266(17):11051-11057.
Boccu et al., 1983, "Coupling of Monomethoxypolyethyleneglycols to Proteins via Active Esters", Z. Naturforsch 38C:94-99.

Boime et al., 1999, "Glycoprotein Hormone Structure-Function and Analog Design", Recent Prog. Horm. Res. 54:271-289.
Boissel et al., 1993, "Erythropoietin Structure-Function Relationships—Mutant Proteins That Test a Model of Tertiary Structure", Journal of Biological Chemistry 268(21):15983-15993.
Bork et al., 1996, "Go Hunting in Sequence Databases But Watch Out for Traps", Trends in Genetics 12(10):425-427.
Bork, 2000, "Powers and Pitfalls in Sequence Analysis: The 70% Hurdle," Genome Research 10(4):398-400.
Bouizar et al., "Purification and Characterization of Calcitonin Receptors in Rat Kidney Membranes by Covalent Cross-Linking Techniques," 1986, European Journal of Biochemistry 155(1):141-147.
Boyd et al., 1995, "The Effect of the Removal of Sialic Acid, Galactose and Total Carbohydrate on the Functional Activity of Campath-1H", Molecular Immunology 32(17-18):1311-1318.
Brenner, 1999, "Errors in Genome Annotation," Trends in Genetics 15(4):132-133.
Brockhausen et al., "Glycoprotein and Their Relationship to Human Disease", Acta Anatomica, 161: 36-78 (1998).
Brockhausen et al., Enzymatic Basis for Sialyl-Tn Expression in Human Colon Cancer Cells, Glycoconj. J., vol. 15, pp. 595-603 (1998).
Broun et al., "Catalytic Plasticity of Fatty Acid Modification Enzymes Underlying Chemical Diversity of Plant Lipids", Science, vol. 282(5392), pp. 1315-1317 (1998).
Browning et al., "Studies on the Differing Effects of Tumor Recrosis Factor and Lymphotoxin on the Growth of Several Human Tumor Lines," 1989, Journal of Immunology 143(6):1859-1867.
Bueckmann et al., 1981, "Functionalization of Poly(Ethylene Glycol) and Monomethoxy-Poly(Ethylene Glycol)", Angewandte Makromolekulare Chem., vol. 182(5):1379-1384.
Burns et al., 2002, "Purification and Characterization of the Yeast-Expressed Erythropoietin Mutant EPO (R103A), A Specific Inhibitor of Human Primary Hematopoietic Cell Erythropoiesis", Blood 99(12):4400-4405.
Bijsterbosch et al., 1996, "Quantitative Analysis of the Targeting of Mannose-Terminal Glucocerebrosidase-Predominant Uptake by Liver Endothelial Cells", European Journal of Biochemistry 237(2):344-349.
Butnev et al., 1998, "Hormone-Specific Inhibitory Influence of Alpha-Subunit ASN56 Oligosaccharide on In Vitro Subunit Association and Follicle-Stimulating Hormone Receptor Binding of Equine Gonadotropins", Biology of Reproduction 58(2):458-469.
Byun et al., 1992, "Binding Kinetics of Thrombin and Antithrombin III With Immobilized Heparin Using a Spacer", ASAIO Journal, 38(3), pp. M649-M653.
Cantin et al., "Polyethylene Glycol Conjugation at CYS232 Prolongs the Half-Life of Alpha1 Proteinase Inhibitor", Am. J. Respir. Cell Mol. Biol., 27(6): 659-665 (2002).
Casares et al., 2001, "Antigen-Specific Downregulation of T Cells by Doxorubicin Delivered Through a Recombinant MHCII-Peptide Chimera", Nature Biotechnology (Continuation of Bio/Technology) 19(2):142-147.
Chaffee et al., "IgG Antibody Response to Polyethylene Glycol-Modified Adenosine Deaminase in Patients With Adenosine Deaminase Deficiency," 1992, Journal of Clinical Investigation 89(5):1643-1651.
Chang et al., 1999, "Engineered Recombinant Factor VII . . . ," Biochemistry 38(34):10940-10948.
Charter et al., "Biosynthetic Incorporation of Unnatural Sialic Acids Into Polysialic Acid on Neural Cells," 2000, Glycobiology 10(10):1049-1056.
Chern et al., 1991, "Structural Role of Amino Acids 99-110 in Recombinant Human Erythropoietin", European Journal of Biochemistry 202(2):225-229.
Chiba et al., 1995, "Cloning and Expression of the Carboxypeptidase Gene From *Aspergillus* Saitoi and Determination of the Catalytic Residues by Site-Directed Mutagenesis", Biochemical Journal 308(2):405-409.
Chrisey et al., "Covalent Attachment of Synthetic DNA to Self-Assembled Monolayer Films," 1996, Nucleic Acids Research 24(15):3031-3039.

(56) References Cited

OTHER PUBLICATIONS

Clark et al., 1996, "Long-Acting Growth Hormones . . . ," The Journal of Biological Chemistry 271(36):21969-21977.
Cohn et al., "Biodegradable PEO/PLA Block Polymers," J. Biomed. Mater. Res,. 22(11): 993-1009 (1988).
Cointe et al., 2000, Unusual N-Glycosylation of a Recombinant Human Erythroprotein Expressed in a Human Lymphoblastoid Cell Line Does Not Alter Its Biological Properties, Glycobiology 10(5):511-519.
Conradt et al., 1987, "Structure of the Carbohydrate Moiety of Human Interferon-Beta Secreted by a Recombinant Chinese Hamster Ovary Cell Line*", Journal of Biological Chemistry 262(30):14600-14605.
Cope et al., 1991, "Molecular Cloning of a Gene Involved in Lipooligosaccharide Biosynthesis and Virulence Expression by *Haemophilus influenzae* Type B", Molecular Microbiology 5(5):1113-1124.
Copeland, 2000, "Enzymes: A Practical Introduction to Structure, Mechanism and Data Analysis", 2nd ed., Wiley-VCH, New York, pp. 146-150.
Costa et al. "Stable Expression of the Golgi Form and Secretory Variants of Human Fucosyltransferase III From BHK-21 Cells", J Biol. Chem., vol. 272(17), pp. 11613-11621 (1997).
Crout et al., 1998, "Glycosidases and Glycosyl Transferases in Glycoside and Oligosaccharide Synthesis", Current Opinion in Chemical Biology 2(1):98-111.
Culajay et al., "Thermodynamic Characterization of Mutants of Human Fibroblast Growth Factor 1 With an Increased Physiological Half-Life," Biochemistry. vol. 39, pp. 7153-7158 (2000).
Deacon, "Therapeutic Strategies Based on Glucagon-Like Peptide 1", Diabetes, vol. 54: pp. 2181-2189 (2004).
Definition of Insect Cells, From http://www.biochem.northwestern.edu/holmgren/Glossary/Definitions/Def-I/insect_cells.html, p. 1, accessed Apr. 14, 2009.
DeFrees et al., 2006, Glycopegylation of Recombinant Therapeutic Proteins Produced in *Escherichia coli*, Glycobiology 16(9):833-843.
Delgado et al., 1990, "Coupling of Poly(Ethylene Glycol) to Albumin Under Very Mild Conditions by Activation With Tresyl Chloride: Characterization of the Conjugate by Partitioning in Aqueous Two-Phase Systems", Biotechnology and Applied Biochemistry 12(2):119-128.
Delgado et al., 1992, "The Uses and Properties of PEG-Linked Proteins," Critial Reviews in Therapeutic Drug Carrier Systems 9(3-4):249-304.
Detty et al., 1982, "Telluropyrylium Dyes. 1. 2,6-Diphenyltelluropyrylium Dyes", Journal of Organic Chemistry 47:5416-5418.
De Vries et al., "Acceptor Specificity of Different Length Constructs of Human Recombinant Alpha1,3/4-Fucosyltransferases—Replacement of the Stem Region and the Transmembrane Domain of Fucosyltransferase V by Protein A Results in an Enzyme With GDP-Fucose Hydrolyzing Activity", J. Biol. Chem, vol. 270(15), pp. 8712-8722 (1995).
De Vries et al., "Acceptor Specificity of GDP-Fuc:GalBeta1 forward arrow 4GlcNAc-R Alpha3-Fucosyltransferase VI (FucT VI) Expressed in Insect Cells as Soluble, Secreted Enzyme", Glycobiology, vol. 7(7), pp. 921-927 (1997).
Dickinson et al., 1996, "Identification of Surface Residues Mediating Tissue Factor Binding an Catalytic Function of the Serine Protease Factor VIIa," Proceedings of the National Academy of Sciences of the United States 93:14379-14384.
Dinter et al., "Glycosylation Engineering in Chinese Hamster Ovary Cells Using Tricistronic Vectors", Biotechnol. Lett., vol. 22(1), pp. 25-30 (2000).
Doerks et al, 1998, "Protein Annotation: Detective Work for Function Prediction," Trends in Genetics 14(6):248-250.
Douglas et al., 1991, "Polymer-Supported Synthesis of Oligosaccharides," Journal of the American Chemical Society 113(13):5095-5097.
Dube et al., "Glycosylation at Specific Sites of Erythropoietin Is Essential for Biosynthesis, Secretion, and Biological Function", J. Biol. Chem., vol. 263(33), pp. 17516-17521 (1988).
Dudziak et al., "Cyclodextrin-Assisted Glycan Chain Extension on a Protected Glycosyl Amino Acid", Tetrahedron, 2000, vol. 56(32), pp. 5865-5869.
Dumas et al., "Enzymatic Synthesis of Sialyl LEX and Derivatives Based on a Recombinant Fucosyltransferase", Bioorg. Med. Chem. Lett., vol. 1(8), pp. 425-428 (1991).
Dunn et al., 1991, Eds. "Polymeric Drugs and Drug Delivery Systems," ACS Symposium Series, American Chemical Society, Washington D.C. vol. 469.
Durieux et al., 2001, "Synthesis of Biotinylated Glycosulfopeptides by . . . ," Tetrahedron Letters 42(12):2297-2299.
Dwek et al., 1995, "Glycobiology: 'The Function of Sugar in the IgG Molecule'", J. Anat. 187(Pt. 2):279-292.
Eavarone et al., 2000, "Targeted Drug Delivery to C6 Glioma by Transferrin-Coupled Liposomes", Journal of Biomedical Material Research 51(1):10-14.
Edge et al., "Deglycosylation of Glycoproteins by Trifluoromethanesulfonic Acid," Anal. Biochem., 118(1): 131-137 (1981).
Elhalabi et al., "Synthesis and Applications for Unnatural Sugar Nucleotides", Curr. Med. Chem, vol. 6(2), pp. 93-116 (1999).
EMBL Accession No. M80599 and M86935 (Jan. 23, 1992), *Escherichia coli* Lipopolysaccharide Core Biosynthesis Protein Operon (rfaQ, rfaP, rfaG, rfaB, rfaI, rfaJ) Genes, Complete CDs.
EMBL Accession No. S56361 (May 4, 1993), rfa Gene Cluster, rfaP-Lipopolysaccharide Core Production Protein, rfaB=Lipopolysaccharide Core Production Protein [*Salmonella typhimurium*, LT2, Genomic, 3 Genes, 815 NT.
EMBL Accession No. U00039 (Jun. 2, 1994), *E. coli* Chromosomal Region From 76.0 to 81.5 Minutes.
Ernst et al., 1999, "Substrate and Donor Specificity of Glycosyl Transferases", Glycoconj. J. 16(2):161-170.
Espuelas et al., "Synthesis of an Amphiphilic Tetraantennary Mannosyl Conjugate and Incorporation Into Liposome Carriers", Bioorg Med. Chem. Lett., vol. 13(15): pp. 2557-2560 (2003).
Factor IX of *Homo sapien*, Genbank Accession No. CAA01607, pp. 1-2, Dated March 2, 1995.
Factor IX, Genbank Accession No. AAA98726, pp. 1-3, Dated Apr. 30, 1996.
Fairhall et al., "Growth Hormone (GH) Binding Protein and GH Interactions In Vivo in the Guinea Pig", Endocrinology, vol. 131(4), pp. 1963-1969 (1992).
Fan et al., 1997, "Detailed Studies on Substrate Structure Requirements of Flycoamidases A and F", Journal of Biological Chemistry 272(43):27058-27064.
Feldman et al., "Engineering N-Linked Protein Glycosylation With Diverse O Antigen Lipopolysaccharide Structures in *Escherichia coli*", Proc. Natl. Acad. Sci. USA, vol. 102(8), pp. 3016-3021 (2005).
Felix et al., Synthesis of Symmetrically and Asymmetrically Branched PEGylating Reagents, J. Peptide Res., 63: 85-90 (2004).
Fibi et al., 1995, "N- and O-Glycosylation Muteins of Recombinant Human Erythropoietin Secreted From BHK-21 Cells", Blood 85(5):1229-1236.
Fischer et al., 1998, "Recombinant Coagulation Factor IX: Glycosylation Analysis and In Vitro Conversion Into Human-Like Sialylation Pattern", Thrombosis Research 89(3):147-150.
Fischer, B. et al., 1996, Comparison N-Glycan Pattern of Recombinant Human Coagulation Factors II and IX Expressed in Chinese Hamster Ovary (CHO) and African Green Monkey (VERO) Cells, Journal of Thrombosis and Thrombolysis, vol. 3, pp. 57-62.
Flynn et al., 2000, "Campath-1H Monoclonal Antibody Therapy", Current Opinions Oncology 12 (6):574-581.
Francis et al., "Pegylation of Cytokines and Other Therapeutic Proteins and Peptides: The Importance of Biological Optimisation of Coupling Techniques", Intl. J. Hematol., vol. 68(1), pp. 1-18 (1998).
Fritz et al., 2004, "The Beginnings of Mucin Biosynthesis: The Crystal Structure of UDP-GalNAc:Polypeptide Alpha-N-Acetylgalactosaminyltransferase-T1", Proceedings of the National Academy of Sciences of the USA 101(43):15307-15312.

(56) References Cited

OTHER PUBLICATIONS

Fritz et al., 2006, "Dynamic Association Between the Catalytic and Lectin Domains of Human UDP-GalNAc:Polypeptide Alpha-N-Acetylgalactosaminyltransferase-2", Journal of Biological Chemistry 281(13):8613-8619.
Garnett et al., 2002, "Targeted Drug Conjugates: Principles and Progress", Advanced Drug Delivery Reviews 53(2):171-216.
Gatot et al., 1998, "Conservative Mutations in the Immunosuppressive Region of the Bovine Biological Leukemia Virus Transmembrane Protein Affect Fusion But Not Infectivity In Vivo", Journal of Biological Chemistry 273(21):12870-12880.
Ge et al., "Cloning and Heterologous Expression of an Alpha1,3-Fucosyltransferase Gene From the Gastric Pathogen *Helicobacter pylori*", J. Biol. Chem., 272(34): 21357-21363 (1997).
GenBank Accession No. D49915 (Sep. 1, 1995), *Gallus gallus* mRNA for Chondroitin 6-Sulfotransferase, Complete CDs.
GenBank Accession No. U18918 (Oct. 1, 1995), Human Heparan Sulfate-N-Deacetylase/N-Sulfotransferase mRNA, Clone HSST, Complete CDs.
GenBank Accession No. U02304 (Mar. 8, 1994), *Mus musculus* LAF1 Sulfotransferase mRNA, Complete CDs.
Gervais et al., Glycosylation of Human Recombinant Gonadotrophins: Characterization and Batch-To-Batch Consistency, Glycobiology, 13(3): 179-189 (2003).
Gilbert et al., 1996, "Effect of Lipids on Insect Cell Growth and Expression of Recombinant Proteins in Serum-Free Medium", Cytotechnology 22(1-3):211-216.
Gillis et al., 1988, "Production of Recombinant Human Colony Stimulating Factors in Yeast", Behring Inst. Mitt. August 83:1-7.
Ginns, 2002 (printed Jun. 21), PEG Glucocerebrosidase, Internet page www.gaucher.org.uk/peg2.prg.
Gombotz et al., "PEGylation: A Tool for Enhanced Protein Delivery," In Controlled Drug Delivery, Park et al. (Eds.), Chapter 12, pp. 110-123, ACS Symposium Series, American Chemical Society, Washington DC (2000).
Goodson, R J., 1990, "Site-Directed PEGylation of Recombinant Interleukin-2 at Its Glycosylation Site," Biotechnology 8:343-346.
Gotschlich, 1994, "Genetic Locus for the Biosynthesis of the Variable Portion of *Neisseria gonorrhoeae* Lipooligosaccharide", J. Exp. Med., Coden: Jemeav; ISSN: 0022-1007, 180(6):2181-2190.
Grabenhorst et al., 1993, "Biosynthesis and Secretion of Human Interleukin 2 Glycoprotein Variants From Baculovirus-Infected SF21 Cells", European Journal of Biochemistry 215(1):189-197.
Grabenhorst et al., "The Cytoplasmic, Transmembrane, and Stem Regions of Glycosyltransferases Specify Their In Vivo Functional Sublocalization and Stability in the Golgi", J. Biol. Chem., 274(51): 36107-36116 (1999).
Grodberg et al., 1993, "Alanine Scanning Mutagenesis of Human Erythropoietin Identifies Four Amino Acids Which Are Critical for Biological Activity", European Journal of Biochemistry 218(2):597-601.
Gross et al., 1989, "Transfer of Synthetic Sialic Acid Analogues to N- and O-Linked Glycoprotein Glycans Using Four Different Mammalian Sialyltransferases", Biochemistry 28(18):7386-7392.
Saxon et al., "Investigating Cellular Metabolism of Synthetic Azidosugars with the Staudinger Ligation." J. Am. Chem. Soc., vol. 124(50): pp. 14893-14902 (2002).
Schachter et al., "The Biosysthesis of Branched O-Linked Glycans", 1989, Society for Experimental Biology, pp. 1-26 (Great Britain).
Schlaeger, 1996, "Medium Design for Insect Cell Culture." Cytotechnology 20(1-3):57-70.
Schwientek et al., "Efficient intra- and extracellular production of human beta-1, 4-galactosyltransferase in *Saccharomyces cerevisiae* is mediated by yeast secretion leaders." 1994, Gene 145(2):299-303.
Schwientek et al., "Functional Conservation of Subfamilies of Putative UDP-N-acetylagalactosamine: Polypeptide N-Acetylgalactosaminyltransferases in *Drosophila, Caenorhabditis elegans*, and Mammals." 2002, Journal of Biological Chemistry 277(25):22623-22638.

Scouten, William H., 1987, "[2] A Survey of Enzyme Coupling Techniques," Methods in Enzymology 135:30-65.
Seely et al., "Use of ion-exchange chromatography and hydrophobic interaction chromatography in the preperation and recovery of polyetheylene glycol-linked proteins." J. Chromatog., 908: 235-241 (2001).
Seffernick et al., "Melamine Deaminase and Atrazine Chlorohydrolase: 98 percent Identical but Functionally Different." J. Bacteriol., vol. 183(8), pp. 2405-2410 (2001).
Seitz, 2000, "Glycopeptide Synthesis and the Effects of Glycosylation on Protein Structure and Activity." Chembiochem 1(4):214-246.
Shah et al., "Transcellular Delivery of an Insulin-Transferrin Conjugate in Enterocyte-like Caco-2 Cells." 1996, J. Pharm. Sci. 85(12):1306-1311.
Shapiro et al., "The safety and efficacy of recombinant human blood coagulation factor IX in previously untreated patients with severe or moderately severe hemophilia B." 2005, Blood, 105(2):518-525.
Shen et al., "Cis-Aconityl Spacer Between Daunomycin and Macromolecular Carriers: A Model of pH-Sensitive Linkage Releasing Drug From a Lysosomotropic Conjugate," Biochem. Biophys. Res. Commun., 102(3): 1048-1054 (1981).
Sheridan, "The Most Common Chemical Replacements in Drug-Like Compounds." J., Chem Inf. Comput. Sci. (2002), vol. 42, pp. 103-108.
Shinkai et al., "High-Level Expression and Purification of a Recombinant Human alpha-1,3-Fucosyltransferase in Baculovirus-Infected Insect Cells." Prot. Exp. Purif., 10: 379-385 (1997)(Khoo et al.?).
Singh et al., "Glycosidase-catalysed synthesis of oligosaccharides: a two step synthesis of the core trisaccharide of N-linked glycoproteins using the beta-N-acetylhexosaminidase and the beta-mannosidase from *Aspergillus oryzae*." 1996, Chem. Commun. 1996(8):993-994.
Sinha et al., "Release of Soluble Peptidoglycan from Growing Gonococci: Demonstration of Anhydro-Muramyl-Containing Fragments." 1980, Infection and Immunity 29(3):914-925.
Sinclair et al., "Glycoengineering: The Effect of Glycosylation on Properties of Therapeutic Proteins." J. Pharm. Sci., vol. 94, pp. 1626-1635 (2005).
Skolnick et al., 2000, "From Genes to Protein Structure and Function: Novel Applications of Computational Approaches in the Genomic Era," Trends in Biotechnology 18(1):34-39.
Smith et al., "The challenges of genome sequence annotation or The devil is in the details." 1997, Nature Biotechnology (Continuation of Bio/Technology) 15(12):1222-1223.
Snider et al., "Characterization of the Heterogeneity of Polyethylene glycol-modified superoxide dismutase by chromatographic and electrophoretic techniques." J. Chromatogr., A 599(1-2): 141-155 (1992).
Sojar et al., "A Chemical Method for the Deglycosylation of Proteins," Arch. Biochem. Biophys., 259(1): 52-57 (1987).
Song et al., "Enhanced Neuroprotective Effects of Basic Fibroblast Growth Factor in Regional Brain Ischemia after Conjugation to Blood-Brain Barrier Delivery Vector." 2002, J. Pharmacol. Exp. Ther. 301(2):605-610.
Sørensen, B.B. et al., "Incorporation of an Active Site Inhibitor in Factor VIIa Alters the Affinity for Tissue Factor." Journal of Biological Chemistry, 1997, vol. 272(18), pp. 11863-11868.
Srinivasachar et al., "New Protein Cross-Linking Reagents That are Cleaved by Mild Acid." 1989, Biochemistry 28(6):2501-2509.
Staudacher, "Alpha 1,3-Fucosyltransferases." Trends Glycosci. Glycotechnol., vol. 8(44), pp. 391-408 (1996).
Stemmer, Willem PC, "Rapid Evolution of a Protein In Vitro by DNA Shuffling," Nature, 370(6488): 389-391 (1994).
Stemmer, Willem PC, "DNA Shuffling by Random Fragmentation and Reassembly: In Vitro Recombination for Molecular Evolution," Proc. Natl. Acad. Sci. USA, 91(22): 10747-10751 (1994).
Stephens et al., "The Pyruvate Dehydrogenase Complex of *Escherichia*." 1983, European J. of Biochemistry 133(1):155-162.
Stephens et al., "The Pyruvate Dehydrogenase Complex of *Escherichia coli* K12." 1983, European J. of Biochemistry 133(3):481-489.
Stephens et al., "Nucleotide sequence of the lipoamide dehydrogenase gene of *Escherichia coli* K12." 1983, European J. of Biochemistry 135(3):519-527.

(56) References Cited

OTHER PUBLICATIONS

Strausberg et al., "Generation and Initial Analysis of More than 15,000 full-length human and mouse cDNA sequences." Proc Natl Acad Sci USA, 99(26): 16899-16903 (2002).
Swiss-Prot Accession No. P27129 (Aug. 1, 1992), Lipopolysaccharide 1, 2-Glucosyltransferase (EC 2.4.1.58).
Swiss-Prot Accession No. P25740 (May 1, 1992), Lipopolysaccharide Core Biosynthesis Protein rfaG (Glucosyltransferase I).
Swiss-Prot Accession No. P19817 (Feb. 1, 1991), Lipopolysaccharide 1, 2-Glucosyltransferase (EC 2.4.1.58).
Takane et al., "Chronopharmacology of Antitumor Effect Induced by Interferon-beta in Tumor-Bearing Mice." 2000, J. Pharmacology and Experimental Therapeutics 294(2):746-752.
Takeda et al., "GPI-Anchor Biosynthesis," 1995, Trends Biochem. Sci. 20(9):367-371.
Takeuchi et al., 1990, "Role of Sugar Chains in the In Vitro Biolgoical Activity of Human Erythropoietin Produced in Recombinant Chinese Hamster Ovary Cells," Journal of Biological Chemistry 265(21):12127-12130.
Takeya et al., "Bovine Factor VII." Journal of Biological Chemsitry, 263(29); 14868-77 (1988).
Taniguchi et al., "A glycomic approach to the identification and characterization of glycoprotein function in cells transfected with glycosyltransferase genes." 2001, Proteomics 1(2):239-247.
Tanner et al., "Protein Gycosylation in Yeast," 1987, Biochim. Biophys. Acta. 906(1):81-91.
Tarui et al., "A Novel Cell-Free Translation/Glycosylation System Prepared from Insect Cells." 2000, J. Biosci. Bioeng. 90(5):508-514.
Taylor et al., 1991, Protein Immobilization Fundamentals and Applications, Manual.
Ten Hagen et al., "Characterization of a UDP-GalNAc:Polypeptide N-Acetylgalactosaminyltransferase That Displays Glycopeptide N-Acetylgalactosaminyltransferase Activity." J. Biol. Chem., 274(39): 27867-27874 (1999).
Tenno et al., "The Lectin Domain of UDP-GalNAc:Polypeptide N-Acetylgalactosaminyltransferase 1 is involved in O-Glycosylation of a Polypeptide with Multiple Acceptor Sites." 2002, Biochemistry 29(37):8509-8517.
Tenno et al., "The Lectin Domain of UDP-GalNAc: Polypeptide N-acetylgalactosaminyltransferase 1 Is Involved in O-Glycosylation of a Polypeptide With Multiple Acceptor Sites," 2002, Journal of Biological Chemistry 277(49):47088-47096.
Thotakura et al., "[28] Enzymatic Deglcosylation of Gylcoproteins," 1987, Meth. Enzymol. 138:350-359.
Trottein et al., "Molecular cloning of a putative alpha3-fucosyltransferase from Schistosoma mansoni." Mol. Biochem. Parasitol., vol. 107(2), pp. 279-287 (2000).
Tsuboi et al., "6'-Sulfo Sialyl LEX But Not 6-Sulfo LEX Expressed on the Cell Surface Supports L-Selectin-Mediated Adhesion," Journal of Biological Chemistry, 1996, vol. 271, pp. 27213-27216.
Tsuboi et al., "Acquisition of P-selectin Binding Activity by en Bloc Transfer of Sulfo Le Trisaccharide to the Cell Surface: Comparison to a Sialyl Le Tetrasaccharide Transferred on the Cell Surface." 2000, Archives of Biochemistry and Biophysics 374(1):100-106.
Tsunoda et al., "Enhanced Antitumor Potency of Polyethylene Glycolylated Tumor Necrosis Factor-alpha: A Novel Polymer-Conjugation Technique with a Reversible Amino-Protective Reagent." J. Pharmacol. Exp. Ther., 209(1): 368-372 (1999).
Gross et al., "A Highly Sensitive Fluorometric Assay for Sialytransferase Activity Using CMP-9-Fluoresceinyl-NeuAc as Donor," Biochemistry, 1990, vol. 186, pp. 127-134.
Gross, 1992, "Fluorescent CMP-Sialic Acids as a Tool to Study the Specificity of the CMP-Sialic Acid Carrier and the Glycoconjugate Sialylation in Permeabilized Cells", European Journal of Biochemistry 203(1-2):269-275.
Hagen et al., 1999, "Characterization of a UDP-GalNAc:Polypeptide N-acetylgalactosaminyltransferase That Displays Glycopeptide N-acetylgalactosaminyltransferase Activity", Journal of Biological Chemistry 274:27867-27874.

Hagen et al., 1999, "Structure-Function Analysis of the UDP-N-Acetyl-D-Galactosamine: Polypeptide N-Acetylgalactosaminyltransferase", Journal of Biological Chemistry 274(10):6797-6803.
Hagen et al., "Cloning and Characterization of a Ninth Member of the UDP-GalNAc: Polypeptide N-Acetylgalactosaminyltransferase Fmaily, ppGANTASE-T9," 2001, Journal of Biological Chemistry 276(20):17395-17404.
Hall et al., 2001, "Immunotoxin Treatment of Brain Tumors", Methods in Molecular Biology 166:139-154.
Haneda et al., 1996, "Transglycosylation of Intact Sialo Complex-Type Oligosaccharides to the N-Acetylglucosamine Moieties of Glycopeptides by Mucor Hiemalis Endo-Beta-N-Acetylglucosamindase", Carbohydrate Research 292:61-70.
Hang et al., 2001, "Ketone Isosteres of 2-N-Acetamidosugars as Substrates for Metabolic Cell Surface Engineering", Journal of the American Chemistry Society 123(6):1242-1243.
Hansen et al., "Prediction of O-Glycosylation of Mammalian Proteins: Specificity Patterns of UDP-GalNAc: Polypeptide N-Acetylgalactosaminyltransferase", Biochem. J., vol. 308, pp. 801-813 (1995).
Haro et al., "Glycosylated Human Growth Hormone (HGH): A Novel 24 kDa HGH-N Variant", Biochem. Biophys. Res.Comm., vol. 228(2), pp. 549-556 (1996).
Harris, Milton J. (ed.), "Poly(Ethylene Glycol) Chemistry: Biotechnical and Biomedical Applications", Plenum Press, New York, pp. 347-370 (1992).
Harris et al. (eds.), "Poly(ethylene glycol): Chemistry and Biological Applications," ACS Symposium Series, vol. 680, American Chemical Society (1997)(includes 28 abtsracts listed below).
Harris et al., 1991, Abstracts of Papers—American Chemical Society V. 201, Apr, p. 64—Poly:154-155.
Harris et al., 2003, "Effect of Pegylation on Pharmaceuticals", Nature Reviews Drug Discovery 2(3):214-221.
Harris, Milton J., "Laboratory Synthesis of Polyethylene Glycol Derivatives," 1985, Macronol. Chem. Phys. C25(3):325-373.
Hassan et al., "The Lectin Domain of UDP-N-Acetyl-D-Galactosamine: Polypeptide N-Acetylgalactosaminyltransferase-T4 Directs Its Glycopeptide Specificities," 2000, Journal of Biological Chemistry 275(49):38197-38205.
Hassan et al., "Control of Mucin-Type O-Glycosylation: O-Glycan Occupancy Is Directed by Substrate Specificities of Polypeptide GalNAc-Transferases," Carbohydrates in Chemistry and Biology, Part II, vol. 3: 273-292 (2000).
Hayes et al., 1993, "The Biosynthesis of Oligosaccharides in Intact Golgi Preparations From Rat Liver", Journal of Biological Chemistry 268(22):16170-16178.
Hellstrom et al., 2001, "Development and Activities of the BR96-Doxorubicin Immunoconjugate" Methods in Molecular Biology 166:3-16.
Hermanson et al., 1992, Immobilized Affinity Ligand Techniques, Academic Press.
Hermanson et al., 1996, Bioconjugate Techniques, Academic Press, San Diego.
Hermentin et al., 1996, "The Hypothetical N-Glycan Charge: A Number That Characterizes Protein Glycosylation., It Cannot Be Considered a Special Technical Feature," Glycobiology 6(2):217-230.
Herscovics et al., "Glycoprotein Biosynthesis in Yeast," FASEB J., 7(6): 540-550 (1993).
Hills et al., 2002, "Control of Therapeutic Monoclonal Antibody Glycosylation Through the Addition of Sugar Media Components and In Vitro Remodeling", American Biotechnology Laboratory 20(11):30.
Hink et al., 1991, "Expression of Three Recombinant Proteins Using Baculovirus Vectors in 23 Insect Cell Lines", Biotechnology Progress 7(1):9-14.
Höglund, M., Glycosylated and Non-Glycosylated Recombinant Human Granulocyte Colony-Stimulating Factor (rhG-CSF)—What Is the Difference, Med. Oncol., vol. 15(4), pp. 229-233 (1998).
Hollister et al., 2001, "Engineering Lepidopteran Insect Cells for Sialoglycoprotein Production by Genetic Transformation With

(56) References Cited

OTHER PUBLICATIONS

Mammalian Beta1,4-Galactosyltransferase and Alpha2,6-Sialytransferase Genes", Glycobiology 11(1):1-19.
Hounsell et al., "O-Linked Protein Glycosylation Structure and Function," 1996, Glycoconj. J. 13(1):19-26.
Hu et al., "FGF-18, A Novel Member of the Fibroblast Growth Factor Family, Stimulates Hepatic and Intestinal Proliferation", Mol. Cell. Biol., vol. 18(10): pp. 6063-6074 (1998).
"Hydrophobic Interaction Chromatography: Principles and Methods" (Published by Amersham Pharmacia Biotech in the Year 2000, No Author Indicated; 104 Pages as Published).
Ichikawa et al., 1992, "Chemical-Enzymatic Synthesis and Conformational Analysis of Sialyl Lewis X and Derivatives", Journal of the American Chemical Society 114(24):9283-9298.
Ikonomou et al., 1991, "Design of an Efficient Medium for Insect Cell Growth and Recombinant Protein Production", In Vitro Cellular & Developmental Biology Animal 37(9):549-559.
Inlow et al., 1989, "Insect Cell Culture and Baculovirus Propagation in Protein-Free Medium", J. Tissue Culture Meth. 12(1):13-16.
Inoue et al., 1995, "The Production of Recombinant Human Erythropoietin", Biotechnology Annual Review 1:297-313.
Ito et al., 1993, "Synthesis of Bioactive Sialosides," Pure & Appl. Chem. 65(4):753-762.
Jackson et al., 1987, "Synthesis, Isolation, and Characterization of Conjugates of Ovalbumin With Monomethoxypolyethylene Glycol Using Cyanuric Chloride as the Coupling Agent", Analytical Biochemistry 165(1):114-127.
Jarvis et al., 1998, "Engineering N-Glycosylation Pathways in the Baculovirus-Insect Cell System", Current Opinions in Biotechnology 9(5):528-533.
Jezek et al., "Solid Phase Synthesis of Glycopeptide Dendrimers With Tn Antigenic Structure and Their Biological Activities", J. Peptide Sci., vol. 5, pp. 46-55 (1999).
Joppich et al., 1979, "Peptides Flanked by Two Polymer Chains, 1—Synthesis of Glycyl-L-Tryptophylglycine Substituted by Poly(Ethylene Oxide) at Both the Carboxy and the Amino End Groups", Makromol. Chem. 180:1381-1384.
Joshi et al., "ATP Synthase Complex From Bovine Heart Mitochondria," 1990, Journal of Biological Chemistry 265(24):14518-14525.
Jung et al., "Crosslinking of Platelet Glycoprotein IB by N-Succinimidyl(4-Azidophenyldithio)Propionate and 3.3'-Dithiobis (Sulfosuccinimidyl Propionate)," 1983, Biochem. Biophys. Acta 761(2):152-162.
Kajihara et al., 1999, "Enzymatic Synthesis of KDN Oligosaccharides by a Bacterial Alpha-(2 forward arrow 6)-Sialyltransferase", Carbohydrate Research 315(1-2):137-141.
Kalsner et al., 1995, "Insertion Into *Aspergillus nidulans* of Functional UDP-GlcNAc: Alpha3-D-mannoside Beta-1,2-N-Acetylglucosaminyl-Transferase 1, The Enzyme Catalysing the First Committed Step From Oligomannose to Hybrid and Complex N-Glycans", Glycoconj. J. 12(3):360-370.
Kaneko et al., "Assignment of the Human Alpha 1,3-Fucosyltransferase IX Gene (Fut9) to Chromosome Band 6Q16 by In Situ Hybridization", Cytogenet. Cell Genet., vol. 86(3-4), pp. 329-330 (1999).
Kaneko et al., "Alpha1,3-Fucoslytransferase IX (Fuc-TIX) Is Very Highly Conserved Between Human and Mouse; Molecular Cloning, Characterization and Tissue Distribution of Human Fuc-TIX", FEBS Lett., vol. 452(3), pp. 237-242 (1999).
Kasina et al., 1998 "Simplified Preformed Chelate Protein Radiolabeling With Technetium-99M Mercaptoacetamidoadipoylglycylglycine (N3S-Adipate)", Bioconjugate Chem. 9(1):108-117.
Katre et al., "Chemical Modification of Recombinant Interleukin 2 by Polyethylene Glycol Increases Its Potency in the Murine Meth a Sarcoma Model," 1987, PNAS 84(6):1487-1491.
Kawasaki et al., Application of Liquid Chromatography/Mass Spectrometry and Liquid Chromatography With Tandem Mass Spectrometry to the Analysis of the Site-Specific Carbohydrate Heterogeneity in Erythropoietn, Anal. Biochem., 285: 82-91 (2000).
Keana et al., "New Reagents for Photoaffinity Labeling: Synthesis and Photolysis of Functionalized Perfluorophenyl Azides," J. Org. Chem., 55(11): 3640-3647 (1990).
Keene et al., Expression of Biologically Active Human Follitropin in Chinese Hamster Ovary Cells, J. Biol. Chem., vol. 264(9), pp. 4769-4775 (1989).
Keppler et al., "Biochemical Engineering of the N-Acyl Side Chain of Sialic Acid: Biological Implications," 2001, Glycobiology 11(2):11R-18R.
Kimura et al., "Reconstitution of Functional L-Selectin Ligands on a Cultured Human Endothelial Cell Line by Cotransfection of Alpha1 forward arrow 3 Fucosyltransferase VII and Newly Cloned GlcNAcBeta:6-Sulfotransferase cDNA", Proc. Natl. Acad.Sci. USA, vol. 96(8), pp. 4530-4535 (1999).
Kisselev, "Polypeptide Release Factors in Prokaryotes and Eukaryotes: Same Function, Different Structure", Structure, vol. 10(1), pp. 8-9 (2002).
Kitamura et al., "Polyethylene Glycol Modification of the Monoclonal Antibody A7 Enhances Its Tumor Localization," 1990, Biochem. Biophys. Res. Commun. 171(3):1387-1394.
Kitamura et al., 1991, "Chemical Engineering of the Monoclonal Antibody A7 by Polyethylene Glycol for Targeting Cancer Chemotherapy", Cancer Res. 51(16):4310-4315.
Kobayashi et al., "Monoclonal Antibody-Dendrimer Conjugates Enable Radiolabeling of Antibody with Markedly High Specific Activity with Minimal Loss of Immunoreactivity", Eur. J. Nucl. Med., 27(9):1334-1339 (2000).
Kodama et al., "Synthesis of UDP-6-Deoxy- and -6-Fluoro-D-Galactoses and Their Enzymatic Glycosyl Transfer to Mono and Biantennary Carbohydrate Chains," 1993, Tetrahedron Letters 34(40):6419-6422.
Koeller et al., 2000, "Emerging Themes in Medicinal Glycoscience", Nature Biotechnology 18(8):835-841.
Koeller et al., 2001, "New Catalytic Synthetic Methods in Organic Chemistry That . . . ", Nature 409(6817):232-240.
Kogan, 1992, "The Synthesis of Substituted Methoxypoly(Ethyleneglycol) Derivatives Suitable for Selective Protein Modification," Synthetic Communications 22(16):2417-2424.
Koide et al., 1983, "Modification of Amino Groups in Porcine Pancreatic Elastase With Polyethylene Glycol in Relation to Binding Ability Towards Anti-Serum and to Enzymic Activity", Biochem. Biophys. Res. Commun. 111(2):659-667.
Kornfeld et al., "Assembly of Asparagine-Linked Oligosaccharides," Ann. Rev. Biochem., 54: 631-664 (1985).
Kreitmann, 2001, "Toxin-Labeled Monoclonal Antibodies." Current Pharmaceutical Biotechnology 2(4):313-325.
Kuhn et al., 1995, "Active Site and Oligosaccharide Recognition Residues of Peptide-N4-(N-acetyl-beta-D-glucosaminyl) asparagine Amidase F." Journal of Biological Chemistry 270(49):29493-29497.
Kukowska-Latallo et al., "A cloned human cDNA determines expression of a mouse stage-specific embryonic antigen and the Lewis blood group alpha(1,2/3,4)fucosyltransferase." Genes Dev., vol. 4(8), pp. 1288-1303 (1990).
Kukuruzinska et al., "Protein Glycosylation in Yeast: Transcript Heterogeneity of the ALG7 Gene," Proc. Natl. Acad. Sci. USA, 84(8): 2145-2149 (1987).
Lai et al., 1986, "Structural Characterization of Human Erythropoietin" Journal of Biological Chemistry 261(7):3116-3121.
Langer, Robert, "New Methods of Drug Delivery," Science, 249(4976): 1527-1533 (1990).
Lau et al., 1999, "Quantitative Competive Reverse Transcription-PCR as a Method to Evaluate Retrovirus Removal During Chromatography Procedures", Journal of Biotechnology 75(2-3):105-115.
Lee et al., 1989, "Efficient Coupling of Glycopeptides to Proteins with a Heterobifunctional Reagent." Biochemistry 28(4):1856-1861.
Lee-Huang et al., 1984, "Cloning and expression of human erythropoieetin cDNA in *Escherichia coli*." PNAS 81(9):2708-2712.

(56) References Cited

OTHER PUBLICATIONS

Legault et al., "Human alpha(1,3/1,4)-Fucosyltransferases Discriminate between Different Oligosaccharide Acceptor Aubstrates through a Discrete Peptide Fragment." J. Biol. Chem., 270(36): 20987-20996 (1995).
Leist et al., "Derivatives of Erythropoietin that are Tissue Protective but not Erythropoietic." Science, vol. 305, pp. 239-242 (2004).
Leiter et al., "Purification, cDNA cloning and Expression of GDP-L-Fuc:Asn-linked GlcNAc alpha1,3-Fucosyltransferase from Mung Beans." J. Biol. Chem., vol. 274(31), pp. 21830-21839 (1999).
Leung, S. 1995, "Engineering a Unique Glycosylation Site for Site-Specific Conjugation of Hapten to Antibody Fragments", Journal of Immunology 154(11):5919-5926.
Lewis et al., "Structure and Properties of Members of the hGH family: A Review." Endocr. J., vol. 47(Suppl.), S1-S8 (2000).
Li et al., 2002, "Transferrin/Transferrin Receptor-Mediated Drug Delivery." Medicinal Research Reviews 22(3):225-250.
Li et al., 2002, "The role of the transferrin-transferrin-receptor system in drug delivery and targeting." Trends in Pharmacological Sciences 23(5):206-209.
Licari et al., 1992, "Modeling the Population Dynamics of Baculovirus-Infected Insect Cells: Optimizing Infection Strategies for Enhanced Recombinant Protein Yields." Biotechnology and Bioengineering 39(4):432-441.
Licari et al., 1992, "Production of a Discrete, Heterogeneous Population of Beta-Galactosidase Polypeptides Using Baculovirus Expression Vectors." Biotechnology and Bioengineering 39(9):932-944.
Lin et al., "Cloning and Expression of the Human Erythropoietin Gene", Proc. Natl. Acad. Sci. USA, 82: 7580-7584 (1985).
Liu et al., 1996, "Chemo-Enzymatic Synthesis of GM3." Chem. Eur. J. 2(11):1359-1362.
Lönnberg, "Solid-Supported Synthesis of Glycocnjugates." Curr. Org. Synth., vol. 6(4), pp. 400-425 (2009).
Long et al., 2006, "Design of Homogeneous, Monopegylated Erythropoitin Analogs With Preserved In Vitro Bioactivity", Experimental Hematology 34(6):697-704.
Lord et al.,"Kinetics of Neutrophil Production in Normal and Neutropenic Animals during the Response to Filgrastim (r-metHu G-CSF) or Filgrastim SD/01 (PEG-r-metHu G-CSF)." 2001, Clin. Cancer Res. 7(7):2085-2090.
Lougheed et al., "Glycosyl Fluorides Can Function as Substrates for Nucleotide Phosphosugar-Dependent Glycosyltransferases," 1999, J. Biol. Chem. 274(53):37717-37722.
Luckow et al., "Baculovirus systems for the expression of human gene products." 1993, Curr. Opin. Biotechnol. 4(5):564-572.
Lund et al., "Oligosaccharide-protein interactions in IgG can Modulate recognition by Fcy receptors." 1995, FASEB J. 9(1):115-119.
Lund et al., "Multiple interactions of IgG with its core oligosaccharide can modulate recognition by complement and human FC gamma receptor I and influence the synthesis of its oligosaccharide chains." 1996, J. Immunol. 157(11):4963-4969.
Luo et al., "Spontaneous calcification of arteries and cartilage in mice lacking matrix GLA protein." Nature, 1997, vol. 386, pp. 78-81.
Mahal et al., "Engineering Chemical Reactivity on Cell Surfaces Through Oligosaccharide Biosynthesis." 1997, Science 276(5315):1125-1128.
Makino, Y. et al., "Structural Analysis of N-Linked Sugar Chains of Human Blood Clotting Factor IX," Journal of Biological Chemistry, 2000, vol. 128, pp. 175-180.
Malissard et al., "Expression of FUnctional Soluble Forms of Human Beta-1,4-Galactosyltransferase I, Alpha-2,6-Sialyltransferase, and alpha-1,3-Fucosyltransferase VI in the Methyltrophic Yeast *Pichia pastoris*." Biochem. Biophys. Res.Commun., vol. 267(1), pp. 169-173 (2000).
Manfioletti et al., "The Protein Encoded by a Growth Arrest-Specific Gene (gas6) is a New Member of the Vitamin K-Dependent Proteins Related to Protein S, a negative Coregulator in the Blood Coagulation Cascade." Molecular and Cellular Biology, 1993, vol. 13(8), pp. 4976-4985.

Maranga et al., "Virus-like Particle Production at Low Multiplicities of Infection With the Baculovirus Insect Cell System." 2003, Biotechnology and Bioengineering 84(2):245-253.
Maras et al., 2000, "Molecular Cloning and Enzymatic Characterization of a *Trichoderma reesei*, 2-alpha-D-mannosidase", J. Biotechnol. 77(2-3): 255-263.
Meynial-Salles et al., "In Vitro Glycosylation of Proteins: An Enzymatic Approach." 1996, J. Biotechnol. 46(1):1-14.
Miller et al., "Baculoviruses: high-level expression in insect cells." 1993, Curr. Opin. Genet. Dev. 3(1):97-101.
Min et al., "Site-directed Mutagenesis of Recombinant Equine Chorionic Gonadotropin/Luteinzing Hormone: Differential Role of Oligosaccharides in Luteinizing Hormore- and Follicle-Stimulating Hormone-like Activities." 1996, Endocr. J. 43(5): pp. 585-593.
Mistry et al.,"Therapeutic delivery of proteins to macrophages:implications for treatment of Gaucher's disease." 1996, Lancet 348(9041):1555-1559.
Tuddenham, Edward, "RNA as Drug and Antidote," 2002, Nature 419(6902):23-24.
Udenfriend et al., "How Glcosyl-Phosphatidylinositol-Anchored Membrane Proteins Are Made," 1995, Ann. Rev. Biochem. 64:563-591.
Ulloa-Aguirre et al., 1999, "Role of Glycosylation in Function of Follicle-Stimulating Hormone", Endocrine 11(3):205-215.
Uludag et al., "Targeting Systemically Administered Proteins to Bone by Bisphosphonate Conjugation." 2002, Biotechnol. Prog. 18(3):604-611.
Urdal et al., "Lymphokine Purification by Reversed-Phase High-Performance Liquid Chromatography." 1984, J. Chromatography 296:171-179.
Van Berkel et al., "Heterogeneity in utilization of N-glycosylation sites Asn624 and Asn138 in human lactoferrin: a study with glycosylation-site mutants." 1996, Biochem. J. 319(pt. 1):117-122.
Van Reis et al., "Industrial Scale Harvest of Proteins from Mammalian Cell Culture by Tangential Flow Filtration." Biotechnol. Bioeng., 38(4): 413-422 (1991).
Van Tetering et al., "Characterization of a core alpha1->3-fucosyltransferase from the snail *Lymnaea stagnalis* that is involved in the synthesis of complex-type N-glycans." FEBS Lett., vol. 461(3), pp. 311-314 (1999).
Veronese et al., "Surface Modification of Proteins: Activation of Monomethoxy-polyethylene Glcols by Phenylchloroformates and Modification of Ribonuclease and Superoxide Dismutase," 1985, Appl. Biochem. Biotech. 11(2):141-152.
Veronese, "Peptide and Protein PEGylation: a review of problems and solutions." 2001, Biomaterials 22(5):405-417.
Vitetta et al., "Considering Therapeutic Antibodies." Science, 313: 308-309 (2006).
Vocadlo et al., "Glycosiddase-Catalysed Oligosaccharide Synthesis" (2000), In Carbohydrate Chemistry and Biology, vol. 2, Chapter 29, pp. 723-844.
Vyas et al., "Ligand-Receptor-Mediated Drug Delivery: An Emerging Paradigm in Cellular Drug Targeting." 2001, Crit. Rev. Ther. Drug Carrier Syst. 18(1):1-76.
Wang et al., "Identification of a GDP-L-Fucose:polypeptide fucosyltransferase and enzymatic addition of O-linked fucose to EGF domains." Gycobiology, vol. 6(8), pp. 837-842 (1996).
Wang et al., "Novel *Helicobacter pylori* alpha1,2-fucosyltransferase, a key enzyme in the synthesis of Lewis antigens." Microbiol., vol. 145(Pt. 11), pp. 3245-3253 (1999).
Wang et al., "Chemoenzymatic Synthesis of a High-Mannose-Type N-Glycopeptide Analog With C-Glycosidic Liinkage." 1996, Tetrahedron Letters 37(12):1975-1978.
Wang et al., 1998, "Single-Chain Fv With Manifold N-Glycans as Bifunctional Scaffolds for Immunomolecules", Protein Engineering 11(12):1277-1283.
Wellhoner et al., "Uptake and Concentration of Bioactive Macromolecules by K562 Cells via the Transferrin Cycle Utilizing and Acid-labile Transferrin." 1991, J. Biol. Chem. 226(7):4309-4314.
Wells, 1990, "Additivity of Mutational Effects in Proteins," Biochemistry 29(37):8509-8517.
Weston et al., "Isolation of a Novel Human alpha(1,3)Fucosyltransferase Gene and Molecular Comparison to

(56) References Cited

OTHER PUBLICATIONS the Human Lewis Blood Group alpha(1,3/1,4)Fucosyltransferase Gene." J. Biol. Chem., vol. 267(6), pp. 4152-4160 (1992).

Weston et al., "Molecular Cloning of a Fourth Member of a Human alpha(1,3)Fucosyltransferase Gene Family." J. Biol. Chem., vol. 267(34), pp. 24575-24584 (1992).

White et al., "Purification and cDNA cloning of a Human UDP-N-acetyl-alpha-D-galactosamine:polypeptide N-Acetylgalactosaminyltransferase." J. Biol. Chem., 270(41): 24156-24165 (1995).

Wishart et al., "A Single Mutation Converts a Novel Phosphotyrosine Binding Domain into a Dual-specificity Phosphate." J. Biol. Chem., vol. 270(45), pp. 26782-26785 (1995).

Witkowski et al., "Conversion of a beta-ketoacyl Synthase to a Malonyl Decarboxylase by REplacement of the Active Site Cysteine with Glutamine." Biochemistry, vol. 38(36), pp. 11643-11650 (1999).

Witte et al., "Enzymatic Glycoprotein Synthesis: Preparation of Ribonuclease Glycoforms via Enzymatic Glycopeptide Condensation and Glycosylation." 1997, J. Am. Chem. Soc. 119(9):2114-2118.

Witte et al., :Monoclonal antibodies targeting the VEGF receptor-2 (Flk1/KDR) as an anti-angiogenic therapeutic strategy. Cancer and Metastasis Rev., 17: 155-161 (1998).

Woghiren et al., "Protected Thiol-Polyethylene Glycol: A New Activated Polymer for Reversible Protein Modification." 1993, Bioconjugate Chem. 4(5):314-318.

Wong et al., "Enzyme-Catalyzed Synthesis of N-Acetyllactosamine with in Situ Regeneration of Uridine 5'-Diphosphate Glucose and Uridine 5'-Diphosphate Galactose." 1982, Journal of Organic Chemistry 47 (27):5416-5418.

Wong et al., "Chemical Crosslinking and the Stabilization of Proteins and Enzymes," 1992, Enzyme Microb. Technol. 14(11):866-874.

Wong et al., "Low Multiplicity Infection of Insect Cells with a Recombinant Baculovirus: The Cell Yield Concept." 1996, Biotechnology and Bioengineering 49(6):659-666.

Woods et al., "Transferrin Receptors and Cation-independent mannose-6-phosphate receptors deliver their ligands to two distinct subpopulations of multivesicular endosomes." 1989, European Journal of Cell Biology 50(1):132-143.

Wright et al., "Effect of C2-Associated Carbohydrate Structure on Ig Effector Function: Studies with Chimeric Mouse-Human IgG1 Antibodies in Glycosylation Mutants of Chinese Hamster Ovary Cells." 1998, J. Immunology 160(7):3393-3402.

Wu et al., "Pharmacokinetics and Brain Uptake of Biotinylated Basic Fibroblast Growth Factor Conjugated to a Blood-Brain Barrier Drug Delivery System." 2002, J. Drug Targeting 10(3):239-245.

Xing et al., "Design of a transferrin-proteinase inhibitor conjugate to probe for active cysteine proteinases in endosomes." 1998, Biochem. J. 336(pt. 3):667-673.

Yamada et al., "Selective Modification of Aspartis Acid-101 in Lysozyme by Carbodiimide Reaction," Biochemistry, 20(17): 4836-4842 (1981).

Yamamoto et al., "Chemoenzymatic synthesis of a novel glycopeptide using a microbial endoglycosidase." 1998, Carbohydrate Res. 305(3-4):415-422.

Yarema et al., "Metabolic Delivery of Ketone Groups to Sialic Acid Residues." 1998, J. Biological Chemistry 273(47):31168-31179.

Yoshitake et al., "Nucleotide Sequence of the Gene for Human Factor IX (Antihemophilic Factor B)." 1985, Biochemistry 24(14):3736-3750.

Yoshida et al., "Expression and Characterization of rat UDP-N-acetylglucosamine: alpha-3-D-mannoside beta-1,2-N-acetylglucosaminytransferase I in *Saccharomyces cervisiae*." 1999, Glycobiology 9(1):53-58.

Younes et al., "Morphological Study of Biodegradable PEO/PLA Block Copolymers," J. Biomed. Mater. Res., 21(11): 1301-1316 (1987).

Zalipsky et al., "Preparation of Polyethylene Glycol Derivatives With Two Different Functional Groups at the Terminal", Polymer Reprints, vol. 27, pp. 1-2 (1986).

Zalipsky et al., "A Convenient General Method for Synthesis of Nalpha-Nomega-Dithiasuccinoyl (Dts) Amino Acids and Dipeptides: Application of Polyethylene Glycol as a Carrier for Functional Purification", Int'l Peptide Protein Res, vol. 30, pp. 740-783 (1987).

Zalipsky et al., "Use of Functionalized Poly(Ethylene Glycol)s for Modification of Polypeptides," (1992), Poly(Ethylene Glycol) Chemistry: Biotechnical and Biomedical Applications, Harris (ed), Chapter 21, pp. 347-370 (Plenum Press, New York, 1992).

Zalipsky, Samuel, "Functionalized Poly(Ethylene Glycol) for Preparation of Biologically Relevant Conjugates," 1995, Bioconjugate Chem. 6(2)150-165.

Zarling et al., "Mapping of Lymphocyte Surface Polypeptide Antigens by Chemical Crosslinking With BSOCOES," J. Immunol., 124(2): 913-920 (1980).

Zhang et al., "Stable Expression of Human a-2,6-Sialyltransferase in Chinese Hamster Ovary Cells: Functional Consequences for Human Erythropoletin Expression and Bioactivity." Biochim. Biophys. Acta, vol. 1425, pp. 441-452 (1998).

Zheng et al., "Optimized Production of Recombinant Bluetongue Core-Like Particles Produced by the Baculovirus Expression System." 1999, Biotechnology and Bioengineering 65(5):600-604.

Zhou et al., "Lipooligosaccharide biosynthesis in *Neisseria gonorrhoeae*: cloning, identification and characterization of the alpha1,5 heptosyltransferase I gene (rfaC)." 1994, Mol. Microbiol. 14(4):609-618.

Declaration of Dr. Peter Turecek, Declaration of Dr Peter Turecek. Inc.'s 2000 Catalogue, "Shearwater Polymers".

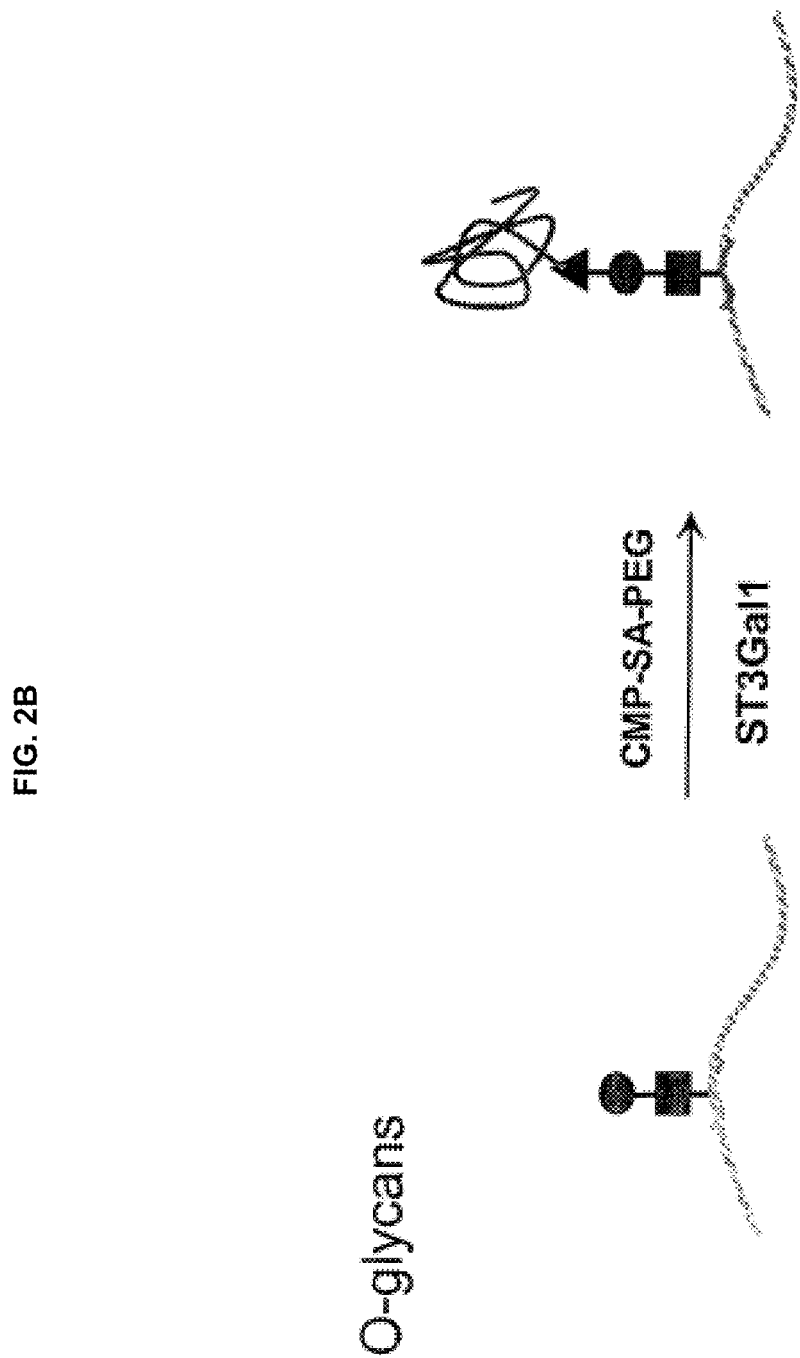

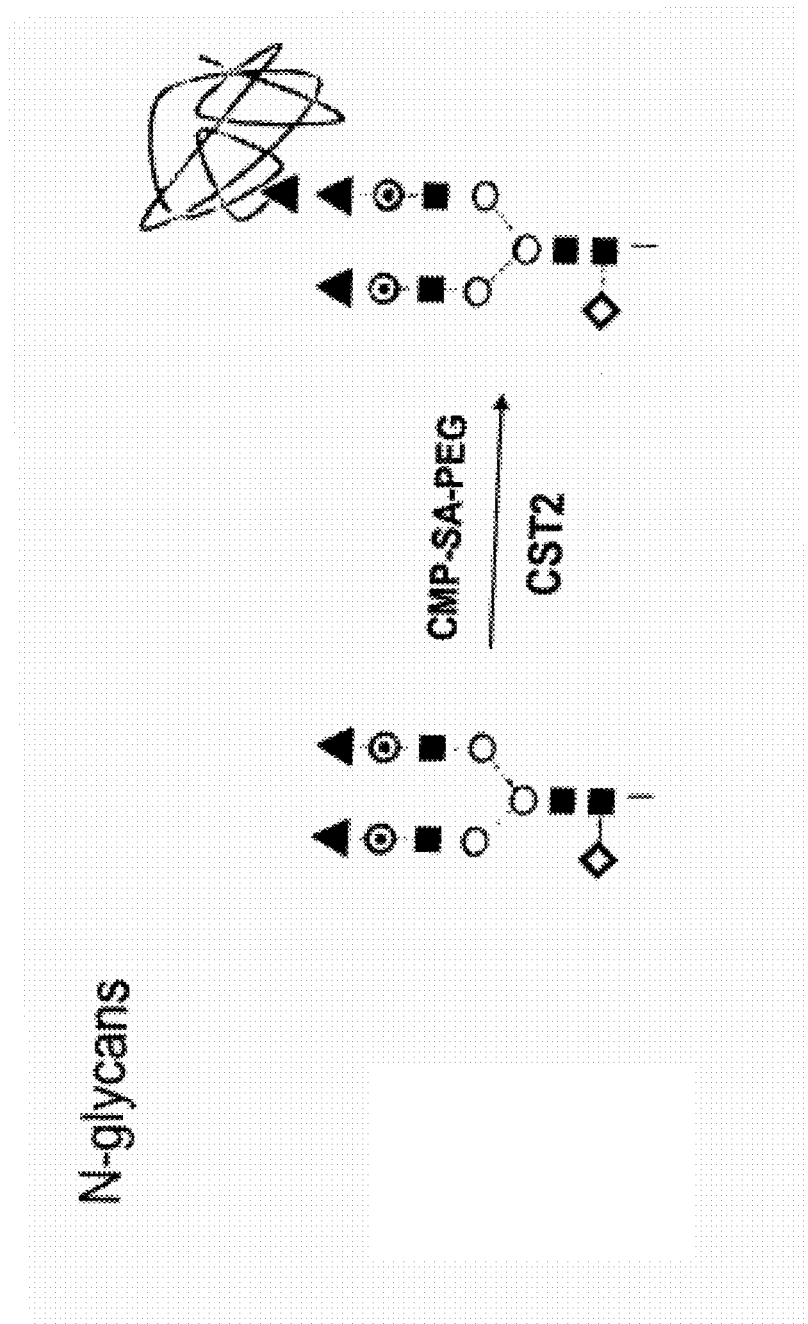

FIG. 4

| Enzyme | Specificity and Linkage | Reaction Conditions | PEG Incorporation (size) | Clotting Activity (Chromogenic Assay) |
|---|---|---|---|---|
| Factor IX (unmodified) | NA | NA | >90% sialylation | 110-139% |
| ST3Gal3 | N-linked glycans | CMP-SA | None. (incorporated 2-3% SA) | Full Activity |
| ST3Gal3 | N-linked glycans | 1. Sialidase 2. CMP-SA-PEG (1 & 10KDa) | (1 K); 6-8 PEG (10 K); 5-7 PEG | PEG (1 KDa); 52%. PEG (10 KDa); 54%. |
| ST3Gal3 | N-linked glycans | CMP-SA-PEG (10 KDa); no sialidase. | 1-6 PEG (10 KDa) | 1-2 PEG's (27 hrs); 164% ~3 PEG's (119 or 27 hrs); 97% 4-5 PEG's (119 hrs) |
| CST-II (Campylobacter) | | CMP-SA-PEG (20 KDa); no sialidase | 2-3 PEG (20 KDa) | 96% |

FIG. 5

```
YNSGKLEEFVQGNLERECMEEKCSFEEAREVFENTERTTEFWKQYVDGDQ
CESNPCLNGGSCKDDINSYECWCPFGFEGKNCELDVTCNIKNGRCEQFCK
NSADNKVVCSCTEGYRLAENQKSCEPAVPFPCGRVSVSQTSKLTRAEAVFP
DVDYVNSTEAETILDNITQSTQSFNDFTRVVGGEDAKPGQFPWQVVLNGKV
DAFCGGSIVNEKWIVTAAHCVETGVKITVVAGEHNIEETEHTEQKRNVIRIIPH
HNYNAAINKYNHDIALLELDEPLVLNSYVTPICIADKEYTNIFLKFGSGYVSGWGRVFHK
GRSALVLQYLRVPLVDRATCLRSTKFTIYNNMFCAGFHEGGRDSCQGDSGGPHVTEVE
GTSFLTGIISWGEECAMKGKYGIYTKVSRYVNWIKEKTKLT
```

FIG. 9A

| Protein | Organism | EC# | GenBank / GenPept | | SwissProt | PDB / 3D |
|---|---|---|---|---|---|---|
| At1g08280 | Arabidopsis thaliana | n.d. | AC011438 BT004583 NC_003070 | AAF18241.1 AAO42829.1 NP_172305.1 | Q84W00 Q9SGD2 | |
| At1g08660/F22O13.14 | Arabidopsis thaliana | n.d. | AC003981 AY084135 AY124807 NC_003070 NM_180609 | AAF96778.1 AAL36042.1 AAM70516.1 NP_172342.1 NP_850940.1 | Q8VZJ0 Q9FRR9 | |
| At3g48820/T21J18_90 | Arabidopsis thaliana | n.d. | AY080569 AY133816 AL132963 NM_114741 | AAL85988.1 AAM91750.1 CAB87910.1 NP_190451.1 | Q8RY00 Q9M301 | |
| α-2,3-sialyltransferase (ST3GAL-IV) | Bos taurus | n.d. | AJ584673 | CAE48298.1 | | |
| α-2,3-sialyltransferase (St3Gal-V) | Bos taurus | n.d. | AJ585788 | CAE54392.1 | | |
| α-2,6-sialyltransferase (Siat7b) | Bos taurus | n.d. | AJ620851 | CAF05850.1 | | |
| α-2,8-sialyltransferase (SIAT8A) | Bos taurus | 2.4.99.8 | AJ699418 | CAG27886.1 | | |
| α-2,8-sialyltransferase (Siat8D) | Bos taurus | n.d. | AJ699421 | CAG27883.1 | | |
| α-2,8-sialyltransferase ST8Sia-III (Siat8C) | Bos taurus | n.d. | AJ704583 | CAG28696.1 | | |
| CMP α-2,6-sialyltransferase (ST6Gal I) | Bos taurus | 2.4.99.1 | Y15111 NM_177517 | CAA75385.1 NP_803483.1 | O18974 | |
| sialyltransferase 8 (fragment) | Bos taurus | n.d. | AF450088 | AAL47018.1 | Q8WN13 | |
| sialyltransferase ST3Gal-II (Siat4B) | Bos taurus | n.d. | AJ748841 | CAG44450.1 | | |
| sialyltransferase ST3Gal-III (Siat6) | Bos taurus | n.d. | AJ748842 | CAG44451.1 | | |
| sialyltransferase ST3Gal-VI (Siat10) | Bos taurus | n.d. | AJ748843 | CAG44452.1 | | |
| ST3Gal I | Bos taurus | n.d. | AJ305086 | CAC24698.1 | Q9BEG4 | |
| St6GalNAc-VI | Bos taurus | n.d. | AJ620949 | CAF06586.1 | | |
| CDS4 | Branchiostoma floridae | n.d. | AF391289 | AAM18873.1 | Q8T771 | |
| polysialyltransferase (PST) (fragment) ST8Sia IV | Cercopithecus aethiops | 2.4.99.- | AF210729 | AAF17105.1 | Q9TT09 | |
| polysialyltransferase (STX) (fragment) ST8Sia II | Cercopithecus aethiops | 2.4.99.- | AF210318 | AAF17104.1 | Q9TT10 | |
| α-2,3-sialyltransferase ST3Gal I (Siat4) | Ciona intestinalis | n.d. | AJ626815 | CAF25173.1 | | |
| α-2,3-sialyltransferase ST3Gal I (Siat4) | Ciona savignyi | n.d. | AJ626814 | CAF25172.1 | | |
| α-2,8-polysialyltransferase ST8Sia IV | Cricetulus griseus | 2.4.99.- | Z46801 | AAE29634 CAA86822.1 | Q64689 | |
| Gal β-1,3/4-GlcNAc α-2,3-sialyltransferase St3Gal I | Cricetulus griseus | n.d. | AY266675 | AAP22942.1 | Q80WL0 | |
| Gal β-1,3/4-GlcNAc α-2,3-sialyltransferase St3Gal I (fragment) | Cricetulus griseus | n.d. | AY266676 | AAP22943.1 | Q80WK9 | |
| α-2,3-sialyltransferase ST3Gal I (Siat4) | Danio rerio | n.d. | AJ783740 | CAH04017.1 | | |
| α-2,3-sialyltransferase ST3Gal II (Siat5) | Danio rerio | n.d. | AJ783741 | CAH04018.1 | | |

FIG. 9B

| Protein | Organism | EC# | GenBank / GenPept | | SwissProt | PDB / 3D |
|---|---|---|---|---|---|---|
| α-2,3-sialyltransferase ST3Gal III (Siat6) | Danio rerio | n.d. | AJ626821 | CAF25179.1 | | |
| α-2,3-sialyltransferase ST3Gal IV (Siat4c) | Danio rerio | n.d. | AJ744809 | CAG32845.1 | | |
| α-2,3-sialyltransferase ST3Gal V-r (Siat5-related) | Danio rerio | n.d. | AJ783742 | CAH04019.1 | | |
| α-2,6-sialyltransferase ST6Gal I (Siat1) | Danio rerio | n.d. | AJ744801 | CAG32837.1 | | |
| α-2,6-sialyltransferase ST6GalNAc II (Siat7B) | Danio rerio | n.d. | AJ634459 | CAG25680.1 | | |
| α-2,6-sialyltransferase ST6GalNAc V (Siat7E) (fragment) | Danio rerio | n.d. | AJ646874 | CAG26703.1 | | |
| α-2,6-sialyltransferase ST6GalNAc VI (Siat7F) (fragment) | Danio rerio | n.d. | AJ646883 | CAG26712.1 | | |
| α-2,8-sialyltransferase ST8Sia I (Siat 8A) (fragment) | Danio rerio | n.d. | AJ715535 | CAG29374.1 | | |
| α-2,8-sialyltransferase ST8Sia III (Siat 8C) (fragment) | Danio rerio | n.d. | AJ715543 | CAG29382.1 | | |
| α-2,8-sialyltransferase ST8Sia IV (Siat 8D) (fragment) | Danio rerio | n.d. | AJ715545 | CAG29384.1 | | |
| α-2,8-sialyltransferase ST8Sia V (Siat 8E) (fragment) | Danio rerio | n.d. | AJ715546 | CAG29385.1 | | |
| α-2,8-sialyltransferase ST8Sia VI (Siat 8F) (fragment) | Danio rerio | n.d. | AJ715551 | CAG29390.1 | | |
| β-galactosamide α-2,6-sialyltransferase II (ST6Gal II) | Danio rerio | n.d. | AJ627627 | CAF25495.1 | | |
| N-glycan α-2,8-sialyltransferase | Danio rerio | n.d. | BC050483 AY055462 NM_153662 | AAH50483.1 AAL17875.1 NP_705948.1 | Q7ZU51 Q8QH83 | |
| ST3Gal III-related (siat6r) | Danio rerio | n.d. | BC053179 AJ626820 NM_200355 | AAH53179.1 CAF25178.1 NP_956649.1 | Q7T3B9 | |
| St3Gal-V | Danio rerio | n.d. | AJ619960 | CAF04061.1 | | |
| st8GalNAc-VI | Danio rerio | n.d. | BC060932 AJ623947 | AAH60932.1 CAF06584.1 | | |
| α-2,6-sialyltransferase (CG4871) ST6Gal I | Drosophila melanogaster | 2.4.99.1 | AE003465 AF218237 AF397532 AE003465 NM_079129 NM_166684 | AAF47256.1 AAG13183.1 AAK92126.1 AAM70791.1 NP_523863.1 NP_728474.1 | Q9GU23 Q9W121 | |
| α-2,3-sialyltransferase (ST3Gal-VI) | Gallus gallus | n.d. | AJ585767 AJ627204 | CAE51391.1 CAF25503.1 | | |
| α-2,3-sialyltransferase ST3Gal I | Gallus gallus | 2.4.99.4 | X80503 NM_205217 | CAA56666.1 NP_990548.1 | Q11200 | |
| α-2,3-sialyltransferase ST3Gal IV (fragment) | Gallus gallus | 2.4.99.- | AF035250 | AAC14163.1 | O73724 | |
| α-2,3-sialyltransferase (ST3GAL-II) | Gallus gallus | n.d. | AJ585761 | CAE51385.2 | | |
| α-2,6-sialyltransferase (Siat7b) | Gallus gallus | n.d. | AJ620653 | CAF05852.1 | | |
| α-2,6-sialyltransferase ST6Gal I | Gallus gallus | 2.4.99.1 | X75558 NM_205241 | CAA53235.1 NP_990572.1 | Q92182 | |
| α-2,6-sialyltransferase | Gallus gallus | 2.4.99.3 | - | AAE68028.1 | Q92183 | |

FIG. 9C

| Protein | Organism | EC# | GenBank / GenPept | | SwissProt | PDB / 3D |
|---|---|---|---|---|---|---|
| ST6GalNAc I | | | K74946 NM_205240 | AAE68029.1 CAA52962.1 NP_990571.1 | | |
| α-2,6-sialyltransferase ST6GalNAc II | Gallus gallus | 2.4.99.- | X77775 NM_205233 | AAE68030.1 CAA54813.1 NP_990564.1 | Q92184 | |
| α-2,6-sialyltransferase ST6GalNAc III (SIAT7C) (fragment) | Gallus gallus | n.d. | AJ634455 | CAG25677.1 | | |
| α-2,6-sialyltransferase ST6GalNAc V (SIAT7E) (fragment) | Gallus gallus | n.d. | AJ646877 | CAG26706.1 | | |
| α-2,8-sialyltransferase (GD3 Synthase) ST8Sia I | Gallus gallus | 2.4.99.- | U73176 | AAC38888.1 | P79783 | |
| α-2,8-sialyltransferase (SIAT8B) | Gallus gallus | n.d. | AJ699419 | CAG27881.1 | | |
| α-2,8-sialyltransferase (SIAT8C) | Gallus gallus | n.d. | AJ699420 | CAG27882.1 | | |
| α-2,8-sialyltransferase (SIAT8F) | Gallus gallus | n.d. | AJ699424 | CAG27886.1 | | |
| α-2,8-sialyltransferase ST8Sia V (SIAT8C) | Gallus gallus | n.d. | AJ704564 | CAG28697.1 | | |
| β-galactosamide α-2,8-sialyltransferase II (ST8Gal II) | Gallus gallus | n.d. | AJ627829 | CAF29497.1 | | |
| GM3 synthase (SIAT9) | Gallus gallus | 2.4.99.9 | AY515255 | AAS83519.1 | | |
| polysialyltransferase ST8Sia IV | Gallus gallus | 2.4.99.- | AF008194 | AAB95120.1 | O42399 | |
| α-2,3-sialyltransferase ST3Gal I | Homo sapiens | 2.4.99.4 | L29555 AF059321 L13972 AF155238 AF156191 BC018357 NM_003033 NM_173344 | AAA36812.1 AAC17874.1 AAC37574.1 AAD32238.1 AAG29876.1 AAH18357.1 NP_003024.1 NP_775479.1 | Q11201 O60677 Q9UN51 | |
| α-2,3-sialyltransferase ST3Gal II | Homo sapiens | 2.4.99.4 | U63090 BC036777 X96667 NM_006927 | AAB40389.1 AAH36777.1 CAA65447.1 NP_006918.1 | Q16842 O00654 | |
| α-2,3-sialyltransferase ST3Gal III (SiaT6) | Homo sapiens | 2.4.99.6 | L23768 BC050380 AF425851 AF425852 AF425853 AF425854 AF425855 AF425856 AF425857 AF425858 AF425859 AF425860 AF425861 AF425862 AF425863 AF425864 AF425865 AF425866 AF425867 AY187992 AY187993 AY187994 | AAA35778.1 AAH50380.1 AAO13859.1 AAO13860.1 AAO13861.1 AAO13862.1 AAO13863.1 AAO13864.1 AAO13865.1 AAO13866.1 AAO13867.1 AAO13868.1 AAO13869.1 AAO13870.1 AAO13871.1 AAO13872.1 AAO13873.1 AAO13874.1 AAO13875.1 AAO38806.1 AAO38807.1 AAO38808.1 | Q11203 Q86UR6 Q86UR7 Q86UR8 Q86UR9 Q86US0 Q86US1 Q86US2 Q8IX43 Q8IX44 Q8IX45 Q8IX46 Q8IX47 Q8IX48 Q8IX49 Q8IX50 Q8IX51 Q8IX52 Q8IX53 Q8IX54 Q8IX55 Q8IX56 | |

FIG. 9D

| Protein | Organism | EC# | GenBank / GenPept | | SwissProt | PDB / 3D |
|---|---|---|---|---|---|---|
| | | | AY167995 | AAO38809.1 | Q8IX57 | |
| | | | AY167996 | AAO38810.1 | Q8IX58 | |
| | | | AY167997 | AAO38811.1 | | |
| | | | AY167998 | AAO38812.1 | | |
| | | | NM_006279 | NP_006270.1 | | |
| | | | NM_174964 | NP_777624.1 | | |
| | | | NM_174965 | NP_777625.1 | | |
| | | | NM_174966 | NP_777626.1 | | |
| | | | NM_174967 | NP_777627.1 | | |
| | | | NM_174969 | NP_777629.1 | | |
| | | | NM_174970 | NP_777630.1 | | |
| | | | NM_174972 | NP_777632.1 | | |
| α-2,3-sialyltransferase ST3Gal IV | Homo sapiens | 2.4.99.- | L23767 | AAA16460.1 | Q11206 | |
| | | | AF035249 | AAC14162.1 | O60497 | |
| | | | BC010645 | AAH10645.1 | Q96QQ9 | |
| | | | AY040326 | AAK93793.1 | Q8N6A6 | |
| | | | AF518602 | AAM66431.1 | Q8N6A7 | |
| | | | AF518603 | AAM66432.1 | Q8NFD3 | |
| | | | AF518604 | AAM66433.1 | Q8NFG7 | |
| | | | AF525884 | AAM81379.1 | | |
| | | | X74570 | CAA52662.1 | | |
| | | | CR456858 | CAG33139.1 | | |
| | | | NM_006278 | NP_006269.1 | | |
| α-2,3-sialyltransferase ST3Gal VI | Homo sapiens | 2.4.99.4 | AF119391 | AAD38131.1 | Q9Y274 | |
| | | | BC023312 | AAH23312.1 | | |
| | | | AB022918 | BAA77609.1 | | |
| | | | AX877826 | CAE89695.1 | | |
| | | | AX886023 | CAF00161.1 | | |
| | | | NM_006100 | NP_006091.1 | | |
| α-2,6-sialyltransferase (ST6Gal II ; KIAA1877) | Homo sapiens | n.d. | BC008680 | AAH08680.1 | Q96Y44 | |
| | | | AB059780 | BAB47586.1 | Q8IUJ7 | |
| | | | AB059555 | BAC24793.1 | Q96HE4 | |
| | | | AJ512141 | CAD54408.1 | Q96JF9 | |
| | | | AX795193 | CAE48260.1 | | |
| | | | AX795193 | CAE48261.1 | | |
| | | | NM_032528 | NP_115917.1 | | |
| α-2,6-sialyltransferase (ST6GALNAC III) | Homo sapiens | n.d. | BC059363 | AAH59363.1 | Q8N259 | |
| | | | AY358540 | AAQ88904.1 | Q8NDV1 | |
| | | | AK091215 | BAC03611.1 | | |
| | | | AJ507291 | CAD45371.1 | | |
| | | | NM_152996 | NP_694541.1 | | |
| α-2,6-sialyltransferase (ST6GalNAc V) | Homo sapiens | n.d. | BC031201 | AAH31201.1 | Q9BVH7 | |
| | | | AK056241 | BAB71127.1 | | |
| | | | AL035409 | CAB72344.1 | | |
| | | | AJ507292 | CAD45372.1 | | |
| | | | NM_030965 | NP_112227.1 | | |
| α-2,6-sialyltransferase (SThM) ST6GalNAc II | Homo sapiens | 2.4.99.- | U14550 | AAA52228.1 | Q9UJ37 | |
| | | | BC043455 | AAH43455.1 | Q12971 | |
| | | | AJ251053 | CAB61404.1 | | |
| | | | NM_006456 | NP_006447.1 | | |
| α-2,6-sialyltransferase ST6Gal I | Homo sapiens | 2.4.99.1 | BC031476 | AAH31476.1 | P15907 | |
| | | | BC040009 | AAH40009.1 | | |
| | | | A17362 | CAA81327.1 | | |
| | | | A23699 | CAA01686.1 | | |
| | | | X17247 | CAA35111.1 | | |
| | | | X54363 | CAA38246.1 | | |
| | | | X62822 | CAA44634.1 | | |
| | | | NM_003032 | NP_003023.1 | | |
| | | | NM_173216 | NP_775323.1 | | |
| α-2,6-sialyltransferase ST6GalNAc I | Homo sapiens | 2.4.99.3 | BC022462 | AAH22462.1 | Q9TBJ6 | |
| | | | AY098001 | AAM22830.1 | Q9NSC7 | |
| | | | AY358918 | AAQ89277.1 | Q9NXQ7 | |
| | | | AK000113 | BAA90953.1 | | |
| | | | Y11339 | CAA72179.2 | | |

FIG. 9E

| Protein | Organism | EC# | GenBank / GenPept | | SwissProt | PDB / 3D |
|---|---|---|---|---|---|---|
| | | | NM_018414 | NP_060884.1 | | |
| α-2,8-polysialyltransferase ST8Sia IV | Homo sapiens | 2.4.99.- | L41680 BC037866 BC053657 NM_005668 | AAC41775.1 AAH37866.1 AAH53657.1 NP_005659.1 | Q8N1F4 Q92187 Q92693 | |
| α-2,8-sialyltransferase (GD3 synthase) ST8Sia I | Homo sapiens | 2.4.99.8 | L32867 L43494 BC048158 - AY589975 D26360 X77922 NM_003034 | AAA63366.1 AAC37586.1 AAH46158.1 AAQ53140.1 AAS75783.1 BAA05391.1 CAA54801.1 NP_003025.1 | Q96X71 Q92185 Q93084 | |
| α-2,8-sialyltransferase ST8Sia II | Homo sapiens | 2.4.99.- | L29556 U82762 U33551 BC068584 NM_006011 | AAA36813.1 AAB51242.1 AAC24458.1 AAH68584.1 NP_006002.1 | Q92186 Q92478 Q92748 | |
| α-2,8-sialyltransferase ST8Sia III | Homo sapiens | 2.4.99.- | AF004668 AF033092 NM_015879 | AAB87642.1 AAC15901.2 NP_056963.1 | O43173 Q9NS41 | |
| α-2,8-sialyltransferase ST8Sia V | Homo sapiens | 2.4.99.- | U91641 CR457037 NM_013305 | AAC51727.1 CAG33318.1 NP_037437.1 | O15466 | |
| ENSP00000020221 (fragment) | | n.d. | AC023295 | - | | |
| lactosylceramide α-2,3-sialyltransferase (ST3Gal V) | Homo sapiens | 2.4.99.9 | AF105026 AF119415 BC065636 AY152815 AAP65066 AY359105 AB018356 AX676536 NM_003896 | AAD14634.1 AAF66146.1 AAH65936.1 AAQ18865.1 AAP65066.1 AAQ89463.1 BAA33850.1 CAE59320.1 NP_003887.2 | Q9UNP4 O94902 | |
| N-acetylgalactosaminide α-2,6-sialyltransferase (ST6GalNAc VI) | Homo sapiens | 2.4.99.- | BC008564 BC007832 BC015299 AY358872 AB035173 AK023900 AJ507293 AX880950 CR457318 NM_013443 | AAP36564.1 AAH07832.1 AAH15299.1 AAQ89035.1 BAA87035.1 BAB14715.1 CAD45373.1 CAE91145.1 CAG33599.1 NP_038471.2 | Q969X2 Q9H6A2 Q9ULB8 | |
| N-acetylgalactosaminide α-2,6-sialyltransferase IV (ST6GalNAc IV) | Homo sapiens | 2.4.99.- | AF127142 BC036725 - AB035172 AK000800 Y17461 AJ271734 AX061820 AX068265 AX969252 NM_014403 NM_175039 | AAF30102.1 AAH36725.1 AAP63349.1 BAA87034.1 BAA91281.1 CAB44354.1 CAC07404.1 CAC24991.1 CAC27252.1 CAF14360.1 NP_055218.3 NP_778204.1 | Q9H4F1 Q9NWU6 Q9UKU1 Q9ULB9 Q9Y393 Q9Y394 | |
| ST8SiA-VI (fragment) | Homo sapiens | n.d. | AJ621563 XM_291725 | CAF21722.1 XP_291725.2 | | |
| unnamed protein product | Homo sapiens | n.d. | AK021929 AX881896 | BAB13940.1 CAE91353.1 | Q9HAA9 | |
| Gal β-1,3/4-GlcNAc α- | Mesocricetus | 2.4.99.6 | AJ245699 | CAB53394.1 | Q9QXF6 | |

FIG. 9F

| Protein | | Organism | EC# | GenBank / GenPept | | SwissProt | PDB / 3D |
|---|---|---|---|---|---|---|---|
| 2,3-sialyltransferase (ST3Gal III) | | auratus | | | | | |
| Galβ-1,3/4-GlcNAc α-2,3-sialyltransferase (ST3Gal IV) | | Mesocricetus auratus | 2.4.99.6 | AJ245700 | CAB53395.1 | Q9QXF5 | |
| GD3 synthase (fragment) ST8Sia I | | Mesocricetus auratus | n.d. | AF141857 | AAD33879.1 | Q9WUL1 | |
| polysialyltransferase (ST8Sia IV) | | Mesocricetus auratus | 2.4.99.- | AJ245701 | CAB53396.1 | Q9QXF4 | |
| α-2,3-sialyltransferase ST3Gal I | St3gal1 | Mus musculus | 2.4.99.4 | AF214328 AK031344 AK079469 X73523 NM_009177 | AAF80973.1 BAC27356.1 BAC37290.1 CAA51919.1 NP_033203.1 | P54751 Q11202 Q9JL30 | |
| α-2,3-sialyltransferase ST3Gal II | St3gal2 | Mus musculus | 2.4.99.4 | BC015254 BC066064 AK034554 AK034863 AK053827 X76989 NM_009179 NM_173046 | AAH15264.1 AAH66064.1 BAC28752.1 BAC28859.1 BAC35543.1 CAA54294.1 NP_033205.1 NP_835149.1 | Q11204 Q8BPL3 Q8BSA0 Q8BSE8 Q91WH8 | |
| α-2,3-sialyltransferase ST3Gal III | St3gal3 | Mus musculus | 2.4.99.- | BC008710 AK005053 AK013018 X84234 NM_009176 | AAH08710.1 BAB23779.1 BAB28598.1 CAA58013.1 NP_033202.2 | P97325 Q922X5 Q9CZ48 Q9DBB6 | |
| α-2,3-sialyltransferase ST3Gal IV | St3gal4 | Mus musculus | 2.4.99.4 | BC011121 BC050773 D28941 AK008543 AB061305 X95809 NM_009178 | AAH11121.1 AAH58773.1 BAA08088.1 BAB25732.1 BAB47508.1 CAA65076.1 NP_033204.2 | P97354 Q61325 Q91Y74 Q921R5 Q9CVE6 | |
| α-2,3-sialyltransferase ST3Gal VI | St3gal6 | Mus musculus | 2.4.99.4 | AF119390 BC052338 AB063326 AK033562 AK041173 NM_018784 | AAD39130.1 AAH52338.1 BAB79494.1 BAC28360.1 BAC30851.1 NP_061254 | Q80UR7 Q8BLV1 Q8VIB3 Q9WVG2 | |
| α-2,6-sialyltransferase ST6GalNAc II | St6galnac2 | Mus musculus | 2.4.99.- | NM_009180 BC018208 AB027198 AK004613 X83999 X94006 NM_009180 | 6677963 AAH18208.1 BAB00637.1 BAB23416.1 CAA63821.1 CAA63822.1 NP_033306.2 | P70277 Q9DC24 Q9JJM5 | |
| α-2,6-sialyltransferase ST6Gal I | St6gal1 | Mus musculus | 2.4.99.1 | - BC027833 D16106 AK034768 AK054124 NM_145933 | AAE68031.1 AAH27833.1 BAA03680.1 BAC28829.1 BAC38120.1 NP_666045.1 | Q64685 Q8BM62 Q9X1L1 | |
| α-2,6-sialyltransferase ST6Gal II | St6gal2 | Mus musculus | n.d. | AK082566 AB095023 AK129462 NM_172829 | BAC38534.1 BAC87752.1 BAC98272.1 NP_766417.1 | Q8BUU4 | |
| α-2,6-sialyltransferase ST6GalNAc I | St6galnac1 | Mus musculus | 2.4.99.3 | Y11274 NM_011371 | CAA72137.1 NP_035501.1 | Q9QZ39 Q9JJP5 | |
| α-2,6-sialyltransferase ST6GalNAc III | St6galnac3 | Mus musculus | n.d. | BC058387 AK034604 Y11342 Y11343 | AAH58387.1 BAC28836.1 CAA72181.2 CAB95031.1 | Q9WUV2 Q9JHP5 | |

FIG. 9G

| Protein | Organism | | EC# | GenBank / GenPept | | SwissProt | PDB / 3D |
|---|---|---|---|---|---|---|---|
| α-2,6-sialyltransferase ST6GalNAc IV | St6galnac4 | Mus musculus | 2.4.99.7 | NM_011372 BC050451 AK085730 AJ007319 Y15779 Y15780 Y19055 Y19057 NM_011373 | NP_035502 AAH58451.1 BAC39523.1 CAA07446.1 CAB43507.1 CAB43514.1 CAB83946.1 CAB83948.1 NP_035503.1 | Q8C3J2 Q9JHP2 Q9R2B6 O88725 Q9JHP0 Q8QJP9 Q9R2B5 | |
| α-2,8-sialyltransferase (GD3 synthase) ST8Sia I | St8sia1 | Mus musculus | 2.4.99.8 | L38677 BC024821 AK046188 AK052444 X84235 AJ491102 NM_011374 | AAA91869.1 AAH24821.1 BAC32825.1 BAC34094.1 CAA59014.1 CAC20706.1 NP_035504.1 | Q64468 Q64687 Q8BL76 Q8BWI0 Q8K1C1 Q9EPK3 | |
| α-2,8-sialyltransferase (ST8Sia VI) | St8sia6 | Mus musculus | n.d. | AB059554 AK085105 NM_145838 | BAC01265.1 BAC39367.1 NP_666837.1 | Q8BI43 Q8K4T1 | |
| α-2,8-sialyltransferase ST8Sia II | St8sia2 | Mus musculus | 2.4.99.- | X83562 X99646 X99647 X99648 X99649 X99650 X99651 NM_009181 | CAA58548.1 CAA67965.1 CAA67965.1 CAA67965.1 CAA67965.1 CAA67965.1 CAA67965.1 NP_033207.1 | O35696 | |
| α-2,8-sialyltransferase ST8Sia IV | St8sia4 | Mus musculus | 2.4.99.8 | BC060112 AK003690 AK041723 AJ223956 X88000 Y09484 NM_009183 | AAH60112.1 BAB22941.1 BAC31044.1 CAA11685.1 CAA59992.1 CAA70692.1 NP_033209.1 | Q64692 Q8BY79 | |
| α-2,8-sialyltransferase ST8Sia V | St8sia5 | Mus musculus | 2.4.99.- | BC034855 AK078670 X98014 X98014 X98014 NM_013666 NM_153124 NM_177416 | AAH34855.1 BAC37354.1 CAA66642.1 CAA66643.1 CAA66644.1 NP_038694.1 NP_694764.1 NP_803135.1 | P70128 P70127 P70128 Q8BJW8 Q8JZQ3 | |
| α-2,8-sialyltransferase ST8Sia III | St8sia3 | Mus musculus | 2.4.99.- | BC075645 AK015874 X80502 NM_009182 | AAH75645.1 BAB30012.1 CAA56665.1 NP_033208.1 | Q64689 Q9CUJ6 | |
| GD1 synthase (ST6GalNAc V) | St6galnac5 | Mus musculus | n.d. | BC055737 AB030836 AB028840 AK034387 AK038434 AK042683 NM_012028 | AAH55737.1 BAA85747.1 BAA89292.1 BAC28693.1 BAC29997.1 BAC31331.1 NP_036158.2 | Q8CAM7 Q8CBX1 Q8QYJ1 Q9R0K8 | |
| GM3 synthase (α-2,3-sialyltransferase) ST3Gal V | St3gal5 | Mus musculus | 2.4.99.9 | AF119416 - AB018048 AB013302 AK013961 Y15003 NM_011375 | AAF66147.1 AAP85083.1 BAA33491.1 BAA78487.1 BAB29071.1 CAA75235.1 NP_035505.1 | O88829 Q9CZ65 Q9QWF9 | |
| N-acetylgalactosaminide α-2,6-sialyltransferase (ST6GalNAc VI) | St6galnac6 | Mus musculus | 2.4.99.- | BC035885 AB035174 AB035123 AK030648 | AAH35985.1 BAA87838.1 BAA95940.1 BAC27064.1 | Q8CDC3 Q8JZW3 Q9JM95 Q9R0G9 | |

FIG. 9H

| Protein | Organism | EC# | GenBank / GenPept | SwissProt | PDB / 3D |
|---|---|---|---|---|---|
| | | | NM_016973 | NP_058669.1 | |
| M138L | Myxoma virus | n.d. | U46578 AF170726 NC_001132 | AAD30069.1 AAE61323.1 AAE61328.1 AAF15026.1 NP_051852.1 | |
| α-2,3-sialyltransferase (St3Gal-I) | Oncorhynchus mykiss | n.d. | AJ585760 | CAE51384.1 | |
| α-2,6-sialyltransferase (Siat1) | Oncorhynchus mykiss | n.d. | AJ626849 | CAF05848.1 | |
| α-2,8-polysialyltransferase IV (ST8Sia IV) | Oncorhynchus mykiss | n.d. | AB094402 | BAC77411.1 | Q7T2X5 |
| GalNAc α-2,6-sialyltransferase (RtST6GalNAc) | Oncorhynchus mykiss | n.d. | AB097043 | BAC77520.1 | Q7T2X4 |
| α-2,3-sialyltransferase ST3Gal IV | Oryctolagus cuniculus | 2.4.99.- | AF121987 | AAF28871.1 | Q9N257 |
| OJ1217_F02.7 | Oryza sativa (japonica cultivar-group) | n.d. | AP004064 | BAD07616.1 | |
| OSJNBa0043L24.2 or OSJNBb0082J11.9 | Oryza sativa (japonica cultivar-group) | n.d. | AL731628 AL662933 | CAD41185.1 CAE04714.1 | |
| P0683D2.18 or P0489B03.1 | Oryza sativa (japonica cultivar-group) | n.d. | AP003269 AP003794 | BAB63715.1 BAB90552.1 | |
| α-2,6-sialyltransferase ST6GalNAc V (Siat7E) (fragment) | Oryzias latipes | n.d. | AJ646878 | CAG26705.1 | |
| α-2,3-sialyltransferase ST3Gal I (Siat4) | Pan troglodytes | n.d. | AJ744803 | CAG32839.1 | |
| α-2,3-sialyltransferase ST3Gal II (Siat5) | Pan troglodytes | n.d. | AJ744804 | CAG32840.1 | |
| α-2,3-sialyltransferase ST3Gal III (Siat6) | Pan troglodytes | n.d. | AJ626819 | CAF25177.1 | |
| α-2,3-sialyltransferase ST3Gal IV (Siat4c) | Pan troglodytes | n.d. | AJ626824 | CAF25182.1 | |
| α-2,3-sialyltransferase ST3Gal VI (Siat10) | Pan troglodytes | n.d. | AJ744808 | CAG32844.1 | |
| α-2,6-sialyltransferase (Siat7A) | Pan troglodytes | n.d. | AJ748740 | CAG38615.1 | |
| α-2,6-sialyltransferase (Siat7B) | Pan troglodytes | n.d. | AJ748741 | CAG38616.1 | |
| α-2,6-sialyltransferase ST6GalNAc III (Siat7C) | Pan troglodytes | n.d. | AJ634454 | CAG25676.1 | |
| α-2,6-sialyltransferase ST6GalNAc IV (Siat7D) (fragment) | Pan troglodytes | n.d. | AJ646870 | CAG26699.1 | |
| α-2,6-sialyltransferase ST6GalNAc V (Siat7E) | Pan troglodytes | n.d. | AJ646875 | CAG26704.1 | |
| α-2,6-sialyltransferase ST6GalNAc VI (Siat7F) (fragment) | Pan troglodytes | n.d. | AJ646882 | CAG26711.1 | |
| α-2,8-sialyltransferase 8A (Siat8A) | Pan troglodytes | 2.4.99.8 | AJ697858 | CAG26896.1 | |
| α-2,8-sialyltransferase 8B (Siat8B) | Pan troglodytes | n.d. | AJ697859 | CAG26897.1 | |
| α-2,8-sialyltransferase 8C (Siat8C) | Pan troglodytes | n.d. | AJ697860 | CAG26898.1 | |
| α-2,8-sialyltransferase 8D (Siat8D) | Pan troglodytes | n.d. | AJ697861 | CAG26899.1 | |
| α-2,8-sialyltransferase | Pan troglodytes | n.d. | AJ697862 | CAG26900.1 | |

FIG. 9I

| Protein | Organism | EC# | GenBank / GenPept | SwissProt | PDB / 3D |
|---|---|---|---|---|---|
| 8E (Siat8E) | | | | | |
| α-2,8-sialyltransferase 8F (Siat8F) | Pan troglodytes | n.d. | AJ697863 CAG26981.1 | | |
| β-galactosamide α-2,6-sialyltransferase I (ST6Gal I; Siat1) | Pan troglodytes | 2.4.99.1 | AJ627824 CAF29492.1 | | |
| β-galactosamide α-2,6-sialyltransferase II (ST6Gal II) | Pan troglodytes | n.d. | AJ627825 CAF29493.1 | | |
| GM3 synthase ST3Gal V (Siat9) | Pan troglodytes | n.d. | AJ744807 CAG32843.1 | | |
| S138L | Rabbit fibroma virus Kasza | n.d. | NC_001266 NP_052025 | | |
| α-2,3-sialyltransferase ST3Gal III | Rattus norvegicus | 2.4.99.6 | M97754 AAA42146.1 NM_031697 NP_113885.1 | Q02734 | |
| α-3,3-sialyltransferase ST3Gal IV (Siat4c) | Rattus norvegicus | n.d. | AJ626825 CAF25183.1 | | |
| α-3,3-sialyltransferase ST3Gal VI | Rattus norvegicus | n.d. | AJ626743 CAF25053.1 | | |
| α-2,6-sialyltransferase ST3Gal II | Rattus norvegicus | 2.4.99.- | X76988 CAA54293.1 NM_031695 NP_113883.1 | Q11205 | |
| α-2,6-sialyltransferase ST6Gal I | Rattus norvegicus | 2.4.99.1 | M18769 AAA41196.1 M83143 AAB07233.1 | P13721 | |
| α-2,6-sialyltransferase ST6GalNAc I (Siat7A) | Rattus norvegicus | n.d. | AJ634458 CAG25684.1 | | |
| α-2,6-sialyltransferase ST6GalNAc II (Siat7B) | Rattus norvegicus | n.d. | AJ634457 CAG25679.1 | | |
| α-2,6-sialyltransferase ST6GalNAc III | Rattus norvegicus | 2.4.99.- | L29554 AAC43086.1 BC072501 AAH72501.1 NM_019123 NP_061996.1 | Q64686 | |
| α-2,6-sialyltransferase ST6GalNAc IV (Siat7D) (fragment) | Rattus norvegicus | n.d. | AJ646871 CAG26700.1 | | |
| α-3,6-sialyltransferase ST6GalNAc V (Siat7E) | Rattus norvegicus | n.d. | AJ646872 CAG26701.1 | | |
| α-3,6-sialyltransferase ST6GalNAc VI (Siat7F) (fragment) | Rattus norvegicus | n.d. | AJ646881 CAG26718.1 | | |
| α-2,8-sialyltransferase (GD3 synthase) ST8Sia I | Rattus norvegicus | 2.4.99.- | U53883 AAC27541.1 D45255 BAA08213.1 | P70554 P97713 | |
| α-2,8-sialyltransferase (SIAT8E) | Rattus norvegicus | n.d. | AJ699422 CAG27884.1 | | |
| α-2,8-sialyltransferase (SIAT8F) | Rattus norvegicus | n.d. | AJ699423 CAG27885.1 | | |
| α-2,8-sialyltransferase ST8Sia II | Rattus norvegicus | 2.4.99.- | L13445 AAA42147.1 NM_057156 NP_476497.1 | Q07977 Q64688 | |
| α-2,8-sialyltransferase ST8Sia III | Rattus norvegicus | 2.4.99.- | U55938 AAB50061.1 NM_013029 NP_037161.1 | P97877 | |
| α-2,8-sialyltransferase ST8Sia IV | Rattus norvegicus | 2.4.99.- | U90215 AAB49963.1 | O08563 | |
| β-galactosamide α-2,8-sialyltransferase II (ST8Gal II) | Rattus norvegicus | n.d. | AJ627826 CAF29494.1 | | |
| GM3 synthase ST3Gal V | Rattus norvegicus | n.d. | AB018049 BAA33493.1 NM_031337 NP_112627.1 | O88338 | |

FIG. 9J

| Protein | Organism | EC# | GenBank / GenPept | SwissProt | PDB / 3D |
|---|---|---|---|---|---|
| sialyltransferase ST3Gal-I (Siat4A) | Rattus norvegicus | n.d. | AJ748849 | CAG44449.1 | |
| α-2,3-sialyltransferase (St3Gal-II) | Silurana tropicalis | n.d. | AJ585763 | CAE51387.1 | |
| α-2,6-sialyltransferase (Siat7b) | Silurana tropicalis | n.d. | AJ620859 | CAF05849.1 | |
| α-2,6-sialyltransferase (St6galnac) | Strongylocentrotus purpuratus | n.d. | AJ889425 | CAG27887.1 | |
| α-2,3-sialyltransferase (ST3GAL-III) | Sus scrofa | n.d. | AJ585765 | CAE51389.1 | |
| α-2,3-sialyltransferase (ST3GAL-IV) | Sus scrofa | n.d. | AJ584874 | CAE48299.1 | |
| α-2,3-sialyltransferase ST3Gal I | Sus scrofa | 2.4.99.4 | M97753 | AAA31125.1 | Q02745 |
| α-2,6-sialyltransferase (fragment) ST6Gal I | Sus scrofa | 2.4.99.1 | AF136748 | AAD33859.1 | Q9XSG8 |
| N-galactosamide α-2,6-sialyltransferase (ST6GalNAc-V) | Sus scrofa | n.d. | AJ620948 | CAF06585.2 | |
| sialyltransferase (fragment) ST6Gal I | sus scrofa | n.d. | AF041831 | AAC15633.1 | O62717 |
| ST6GALNAC-V | Sus scrofa | n.d. | AJ620948 | CAF06585.1 | |
| α-2,3-sialyltransferase (Siat5-r) | Takifugu rubripes | n.d. | AJ744805 | CAG32841.1 | |
| α-2,3-sialyltransferase ST3Gal I (Siat4) | Takifugu rubripes | n.d. | AJ626816 | CAF25174.1 | |
| α-2,3-sialyltransferase ST3Gal II (Siat5) (fragment) | Takifugu rubripes | n.d. | AJ626817 | CAF25175.1 | |
| α-2,3-sialyltransferase ST3Gal III (Siat6) | Takifugu rubripes | n.d. | AJ626818 | CAF25176.1 | |
| α-2,6-sialyltransferase ST6Gal I (Siat1) | Takifugu rubripes | n.d. | AJ744800 | CAG32836.1 | |
| α-2,6-sialyltransferase ST6GalNAc II (Siat7B) | Takifugu rubripes | n.d. | AJ634460 | CAG25681.1 | |
| α-2,6-sialyltransferase ST6GalNAc II B (Siat7B-related) | Takifugu rubripes | n.d. | AJ634461 | CAG25682.1 | |
| α-2,6-sialyltransferase ST6GalNAc III (Siat7C) (fragment) | Takifugu rubripes | n.d. | AJ634458 | CAG25678.1 | |
| α-2,6-sialyltransferase ST6GalNAc IV (siat7D) (fragment) | Takifugu rubripes | 2.4.99.3 | Y17466 AJ646869 | CAB44338.1 CAG26698.1 | Q9W8U8 |
| α-2,6-sialyltransferase ST6GalNAc V (Siat7E) (fragment) | Takifugu rubripes | n.d. | AJ646873 | CAG26702.1 | |
| α-2,6-sialyltransferase ST6GalNAc VI (Siat7F) (fragment) | Takifugu rubripes | n.d. | AJ646880 | CAG26709.1 | |
| α-2,8-sialyltransferase ST8Sia I (Siat 8A) (fragment) | Takifugu rubripes | n.d. | AJ715534 | CAG29373.1 | |
| α-2,8-sialyltransferase ST8Sia II (Siat 8B) (fragment) | Takifugu rubripes | n.d. | AJ715538 | CAG29377.1 | |
| α-2,8-sialyltransferase ST8Sia III (Siat 8C) (fragment) | Takifugu rubripes | n.d. | AJ715541 | CAG29380.1 | |
| α-2,8-sialyltransferase ST8Sia IIIr (Siat 8Cr) | Takifugu rubripes | n.d. | AJ715542 | CAG29381.1 | |
| α-2,8-sialyltransferase ST8Sia V (Siat 8E) | Takifugu rubripes | n.d. | AJ715547 | CAG29386.1 | |

FIG. 9K

| Protein | Organism | EC# | GenBank / GenPept | | SwissProt | PDB / 3D |
|---|---|---|---|---|---|---|
| (fragment) | | | | | | |
| α-2,8-sialyltransferase ST8Sia VI (Siat 8F) (fragment) | Takifugu rubripes | n.d. | AJ715549 | CAG29388.1 | | |
| α-2,8-sialyltransferase ST8Sia VIr (Siat 8Fr) | Takifugu rubripes | n.d. | AJ715550 | CAG29389.1 | | |
| α-2,3-sialyltransferase (Siat5-r) | Tetraodon nigroviridis | n.d. | AJ744806 | CAG32842.1 | | |
| α-2,3-sialyltransferase ST3Gal I (Siat4) | Tetraodon nigroviridis | n.d. | AJ744802 | CAG32838.1 | | |
| α-2,3-sialyltransferase ST3Gal III (Siat6) | Tetraodon nigroviridis | n.d. | AJ628822 | CAF25180.1 | | |
| α-2,6-sialyltransferase ST6GalNAc II (Siat7B) | Tetraodon nigroviridis | n.d. | AJ634462 | CAG25683.1 | | |
| α-2,6-sialyltransferase ST6GalNAc V (Siat7E) (fragment) | Tetraodon nigroviridis | n.d. | AJ645879 | CAG26708.1 | | |
| α-2,8-sialyltransferase ST8Sia I (Siat 8A) (fragment) | Tetraodon nigroviridis | n.d. | AJ715536 | CAG29375.1 | | |
| α-2,8-sialyltransferase ST8Sia II (Siat 8B) (fragment) | Tetraodon nigroviridis | n.d. | AJ715537 | CAG29376.1 | | |
| α-2,8-sialyltransferase ST8Sia III (Siat 8C) (fragment) | Tetraodon nigroviridis | n.d. | AJ715539 | CAG29378.1 | | |
| α-2,8-sialyltransferase ST8Sia IIIr (Siat 8Cr) (fragment) | Tetraodon nigroviridis | n.d. | AJ715540 | CAG29379.1 | | |
| α-2,8-sialyltransferase ST8Sia V (Siat 8E) (fragment) | Tetraodon nigroviridis | n.d. | AJ715548 | CAG29387.1 | | |
| α-2,3-sialyltransferase (St3Gal-II) | Xenopus laevis | n.d. | AJ585762 | CAE51386.1 | | |
| α-2,3-sialyltransferase (St3Gal-VI) | Xenopus laevis | n.d. | AJ585763 | CAE51398.1 | | |
| α-2,3-sialyltransferase St3Gal-III (Siat6) | Xenopus laevis | n.d. | AJ585764 AJ628823 | CAE51388.1 CAF25181.1 | | |
| α-2,8-polysialyltransferase | Xenopus laevis | 2.4.99.- | AB007468 | BAA32817.1 | O93234 | |
| α-2,8-sialyltransferase ST8Sα-I (Siat8A;GD3 synthase) | Xenopus laevis | n.d. | AY272056 AY272057 AJ704562 | AAQ16162.1 AAQ16163.1 CAG28695.1 | | |
| Unknown (protein for MGC:81265) | Xenopus laevis | n.d. | BC068760 | AAH68760.1 | | |
| α-2,3-sialyltransferase (3Gal-VI) | Xenopus tropicalis | n.d. | AJ628744 | CAF25054.1 | | |
| α-2,3-sialyltransferase (Siat4c) | Xenopus tropicalis | n.d. | AJ622608 | CAF22058.1 | | |
| α-2,6-sialyltransferase ST6GalNAc V (Siat7E) (fragment) | Xenopus tropicalis | n.d. | AJ645876 | CAG26707.1 | | |
| α-2,8-sialyltransferase ST8Sia III (Siat 8C) (fragment) | Xenopus tropicalis | n.d. | AJ715544 | CAG29383.1 | | |
| β-galactosamide α-2,6-sialyltransferase II (ST6Gal II) | Xenopus tropicalis | n.d. | AJ627828 | CAF29496.1 | | |
| sialyltransferase St8Sia I | Xenopus tropicalis | n.d. | AY862775 | AAT67042 | | |
| poly-α-2,8-sialosyl sialyltransferase (NeuS) | Escherichia coli K1 | 2.4.-.- | M76370 X60598 | AAA24213.1 CAA43053.1 | Q57269 | |
| polysialyltransferase | Escherichia coli K92 | 2.4.-.- | M88479 | AAA24215.1 | Q47404 | |

FIG. 9L

| Protein | Organism | EC# | GenBank / GenPept | | SwissProt | PDB / 3D |
|---|---|---|---|---|---|---|
| α-2,8 polysialyltransferase SiaD | Neisseria meningitidis B1940 | 2.4.-.- | M95053 X78068 | AAA20478.1 CAA54985.1 | Q51281 Q51145 | |
| SynE | Neisseria meningitidis FAM18 | n.d. | U75650 | AAB53842.1 | Q06435 | |
| polysialyltransferase (SiaD)(fragment) | Neisseria meningitidis M1019 | n.d. | AY234192 | AAO85290.1 | | |
| SiaD (fragment) | Neisseria meningitidis M209 | n.d. | AY281046 | AAP34769.1 | | |
| SiaD (fragment) | Neisseria meningitidis M3045 | n.d. | AY281044 | AAP34767.1 | | |
| polysialyltransferase (SiaD)(fragment) | Neisseria meningitidis M3315 | n.d. | AY234191 | AAO85289.1 | | |
| SiaD (fragment) | Neisseria meningitidis M3515 | n.d. | AY281047 | AAP34770.1 | | |
| polysialyltransferase (SiaD)(fragment) | Neisseria meningitidis M4211 | n.d. | AY234190 | AAO85288.1 | | |
| SiaD (fragment) | Neisseria meningitidis M4642 | n.d. | AY281048 | AAP34771.1 | | |
| polysialyltransferase (SiaD)(fragment) | Neisseria meningitidis M5177 | n.d. | AY234193 | AAO85291.1 | | |
| SiaD | Neisseria meningitidis M5178 | n.d. | AY281043 | AAP34766.1 | | |
| SiaD (fragment) | Neisseria meningitidis M980 | n.d. | AY281045 | AAP34768.1 | | |
| NMB0067 | Neisseria meningitidis MC58 | n.d. | NC_003112 | NP_273131 | | |
| Lst | Aeromonas punctata Sch3 | n.d. | AF126258 | AAS66624.1 | | |
| ORF2 | Haemophilus influenzae A2 | n.d. | M94855 | AAA24973.1 | | |
| HI1699 | Haemophilus influenzae Rd | n.d. | U32842 NC_000907 | AAC23345.1 NP_439641.1 | Q48211 | |
| α-2,3-sialyltransferase | Neisseria gonorrhoeae F62 | 2.4.99.4 | U60664 | AAC44539.1 AAE87205.1 | P72074 | |
| α-2,3-sialyltransferase | Neisseria meningitidis 126E, NRCC 4010 | 2.4.99.4 | U60662 | AAC44544.2 | | |
| α-2,3-sialyltransferase | Neisseria meningitidis 406Y, NRCC 4030 | 2.4.99.4 | U60661 | AAC44543.1 | | |
| α-2,3-sialyltransferase (NMB0922) | Neisseria meningitidis MC58 | 2.4.99.4 | U60660 AE002443 NC_003112 | AAC44541.1 AAF41330.1 NP_273962.1 | P72097 | |
| NMA1118 | Neisseria meningitidis Z2491 | n.d. | AL162755 NC_003116 | CAB84380.1 NP_283887.1 | Q9JXN5 | |
| PM0508 | Pasteurella multocida PM70 | n.d. | AE006088 NC_002663 | AAK02592.1 NP_245445.1 | Q9CNC4 | |
| WaaH | Salmonella enterica SARB25 | n.d. | AF519787 | AAM82550.1 | Q8KS93 | |
| WaaH | Salmonella enterica SARB3 | n.d. | AF519788 | AAM82551.1 | Q8KS92 | |
| WaaH | Salmonella enterica SARB39 | n.d. | AF519789 | AAM82552.1 | | |
| WaaH | Salmonella enterica SARB53 | n.d. | AF519790 | AAM82553.1 | | |
| WaaH | Salmonella enterica SARB57 | n.d. | AF519791 | AAM82554.1 | Q8KS91 | |
| WaaH | Salmonella enterica SARB71 | n.d. | AF519793 | AAM82556.1 | Q8KS89 | |
| WaaH | Salmonella enterica | n.d. | AF519792 | AAM82555.1 | Q8KS90 | |

FIG. 9M

| Protein | Organism | EC# | GenBank / GenPept | | SwissProt | PDB / 3D |
|---|---|---|---|---|---|---|
| | SARB8 | | | | | |
| WaaH | Salmonella enterica SARC10/ | n.d. | AF519778 | AAM88840.1 | Q8KS99 | |
| WaaH (fragment) | Salmonella enterica SARC12 | n.d. | AF519781 | AAM88842.1 | | |
| WaaH (fragment) | Salmonella enterica SARC13/ | n.d. | AF519782 | AAM88843.1 | Q8KS98 | |
| WaaH (fragment) | Salmonella enterica SARC14/ | n.d. | AF519783 | AAM88844.1 | Q8KS97 | |
| WaaH | Salmonella enterica SARC15// | n.d. | AF519784 | AAM88845.1 | Q8KS96 | |
| WaaH | Salmonella enterica SARC16// | n.d. | AF519785 | AAM88846.1 | Q8KS95 | |
| WaaH (fragment) | Salmonella enterica SARC3/ | n.d. | AF519772 | AAM88834.1 | Q8KSA4 | |
| WaaH (fragment) | Salmonella enterica SARC4/ | n.d. | AF519773 | AAM88835.1 | Q8KSA3 | |
| WaaH | Salmonella enterica SARC5//a | n.d. | AF519774 | AAM88836.1 | | |
| WaaH | Salmonella enterica SARC6//a | n.d. | AF519775 | AAM88837.1 | Q8KSA2 | |
| WaaH | Salmonella enterica SARC8 | n.d. | AF519777 | AAM88838.1 | Q8KSA1 | |
| WaaH | Salmonella enterica SARC9V | n.d. | AF519778 | AAM88839.1 | Q8KSA0 | |
| UDP-glucose : α-1,2-glucosyltransferase (WaaH) | Salmonella enterica subsp. arizonae SARC 5 | 2.4.1.- | AF511116 | AAM48166.1 | | |
| bifunctional α-2,3-/-2,8-sialyltransferase (Cst-II) | Campylobacter jejuni ATCC 43449 | n.d. | AF401529 | AAL06084.1 | Q93C25 | |
| Cst | Campylobacter jejuni 81-176 | n.d. | AF305571 | AAL89368.1 | | |
| α-2,3-sialyltransferase (Cst-II) | Campylobacter jejuni ATCC 43429 | 2.4.99.- | AY044156 | AAK73183.1 | | |
| α-2,3-sialyltransferase (Cst-II) | Campylobacter jejuni ATCC 43430 | 2.4.99.- | AF400047 | AAK85419.1 | | |
| α-2,3-sialyltransferase (Cst-II) | Campylobacter jejuni ATCC 43432 | 2.4.99.- | AF215659 | AAG43979.1 | Q9F0M9 | |
| α-2,3/8-sialyltransferase (CstII) | Campylobacter jejuni ATCC 43438 | n.d. | AF400048 | AAK91725.1 | Q93MQ0 | |
| α-2,3-sialyltransferase cst-II | Campylobacter jejuni ATCC 43446 | 2.4.99.- | AF167344 | AAF34137.1 | | |
| α-2,3-sialyltransferase (Cst-II) | Campylobacter jejuni ATCC 43456 | 2.4.99.- | AF401528 | AAL85998.1 | Q93D05 | |
| α-2,3-/α-2,8-sialyltransferase (CstII) | Campylobacter jejuni ATCC 43460 | 2.4.99.- | AY044866 | AAK96001.1 | Q93BX6 | |
| α-2,3/8-sialyltransferase (Cst-II) | Campylobacter jejuni ATCC 700297 | n.d. | AF216647 | AAL36462.1 | | |
| ORF | Campylobacter jejuni GB11 | n.d. | AY422197 | AAR82875.1 | | |
| α-2,3-sialyltransferase cstII | Campylobacter jejuni MSC57362 | 2.4.99.- | AF195055 | AAG29922.1 | | |
| α-2,3-sialyltransferase cstII Cj1140 | Campylobacter jejuni NCTC 11168 | 2.4.99.- | AL139077 NC_002163 | CAB73395.1 NP_282288.1 | Q9PNF4 | |
| α-2,3-/α-2,8-sialyltransferase II (cstII) | Campylobacter jejuni O:10 | n.d. | - AX934427 | AAC96569.1 CAF04167.1 | | |
| α-2,3-/α-2,8-sialyltransferase II (CstII) | Campylobacter jejuni O:19 | n.d. | AX934431 | CAF04169.1 | | |
| α-2,3-/α-2,8-sialyltransferase II (CstII) | Campylobacter jejuni O:36 | n.d. | AX934436 | CAF04171.1 | | |
| α-2,3-/α-2,8- | Campylobacter | n.d. | AX934434 | CAF04170.1 | | |

FIG. 9N

| Protein | Organism | EC# | GenBank / GenPept | | SwissProt | PDB / 3D |
|---|---|---|---|---|---|---|
| sialyltransferase II (CstII) | jejuni O:4 | | | | | |
| α-2,3/α-2,8-sialyltransferase II (CstII) | Campylobacter jejuni O:41 | n.d. | -<br>-<br>AX934439 | AAO96670.1<br>AAT17967.1<br>CAF04168.1 | | |
| α-2,3-sialyltransferase cst-I | Campylobacter jejuni OH4384 | 2.4.99.- | AF130485<br>- | AAF13495.1<br>AAS36261.1 | Q9RGF1 | |
| bifunctional α-2,3/-2,8-sialyltransferase (Cst-II) | Campylobacter jejuni OH4384 | 2.4.99.- | AF130984<br>AX934435 | AAF31771.1<br>CAF04166.1 | 1RO7<br>1RO8 | C<br>A |
| HI0352 (fragment) | Haemophilus influenzae Rd | n.d. | U32720<br>X57315<br>NC_000907 | AAC22013.1<br>CAA40567.1<br>NP_438516.1 | P24324 | |
| PM1174 | Pasteurella multocida PM70 | n.d. | AE006157<br>NC_003863 | AAK03258.1<br>NP_246111.1 | Q9CLP3 | |
| Sequence 10 from patent US 6503744 | Unknown | n.d. | - | AAO96672.1 | | |
| Sequence 10 from patent US 6699705 | Unknown | n.d. | - | AAT17969.1 | | |
| Sequence 12 from patent US 6699705 | Unknown | n.d. | - | AAT17970.1 | | |
| Sequence 2 from patent US 6709834 | Unknown | n.d. | - | AAT23232.1 | | |
| Sequence 3 from patent US 6503744 | Unknown | n.d. | - | AAO96668.1 | | |
| Sequence 3 from patent US 6699705 | Unknown | n.d. | - | AAT17965.1 | | |
| Sequence 34 from patent US 6503744 | Unknown | n.d. | - | AAO96684.1 | | |
| Sequence 35 from patent US 6503744 (fragment) | Unknown | n.d. | - | AAO96685.1<br>AAS36262.1 | | |
| Sequence 48 from patent US 6699705 | Unknown | n.d. | - | AAT17988.1 | | |
| Sequence 5 from patent US 6699705 | Unknown | n.d. | - | AAT17966.1 | | |
| Sequence 9 from patent US 6503744 | Unknown | n.d. | - | AAO96671.1 | | |

SEQUENCE LISTING

<160> NUMBER OF SEQ ID NOS: 1

<210> SEQ ID NO 1
<211> LENGTH: 415
<212> TYPE: PRT
<213> ORGANISM: Homo sapiens

<400> SEQUENCE: 1

```
Tyr Asn Ser Gly Lys Leu Glu Glu Phe Val Gln Gly Asn Leu Glu Arg
1               5                   10                  15
Glu Cys Met Glu Glu Lys Cys Ser Phe Glu Glu Ala Arg Glu Val Phe
            20                  25                  30
Glu Asn Thr Glu Arg Thr Thr Glu Phe Trp Lys Gln Tyr Val Asp Gly
                35                  40                  45
Asp Gln Cys Glu Ser Asn Pro Cys Leu Asn Gly Gly Ser Cys Lys Asp
        50                  55                  60
Asp Ile Asn Ser Tyr Glu Cys Trp Cys Pro Phe Gly Phe Glu Gly Lys
65                  70                  75                  80
Asn Cys Glu Leu Asp Val Thr Cys Asn Ile Lys Asn Gly Arg Cys Glu
                85                  90                  95
Gln Phe Cys Lys Asn Ser Ala Asp Asn Lys Val Val Cys Ser Cys Thr
            100                 105                 110
Glu Gly Tyr Arg Leu Ala Glu Asn Gln Lys Ser Cys Glu Pro Ala Val
                115                 120                 125
Pro Phe Pro Cys Gly Arg Val Ser Val Ser Gln Thr Ser Lys Leu Thr
        130                 135                 140
Arg Ala Glu Ala Val Phe Pro Asp Val Asp Tyr Val Asn Ser Thr Glu
145                 150                 155                 160
Ala Glu Thr Ile Leu Asp Asn Ile Thr Gln Ser Thr Gln Ser Phe Asn
                165                 170                 175
Asp Phe Thr Arg Val Val Gly Gly Glu Asp Ala Lys Pro Gly Gln Phe
            180                 185                 190
Pro Trp Gln Val Val Leu Asn Gly Lys Val Asp Ala Phe Cys Gly Gly
        195                 200                 205
Ser Ile Val Asn Glu Lys Trp Ile Val Thr Ala Ala His Cys Val Glu
210                 215                 220
Thr Gly Val Lys Ile Thr Val Val Ala Gly Glu His Asn Ile Glu Glu
225                 230                 235                 240
Thr Glu His Thr Glu Gln Lys Arg Asn Val Ile Arg Ile Ile Pro His
                245                 250                 255
His Asn Tyr Asn Ala Ala Ile Asn Lys Tyr Asn His Asp Ile Ala Leu
            260                 265                 270
Leu Glu Leu Asp Glu Pro Leu Val Leu Asn Ser Tyr Val Thr Pro Ile
        275                 280                 285
Cys Ile Ala Asp Lys Glu Tyr Thr Asn Ile Phe Leu Lys Phe Gly Ser
290                 295                 300
Gly Tyr Val Ser Gly Trp Gly Arg Val Phe His Lys Gly Arg Ser Ala
305                 310                 315                 320
Leu Val Leu Gln Tyr Leu Arg Val Pro Leu Val Asp Arg Ala Thr Cys
                325                 330                 335
Leu Arg Ser Thr Lys Phe Thr Ile Tyr Asn Asn Met Phe Cys Ala Gly
            340                 345                 350
Phe His Glu Gly Gly Arg Asp Ser Cys Gln Gly Asp Ser Gly Gly Pro
        355                 360                 365
His Val Thr Glu Val Glu Gly Thr Ser Phe Leu Thr Gly Ile Ile Ser
        370                 375                 380
Trp Gly Glu Glu Cys Ala Met Lys Gly Lys Tyr Gly Ile Tyr Thr Lys
385                 390                 395                 400
Val Ser Arg Tyr Val Asn Trp Ile Lys Glu Lys Thr Lys Leu Thr
                405                 410                 415
```

GLYCOPEGYLATED FACTOR IX

CROSS-REFERENCES TO RELATED APPLICATIONS

The present application is a continuation of U.S. patent application Ser. No. 13/897,529, filed on May 20, 2013, which is a continuation of U.S. patent application Ser. No. 13/837,850, filed on Mar. 15, 2013, which is a continuation-in-part of U.S. patent application Ser. No. 11/915,239, filed on Nov. 21, 2007, which is a U.S. national phase patent application of PCT Patent Application No. PCT/US2006/020230, filed Mar. 25, 2006, which claims priority under 35 U.S.C. §119(e) to U.S. Provisional Patent Application No. 60/684,729 filed May 25, 2005, U.S. Provisional Patent Application No. 60/707,994, filed Aug. 12, 2005, and U.S. Provisional Patent Application No. 60/710,535 filed Aug. 23, 2005, each of which are hereby incorporated by reference in their entirety for all purposes. U.S. patent application Ser. No. 13/837,850, filed on Mar. 15, 2013 is also a continuation-in-part of U.S. patent application Ser. No. 11/867,553, filed on Oct. 4, 2007, which claims priority under 35 U.S.C. §119(e) to U.S. Provisional Patent Application 60/828,208, filed Oct. 4, 2006, each of which are hereby incorporated by reference in their entirety for all purposes. U.S. patent application Ser. No. 13/837,850, filed on Mar. 15, 2013 is also a continuation-in-part of U.S. patent application Ser. No. 13/246,512, filed on Sep. 27, 2011, which is a continuation of U.S. patent application Ser. No. 12/496,595, filed on Jul. 1, 2009, issued as U.S. Pat. No. 8,063,015, which is a continuation of U.S. patent application Ser. No. 10/552,896, filed Oct. 11, 2005, now abandoned, which is the U.S. national phase of PCT Patent Application No. PCT/US2004/011494 filed Apr. 9, 2004, which application claims priority under 35 U.S.C. §120 to U.S. patent application Ser. No. 10/411,012, filed Apr. 9, 2003, issued as U.S. Pat. No. 7,265,084, U.S. patent application Ser. No. 10/411,026, filed Apr. 9, 2003, issued as U.S. Pat. No. 7,795,210, U.S. patent application Ser. No. 10/410,962, filed Apr. 9, 2003, issued as U.S. Pat. No. 7,173,003, U.S. patent application Ser. No. 10/411,049, filed Apr. 9, 2003, issued as U.S. Pat. No. 7,297,511, U.S. patent application Ser. No. 10/410,930, filed Apr. 9, 2003, issued as U.S. Pat. No. 7,226,903, U.S. patent application Ser. No. 10/410,897, filed Apr. 9, 2003, issued as U.S. Pat. No. 7,179,617, U.S. patent application Ser. No. 10/410,997, filed Apr. 9, 2003, issued as U.S. Pat. No. 7,157,277, U.S. patent application Ser. No. 10/411,044, filed Apr. 9, 2003, issued as U.S. Pat. No. 8,008,252, U.S. patent application Ser. No. 10/410,980, filed Apr. 9, 2003, issued as U.S. Pat. No. 7,399,613, U.S. patent application Ser. No. 10/410,945, filed Apr. 9, 2003, issued as U.S. Pat. No. 7,214,660, U.S. patent application Ser. No. 10/410,913, filed Apr. 9, 2003, issued as U.S. Pat. No. 7,265,085, U.S. patent application Ser. No. 10/411,037, filed Apr. 9, 2003, issued as U.S. Pat. No. 7,125,843, and U.S. patent application Ser. No. 10/411,043 filed Apr. 9, 2003, issued as U.S. Pat. No. 7,439,043, each of which is hereby incorporated by reference in its entirety for all purposes.

BACKGROUND OF THE INVENTION

Vitamin K-dependent proteins (e.g., Factor IX) contain 9 to 13 gamma-carboxyglutamic acid residues (Gla) in their amino terminal 45 residues. The Gla residues are produced by enzymes in the liver that utilize vitamin K to carboxylate the side chains of glutamic acid residues in protein precursors. Vitamin K-dependent proteins are involved in a number of biological processes, of which the most well described is blood coagulation (reviewed in Nelsestuen, *Vitam. Horm.* 58: 355-389 (2000)). Vitamin K-dependent proteins include protein Z, protein S, prothrombin (Factor II), Factor X, Factor IX, protein C, Factor VII, Gas6, and matrix GLA protein. Factors VII, IX, X and II function in procoagulation processes while protein C, protein S and protein Z serve in anticoagulation roles. Gas6 is a growth arrest hormone encoded by growth arrest-specific gene 6 (gash) and is related to protein S. See, Manfioletti et al. *Mol. Cell. Biol.* 13: 4976-4985 (1993). Matrix GLA protein normally is found in bone and is critical to prevention of calcification of soft tissues in the circulation. Luo et al. *Nature* 386: 78-81 (1997).

The regulation of blood coagulation is a process that presents a number of leading health problems, including both the failure to form blood clots as well as thrombosis, the formation of unwanted blood clots. Agents that prevent unwanted clots are used in many situations and a variety of agents are available. Unfortunately, most current therapies have undesirable side effects. Orally administered anticoagulants such as Warfarin act by inhibiting the action of vitamin K in the liver, thereby preventing complete carboxylation of glutamic acid residues in the vitamin K-dependent proteins, resulting in a lowered concentration of active proteins in the circulatory system and reduced ability to form clots. Warfarin therapy is complicated by the competitive nature of the drug with its target. Fluctuations of dietary vitamin K can result in an over-dose or under-dose of warfarin. Fluctuations in coagulation activity are an undesirable outcome of this therapy.

Injected substances such as heparin, including low molecular weight heparin, also are commonly used anticoagulants. Again, these compounds are subject to overdose and must be carefully monitored.

A newer category of anticoagulants includes active-site modified vitamin K-dependent clotting factors such as factor VIIa and IXa. The active sites are blocked by serine protease inhibitors such as chloromethylketone derivatives of amino acids or short peptides. The active site-modified proteins retain the ability to form complexes with their respective cofactors, but are inactive, thereby producing no enzyme activity and preventing complexing of the cofactor with the respective active enzymes. In short, these proteins appear to offer the benefits of anticoagulation therapy without the adverse side effects of other anticoagulants. Active site modified factor Xa is another possible anticoagulant in this group. Its cofactor protein is factor Va. Active site modified activated protein C (APC) may also form an effective inhibitor of coagulation. See, Sorensen et al. *J. Biol. Chem.* 272: 11863-11868 (1997). Active site modified APC binds to factor Va and prevents factor Xa from binding.

A major inhibition to the use of vitamin K-dependent clotting factors is cost. Biosynthesis of vitamin K-dependent proteins is dependent on an intact glutamic acid carboxylation system, which is present in a small number of animal cell types. Overproduction of these proteins is limited by this enzyme system. Furthermore, the effective dose of these proteins is high. A common dosage is 1000 μg of peptide/kg body weight. See, Harker et al. 1997, supra.

Another phenomena that hampers the use of therapeutic peptides is the well known aspect of protein glycosylation is the relatively short in vivo half life exhibited by these peptides. Overall, the problem of short in vivo half life means that therapeutic glycopeptides must be administered frequently in high dosages, which ultimately translate to higher health care costs than might be necessary if a more efficient method for making longer lasting, more effective glycoprotein therapeutics was available.

Factor VIIa, for example, illustrates this problem. Factor VII and VIIa have circulation half-times of about 2-4 hours in the human. That is, within 2-4 hours, the concentration of the peptide in the serum is reduced by half. When Factor VIIa is used as a procoagulant to treat certain forms of hemophilia, the standard protocol is to inject VIIa every two hours and at high dosages (45 to 90 µg/kg body weight). See, Hedner et al., Transfus. Med. Rev. 7: 78-83 (1993)). Thus, use of these proteins as procoagulants or anticoagulants (in the case of factor VIIa) requires that the proteins be administered at frequent intervals and at high dosages.

One solution to the problem of providing cost effective glycopeptide therapeutics has been to provide peptides with longer in vivo half lives. For example, glycopeptide therapeutics with improved pharmacokinetic properties have been produced by attaching synthetic polymers to the peptide backbone. An exemplary polymer that has been conjugated to peptides is poly(ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

The principal mode of attachment of PEG, and its derivatives, to peptides is a non-specific bonding through a peptide amino acid residue (see e.g., U.S. Pat. No. 4,088,538 U.S. Pat. No. 4,496,689, U.S. Pat. No. 4,414,147, U.S. Pat. No. 4,055,635, and PCT WO 87/00056). Another mode of attaching PEG to peptides is through the non-specific oxidation of glycosyl residues on a glycopeptide (see e.g., WO 94/05332).

In these non-specific methods, poly(ethyleneglycol) is added in a random, non-specific manner to reactive residues on a peptide backbone. Of course, random addition of PEG molecules has its drawbacks, including a lack of homogeneity of the final product, and the possibility for reduction in the biological or enzymatic activity of the peptide. Therefore, for the production of therapeutic peptides, a derivitization strategy that results in the formation of a specifically labeled, readily characterizable, essentially homogeneous product is superior. Such methods have been developed.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes for use in the synthesis of labeled peptides are glycosyltransferases (e.g., sialyltransferases, oligosaccharyltransferases, N-acetylglucosaminyltransferases), and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic synthetic elements are also known (see e.g., Yamamoto et al. Carbohydr. Res. 305: 415-422 (1998) and U.S. Patent Application Publication 20040137557 which is incorporated herein by reference).

Factor IX is an extremely valuable therapeutic peptide. Although commercially available forms of Factor IX are in use today, these peptides can be improved by modifications that enhance the pharmacokinetics of the resulting isolated glycoprotein product. Thus, there remains a need in the art for longer lasting Factor IX peptides with improved effectiveness and better pharmacokinetics. Furthermore, to be effective for the largest number of individuals, it must be possible to produce, on an industrial scale, a Factor IX peptide with improved therapeutic pharmacokinetics that has a predictable, essentially homogeneous, structure which can be readily reproduced over, and over again.

Fortunately, Factor IX peptides with improved pharmacokinetics and methods for making them are described herein. In addition to Factor IX peptides with improved pharmacokinetics, the invention also provides industrially practical and cost effective methods for the production of these Factor IX peptides. The Factor IX peptides of the invention comprise modifying groups such as PEG moieties, therapeutic moieties, biomolecules and the like. The present invention therefore fulfills the need for Factor IX peptides with improved therapeutic effectiveness and improved pharmacokinetics for the treatment of conditions and diseases wherein Factor IX provides effective therapy.

SUMMARY OF THE INVENTION

The present invention relates to the controlled modification of Factor IX with one or more modifying group, e.g., water-soluble polymer, water-insoluble polymer, targeting moiety, etc., provides FIX polymers having heretofore unavailable properties.

In an illustrative aspect, the Factor IX peptide is modified with a water-soluble polymer moiety, e.g., a poly(ethylene glycol) moiety affording a novel Factor IX derivative with pharmacokinetic properties that are surprisingly improved relative to the corresponding native (unconjugated) Factor IX. Moreover, the conjugated Factor IX retains at least the pharmacological activity of the unconjugated peptide.

In a first aspect, the invention provides conjugates between Factor IX and a water-soluble polymer having a $T_{1/2}$ enhanced relative to an identical unconjugated FIX peptide. In a preferred embodiment, these peptides show an enhanced recovery relative to the unconjuted peptide as well.

In an exemplary embodiment, the Factor IX conjugates of the invention are prepared by "glycoconjugation" of the water-soluble polymer to the Factor IX peptide using a sugar donor conjugated to the water-soluble polymer, and an enzyme that is capable of transferring a modified sugar moiety from the donor to a glycosyl or amino acid residue of the peptide. An exemplary strategy for preparation of the Factor IX conjugates of the invention relies on "glycoPEGylation."

"GlycoPEGylated" Factor IX molecules of the invention are produced by the enzyme mediated formation of a conjugate between a glycosylated or non-glycosylated Factor IX peptide and an enzymatically transferable saccharyl moiety that includes a poly(ethylene glycol) moiety within its structure. The PEG moiety is attached to the saccharyl moiety directly (i.e., through a single group formed by the reaction of two reactive groups) or through a linker moiety, e.g., substituted or unsubstituted alkyl, substituted or unsubstituted heteroalkyl, etc.

The polymeric modifying moiety can be attached at any position of a glycosyl moiety of Factor IX. Moreover, the polymeric modifying moiety can be bound to a glycosyl residue at any position in the amino acid sequence of a wild type or mutant Factor IX peptide.

In an exemplary embodiment, the invention provides an Factor IX peptide that is conjugated through a glycosyl linking group to a polymeric modifying moiety. Exemplary Factor IX peptide conjugates include a glycosyl linking group having a formula selected from:

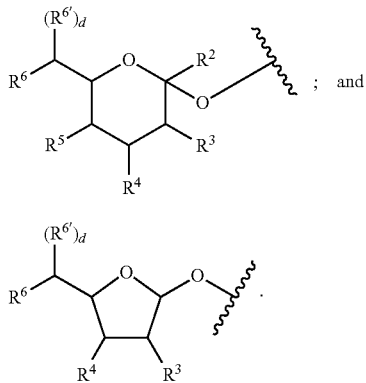

In Formulae I and II, $R^2$ is H, $CH_2OR^7$, $COOR^7$ or $OR^7$, in which $R^7$ represents H, substituted or unsubstituted alkyl or substituted or unsubstituted heteroalkyl. The symbols $R^3$, $R^4$, $R^5$, $R^6$ and $R^{6'}$ independently represent H, substituted or unsubstituted alkyl, $OR^8$, $NHC(O)R^9$. The index d is 0 or 1. $R^8$ and $R^9$ are independently selected from H, substituted or unsubstituted alkyl, substituted or unsubstituted heteroalkyl or sialic acid. At least one of $R^3$, $R^4$, $R^5$, $R^6$ or $R^{6'}$ includes the polymeric modifying moiety e.g., PEG. In an exemplary embodiment, $R^6$ and $R^{6'}$, together with the carbon to which they are attached are components of the side chain of sialic acid. In a further exemplary embodiment, this side chain is functionalized with the polymeric modifying moiety.

In another aspect, the invention provides a method of treating a condition in a subject in need thereof. Exemplary conditions include those characterized by compromised blood clotting in the subject. The method includes the step of administering to the subject an amount of the polymer-modified Factor IX peptide of the invention effective to ameliorate the condition in the subject.

In a further aspect, the invention provides a method of enhancing blood clotting in a mammal. The method includes administering to the mammal an amount of the polymer-modified Factor IX peptide of the invention effective to enhance clotting in the mammal.

The invention also provides a method of treating a condition in a mammalian subject in need of treatment with Factor IX. The method includes the step of administering to the subject an amount of a polymer-modified Factor IX peptide of the invention effective to ameliorate the condition of the subject.

Also provided is a pharmaceutical formulation comprising a polymer-modified Factor IX peptide of the invention and a pharmaceutically acceptable carrier.

Other objects and advantages of the invention will be apparent to those of skill in the art from the detailed description that follows.

DESCRIPTION OF THE DRAWINGS

FIGS. 2A-D are schemes showing an exemplary embodiment of the invention in which a carbohydrate residue on a Factor IX peptide is remodeled and glycopegylated, FIG. 2A shows sialic acid moieties are removed by sialidase and the resulting galactose residues are glycopegylated with the sialic acid derivative of FIG. 5; FIG. 2B shows a mannose residue that is glycopegylated with the sialic acid PEG; FIG. 2C shows a sialic acid moiety of an N-glycan that is glycopegylated with the sialic acid PEG; FIG. 2D shows a sialic acid moiety that is of an O-glycan is glycopegylated with the sialic acid PEG; FIG. 2E is a SDS PAGE gel of Factor IX from FIG. 2(A); FIG. 2F is a SDS PAGE gel of Factor IX from the reaction producing 2(C) and 2(D).

FIG. 4 is a table comparing the activities of the species shown in FIG. 3.

FIG. 5 is the amino acid sequence of Factor IX.

FIGS. 9A-N are tables of sialyltransferases of use to transfer onto an acceptor a modified and/or modified sialic acid moiety, such as those set forth herein.

DETAILED DESCRIPTION OF THE INVENTION AND THE PREFERRED EMBODIMENTS

Abbreviations

Figure 1:
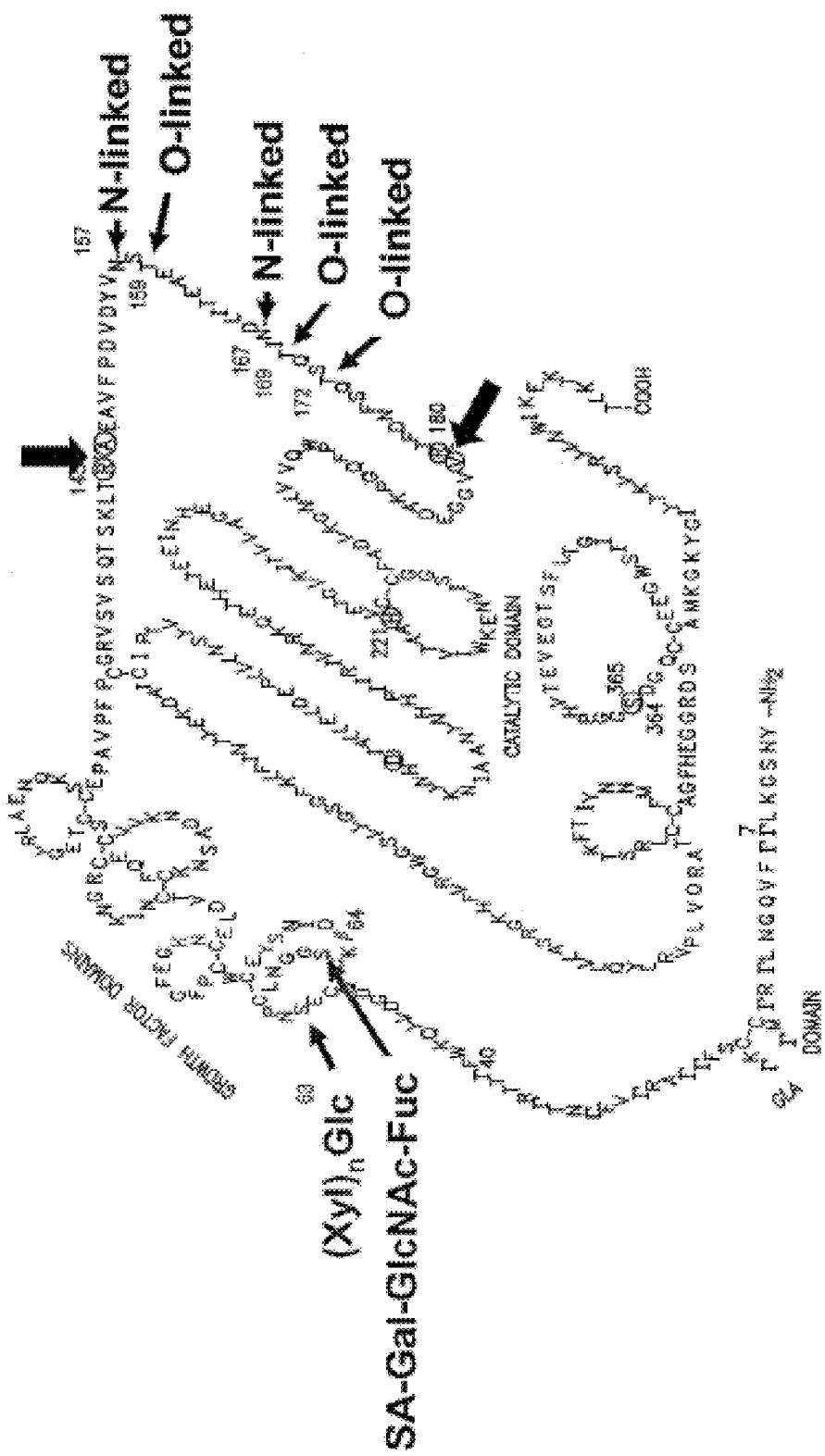
FIG. 1 is the structure of Factor IX, showing the presence and location of potential glycosylation sites at Asn 157, Asn 167; Ser 53, Ser 61, Thr 159, Thr 169, and Thr 172.
Figure 2A:
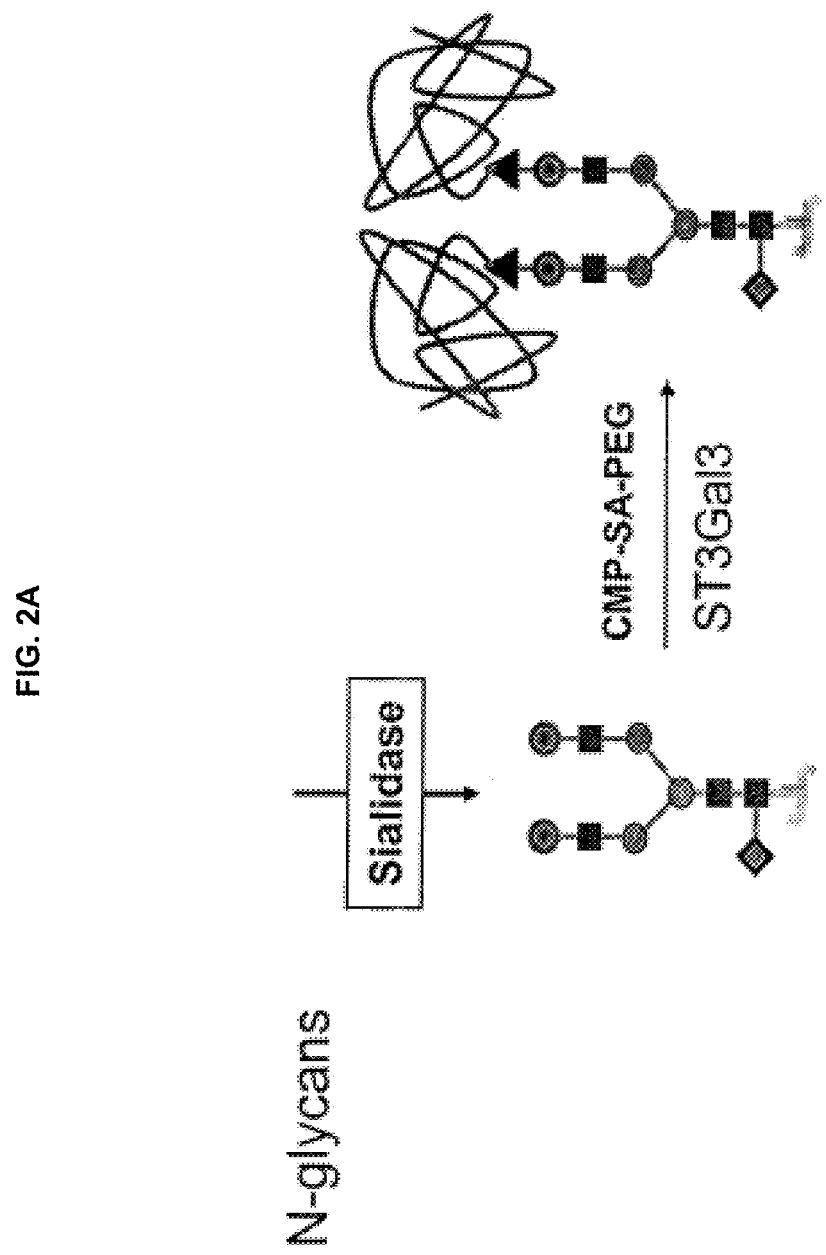
Figure 2D:
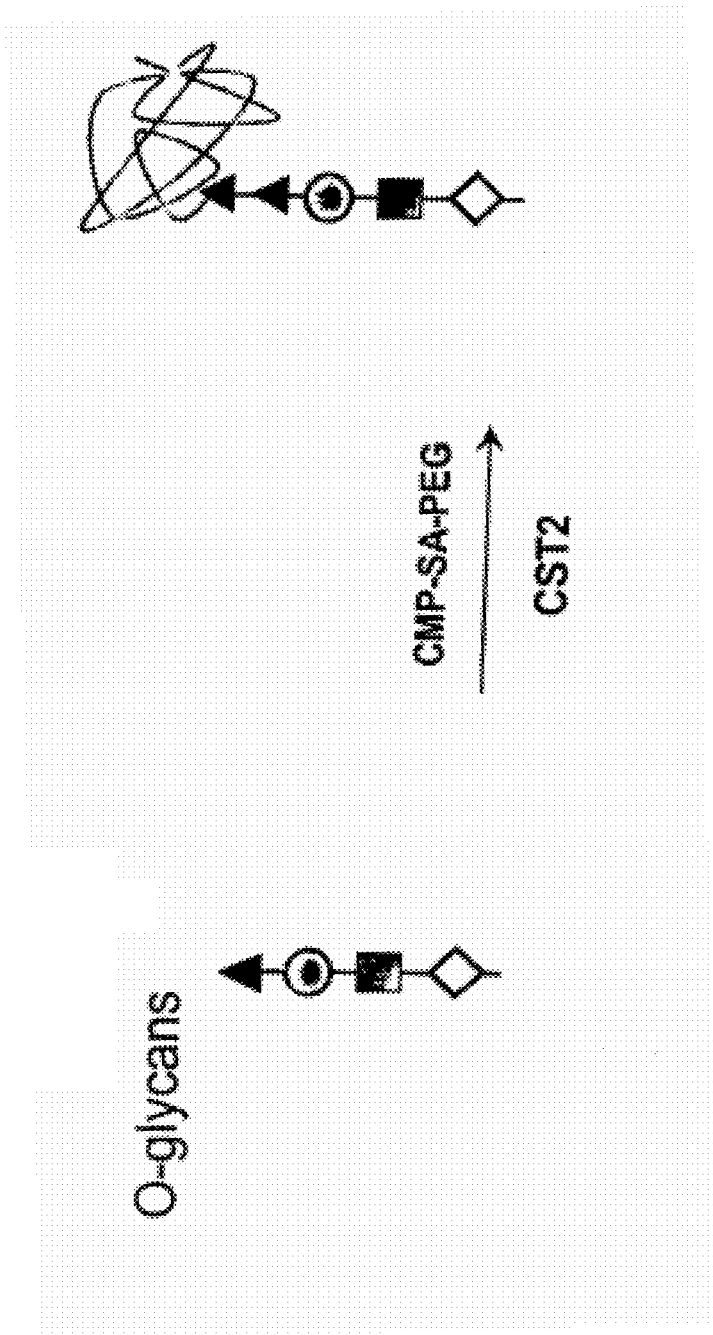
Figure 2E:
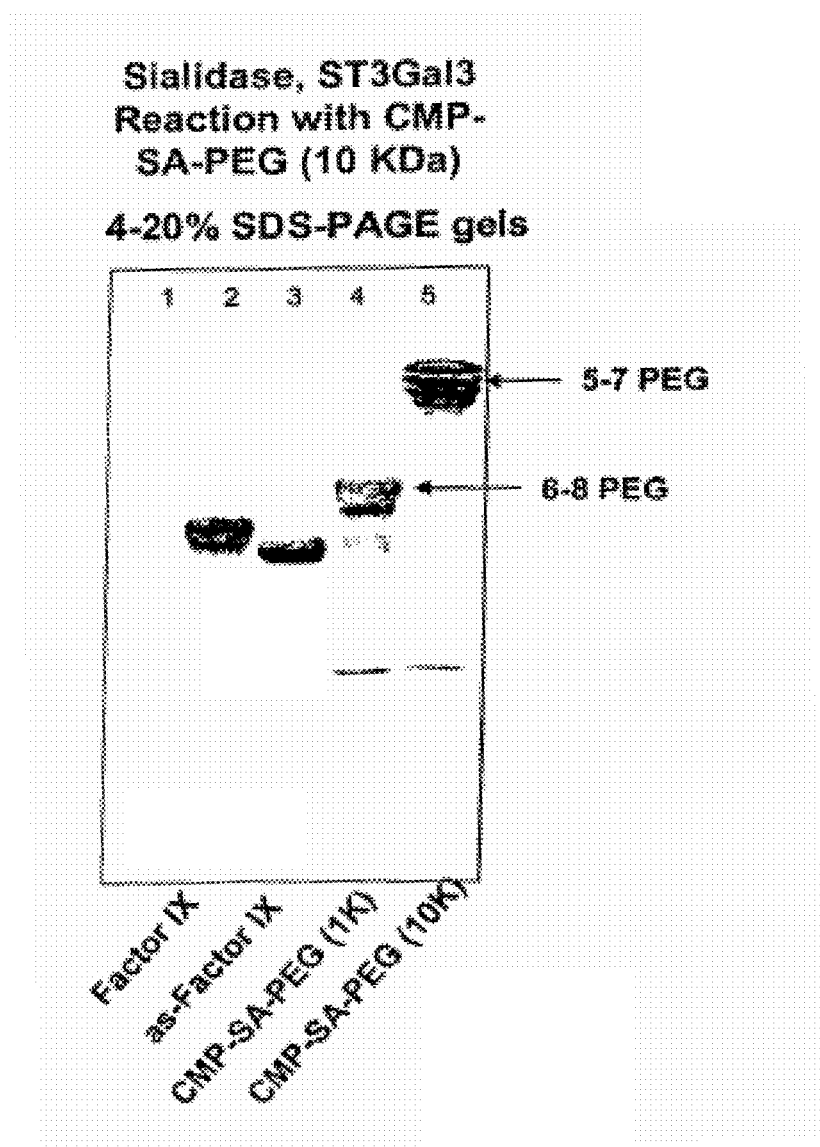
FIGS. 2E-F are SDS-PAGE gels of glycopegylated Factor IX according to such schemes.
Figure 2F:
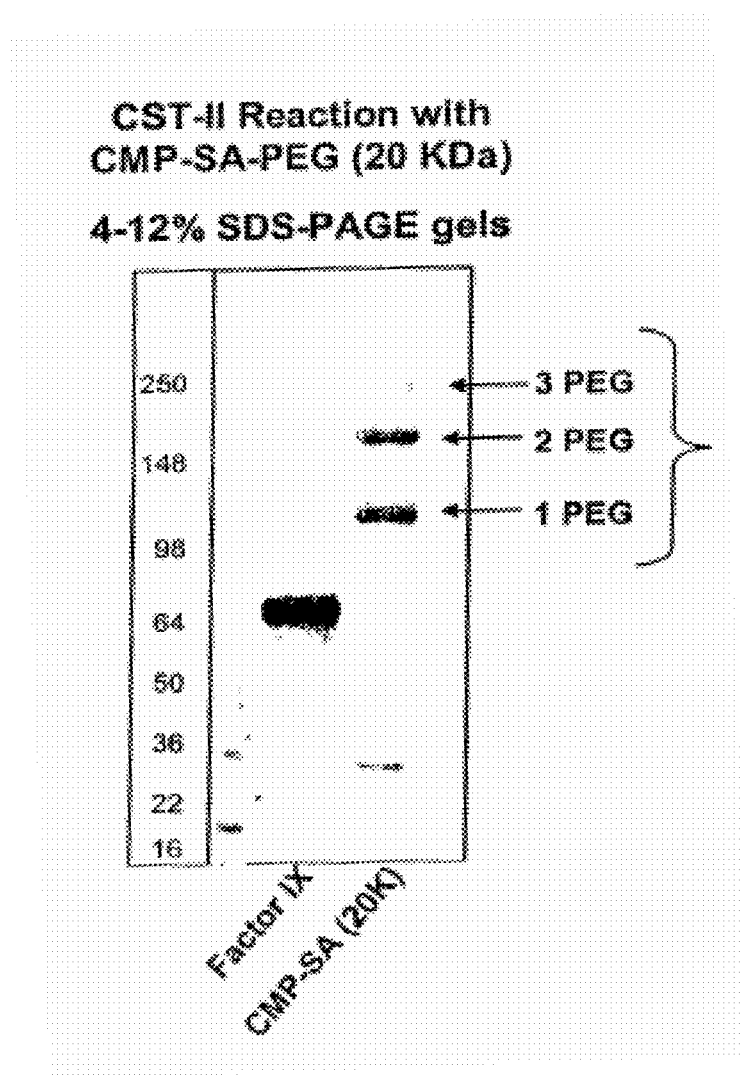
Figure 3:
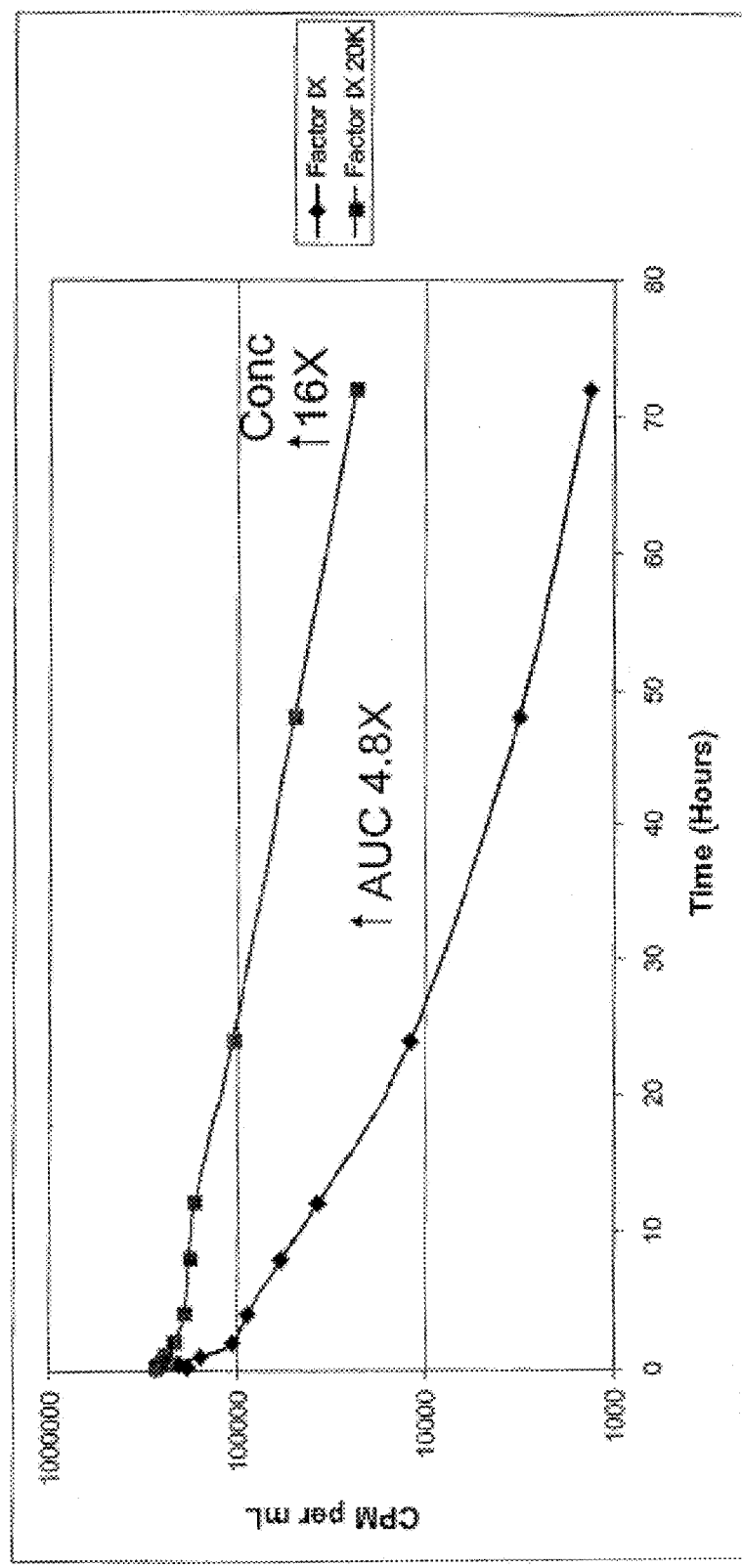
FIG. 3 is a plot comparing the in vivo residence lifetimes of unglycosylated Factor IX and enzymatically glycopegylated Factor IX.
Figure 6:
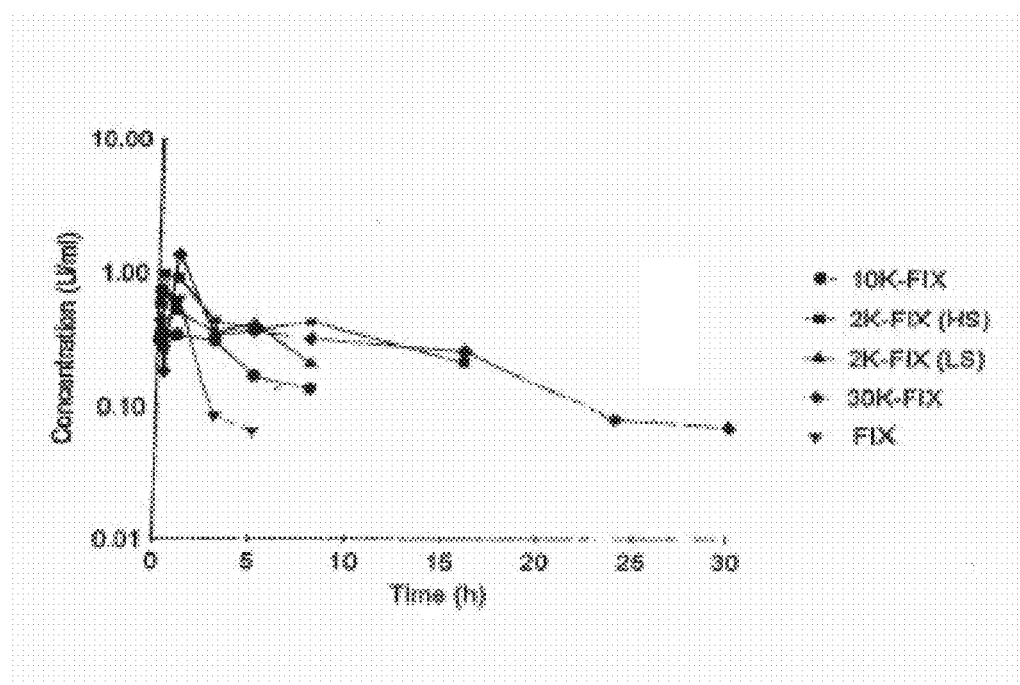
FIG. 6 is a graphic presentation of the pharmacokinetic properties of various glycopegylated Factor IX molecules compared to a non-pegylated Factor IX.
Figure 7:
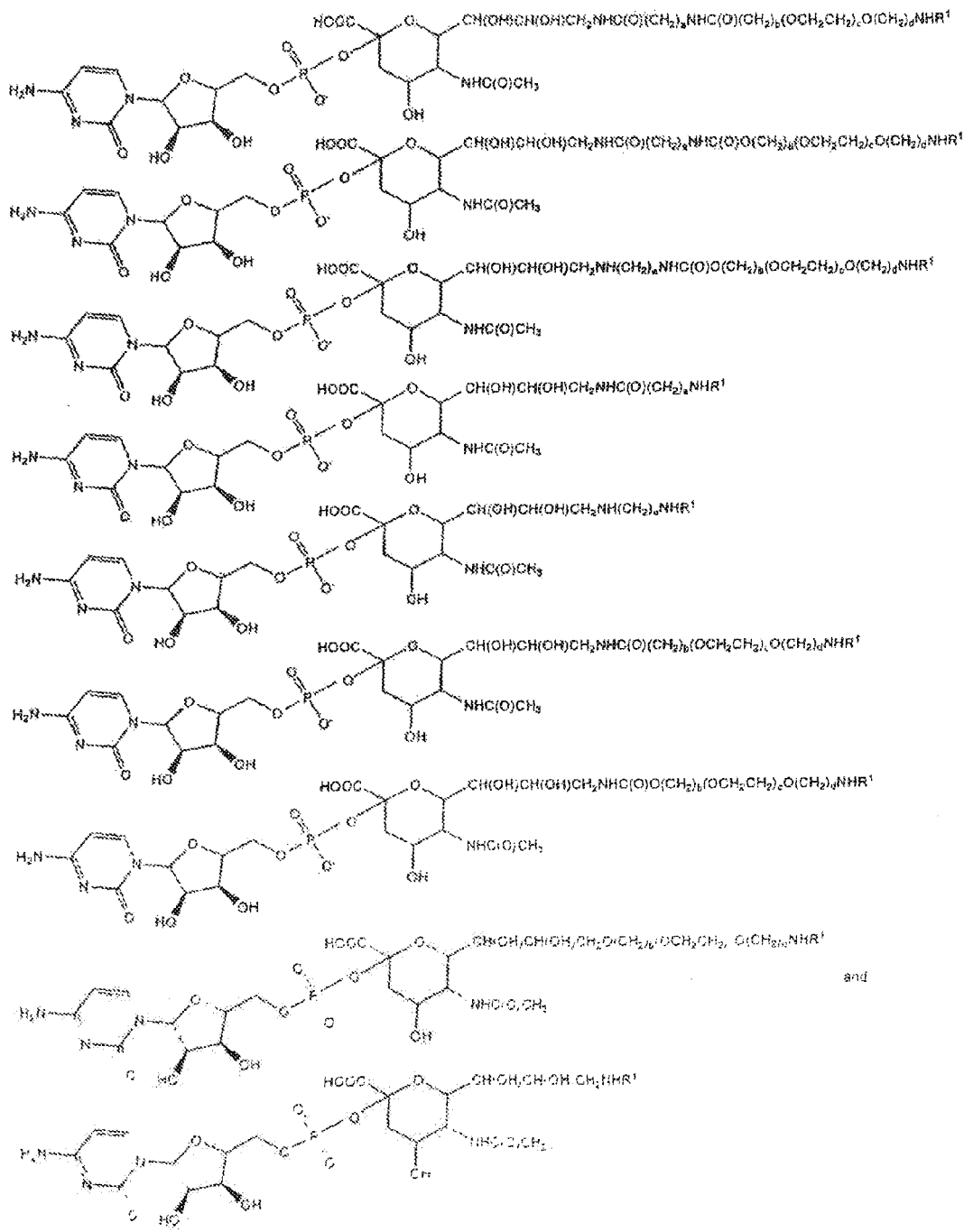
FIG. 7 is a table of representative modified sugar species of use in the present invention.
Figure 8:
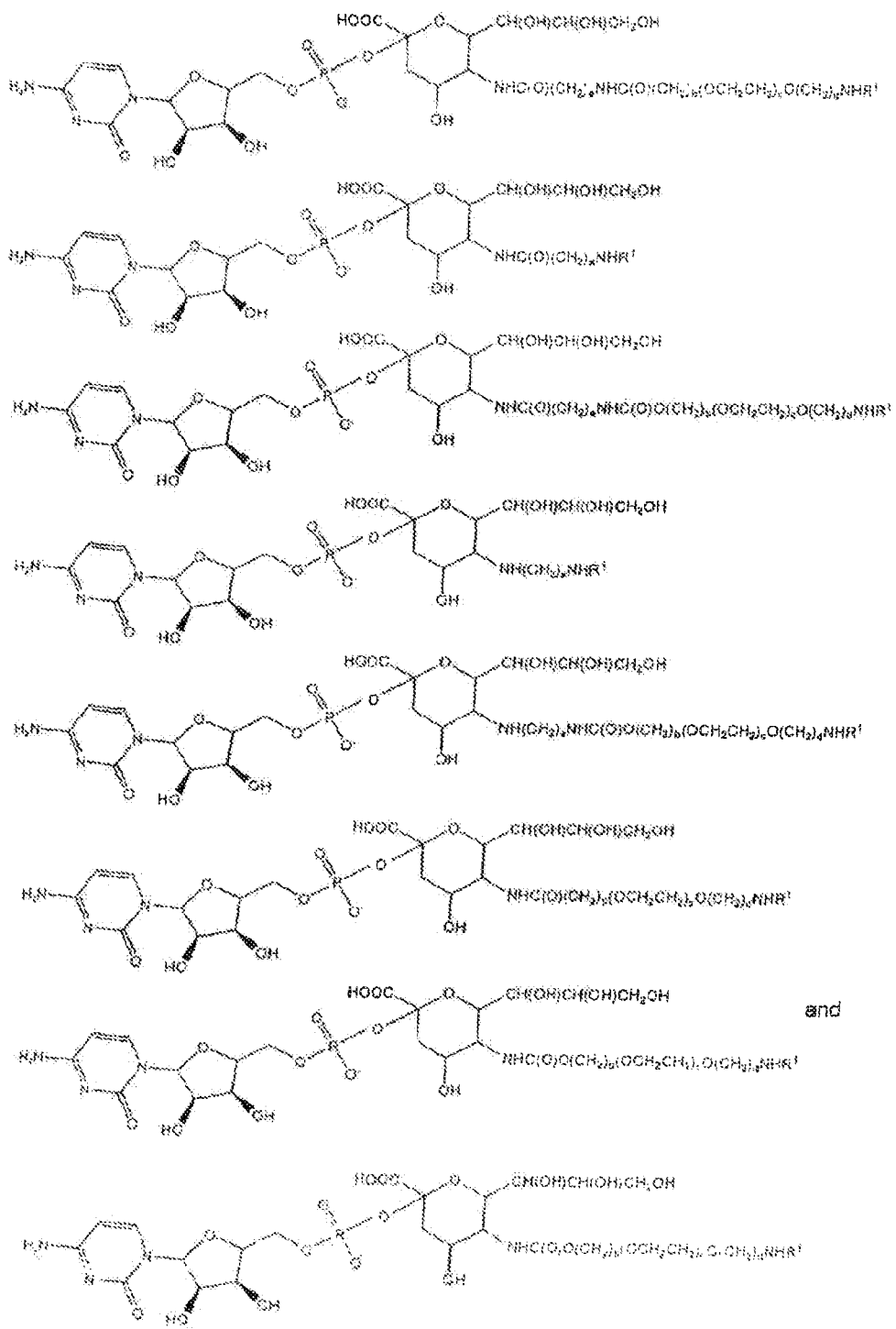
FIG. 8 is a table of representative modified sugar species of use in the present invention.
Figure 10:
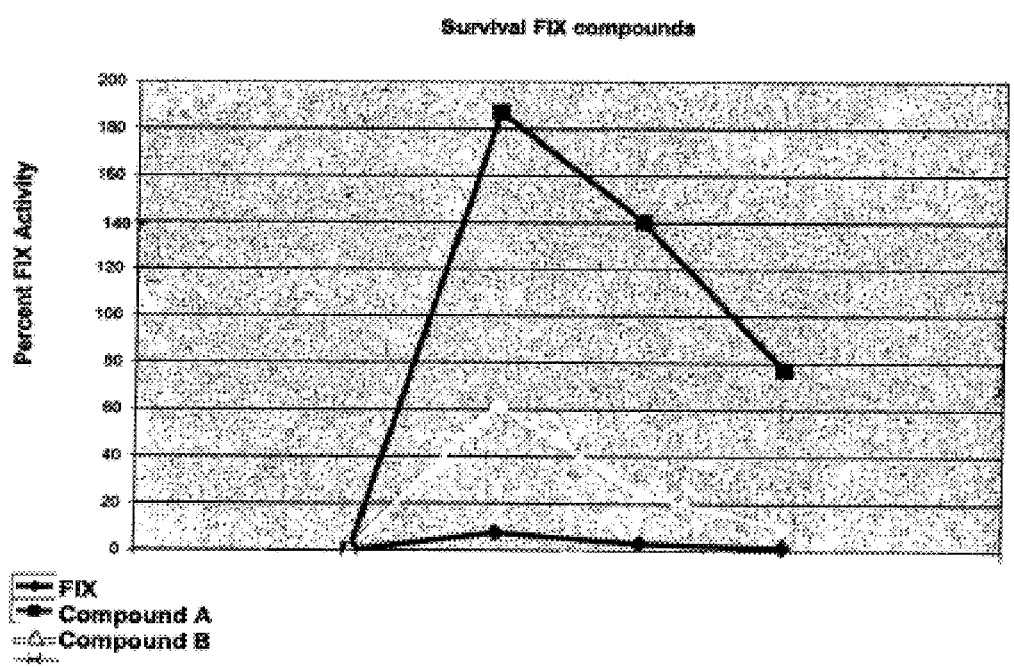
FIG. 10 is a time-course plot comparing the in vivo activity of a Factor IX glycoconjugate with 30 kD PEG (Neose A), a Factor IX glycoconjugate with 2 kD PEG (Neose B) and unconjugated Factor IX.
Figure 11:
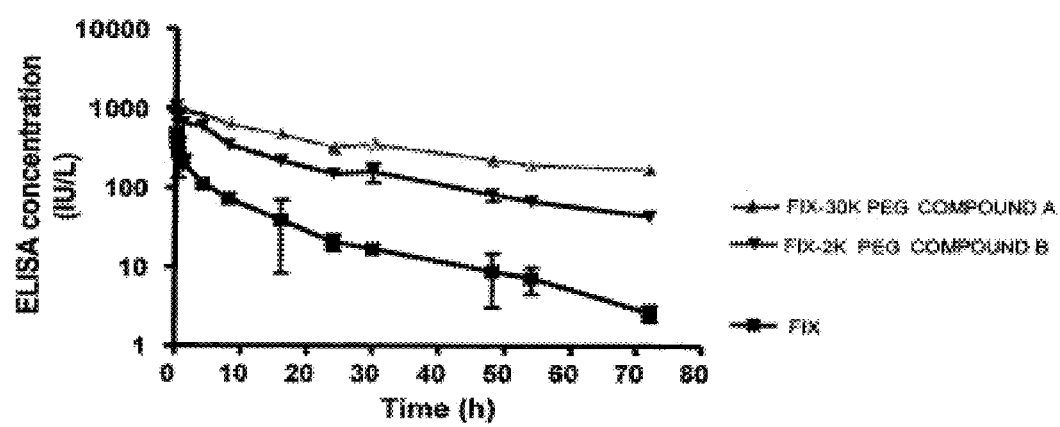
FIG. 11 is a plot of in vivo concentration of rhFIX, glycoPEGylated FIX (30 kD sialic acid; Compound A), glycoPEGylated FIX (2 kD sialic acid; Compound B) measured by an ELISA assay.

PEG, poly(ethylene glycol); PPG, poly(propylene glycol); Ara, arabinosyl; Fm, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; NeuAc (N-acetylneuraminyl), Sia (sialyl); M6P, mannose-6-phosphate.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature, see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "modified sugar," refers to a naturally- or non-naturally-occurring carbohydrate that is enzymatically added onto an amino acid or a glycosyl residue of a peptide in a process of the invention. The modified sugar is selected from enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)$_m$, in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius<2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives will vary depending upon the size, state of glycosylation, and other parameters, as is well known in the art. Further explanation of "half-life" is found in Pharmaceutical Biotechnology (1997, D F A Crommelin and R D Sindelar, eds., Harwood Publishers, Amsterdam, pp 101-120).

The term "terminal half life" or "terminal $T_{1/2}$," refers to the effective half-life of the elimination phase. For example, for the two compartment model, the beta phase constant (beta=elimination constant) can be used to calculate the half-life of the elimination phase, e.g., $T_{1/2}$=0.693/beta.

The term "recovery" refers to a quantity determined from the peak factor level that occurs in the first hour post-administration. This figure should be reported as an incremental value, i.e., after subtracting the baseline (pre-administration) level and then reported on a per dosage basis as (U/mL)/(U/kg). See, Lee et al., *Hemophilia* (2006), 12, (Suppl. 3), 1-7.

The term "glycoconjugation," as used herein, refers to the enzymatically mediated conjugation of a modified sugar species to an amino acid or glycosyl residue of a polypeptide, e.g., a Factor IX peptide of the present invention. A subgenus of "glycoconjugation" is "glycol-PEGylation," in which the modifying group of the modified sugar is poly(ethylene glycol), and alkyl derivative (e.g., m-PEG) or reactive derivative (e.g., $H_2N$-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins. Exemplary proteins include, but are not limited to, Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal for treating a disease, is sufficient to effect treatment for that disease.

The term "isolated" refers to a material that is substantially or essentially free from components, which are used to produce the material. For peptide conjugates of the invention, the term "isolated" refers to material that is substantially or essentially free from components which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$, —S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—OCH$_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R')=NR''', —S(O)R', —S(O)$_2$R', —S(O)$_2$NR'R", —NRSO$_2$R', —CN and —$NO_2$, —R', —$N_3$, —$CH(Ph)_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

Introduction

As described above, Factor IX is vital in the blood coagulation cascade. A deficiency of Factor IX in the body characterizes a type of hemophilia (type B). Treatment of this disease is usually limited to intravenous transfusion of human plasma protein concentrates of Factor IX. However, in addition to the practical disadvantages of time and expense, transfusion of blood concentrates involves the risk of transmission of viral hepatitis, acquired immune deficiency syndrome or thromboembolic diseases to the recipient.

While Factor IX is an important and useful compound for therapeutic applications, present methods for the production of Factor IX from recombinant cells (U.S. Pat. No. 4,770,999) result in a product with a rather short biological half-life and an inaccurate glycosylation pattern that could potentially lead to immunogenicity, loss of function, an increased need for both larger and more frequent doses in order to achieve the same effect, and the like.

To improve the effectiveness of recombinant Factor IX used for therapeutic purposes, the present invention provides conjugates of glycosylated and unglycosylated Factor IX peptides with polymers, e.g., PEG (m-PEG), PPG (m-PPG), etc. The conjugates may be additionally or alternatively modified by further conjugation with diverse species such as therapeutic moieties, diagnostic moieties, targeting moieties and the like.

The conjugates of the invention are formed by the enzymatic reaction of a modified sugar with the glycosylated or unglycosylated peptide. A glycosylation site and/or a glycosyl residue provides a locus for conjugating a sugar bearing a modifying group to the peptide, e.g., by glycoconjugation. An exemplary modifying group is a water-soluble polymer, such as poly(ethylene glycol), e.g., methoxy-poly(ethylene glycol). Modification of the Factor IX peptides, e.g., with a water-soluble peptide can improve the stability and retention time of the recombinant Factor IX in a patient's circulation, and/or reduce the antigenicity of recombinant Factor IX.

The methods of the invention make it possible to assemble peptide conjugates that have a substantially homogeneous derivatization pattern. The enzymes used in the invention are generally selective for a particular amino acid residue, combination of amino acid residues, or particular glycosyl residues of the peptide. The methods are also practical for large-scale production of modified peptide conjugates. Thus, the methods of the invention provide a practical means for large-scale preparation of glycopeptides having preselected uniform derivatization patterns.

The present invention also provides conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

Peptide Conjugates

Conjugates between FIX peptides and water-soluble polymers, e.g., PEG, are known to be significantly less effective in standard coagulation assays than the corresponding unconjugated FIX peptide. Thus, the discovery that FIX peptides conjugated with a water-soluble polymer have an activity in a coagulation assay that is significantly enhanced relative to the corresponding unconjugated FIX is an important and surprising result. The present invention provides FIX conjugates with water-soluble polymers that exhibit enhanced activity relative to the corresponding unconjugated FIX peptide in standard coagulation assays.

Thus, in a first aspect, the instant invention provides a conjugate between a FIX peptide and a water-soluble polymer that has coagulation activity that is enhanced relative to that of a FIX peptide that is not conjugated with a water-soluble polymer. In a preferred embodiment, the unconjugated peptide and the peptide of the conjugate have identical amino acid sequences. In another preferred embodiment, the conjugated and unconjugated peptide are more than about 90% homologous, preferably, more than about 95% homologous, more preferably, more than about 97% homologous and even more preferably, more than about 99% homologous.

In a preferred embodiment, the water-soluble polymer is a linear or branched PEG. It is generally preferred that the conjugates include from 1 to about 9 PEG moieties per peptide. In a preferred embodiment, the water-soluble polymer is a linear PEG and the conjugate includes approximately 6 to 8 PEG moieties per peptide molecule. In another preferred embodiment, the water-soluble polymer is a branched PEG and the conjugate includes approximately 1 to 5 PEG moieties per peptide molecule. In yet another preferred embodiment, the water-soluble polymer is a branched PEG and the conjugate includes approximately 2 PEG moieties per peptide molecule. In yet another preferred embodiment, the water-soluble polymer is a branched PEG and the conjugate includes approximately 1 PEG moiety per peptide molecule.

In exemplary embodiments, in which the PEG is a linear species, the PEG moiety has a molecular weight which is from about 200 D to about 20 kD. In preferred embodiments, in which the PEG moiety is a linear PEG moiety, the molecular weight of the linear PEG is at least about 200 D, more preferably, at least about 500 D, even more preferably, at least about 1 kD, more preferably, at least about 2 kD.

In other exemplary embodiments in which the PEG species is branched, the branched PEG includes from 2 to 6 linear PEG arms. Exemplary PEG arms have a molecular weight from about 200 D to about 30 kD. In an exemplary embodiment, the PEG species is branched and has a molecular weight of about 40 kD. It is generally preferred that each arm has an individually selected molecular weight that is at least about 2 kD, preferably, at least about 5 kD, more preferably, at least about 10 kD, still more preferably, at least about 15 kD, and even more preferably about 20 kD.

A preferred PEG species has two PEG arms. A presently preferred embodiment of the two-arm branched structure is based on an amino acid. Preferred amino acids include serine, cysteine and lysine.

In a preferred embodiment, the FIX conjugate of the invention has an in vivo coagulation activity that is at least about 15% greater than the activity of an identical nonconjugated peptide at a 24 hour time point in an in vivo coagulation assay. Preferred Factor IX conjugates of the invention exhibit a coagulation activity at a 24 hour time point that is enhanced over the identical nonconjugated peptide by at least about 40%, preferably, at least about 60%, more preferably, at least about 80%, even more preferably, at least about 100%, still more preferably, at least about 150%, and even more preferably, at least about 200%.

A presently preferred conjugate includes from 1-4 branched PEG moieties, in which the branched PEG is based upon an amino acid (i.e., the PEG arms are covalently linked to an amino acid core). This conjugate preferably has an activity that is enhanced at a 24 hour time point by at least about 100%, preferably, at least about 120%, more preferably, at least about 140%, still more preferably, at least about 160%, even more preferably, at least about 180% and more preferably, at least about 200% over the activity of the identical unconjugated FIX peptide in the same assay. In this embodiment, the branched PEG species have a molecular weight of at least about 15 kD, preferably, at least about 20, kD, and more preferably, at least about 30 kD. A preferred branched PEG species has a molecular weight of about 30 kD: even more preferred, the branched PEG species includes two linear PEG moieties covalently attached to an amino acid which is a member selected from lysine, serine and cysteine. Each branched PEG moiety is covalently attached to an amino acid or a glycosyl residue of the Factor IX peptide.

Another preferred conjugate of the invention includes from 5 to 9, more preferably, from 6 to 8 linear PEG moieties. In this embodiment, the PEG moieties have a molecular weight that is at least about 500 D, preferably, at least about 1 kD, more preferably, at least about 1.5 kD and, still more preferably, at least about 2 kD. The linear PEG moieties are covalently conjugated to an amino acid or glycosyl residue of the peptide. The conjugates according to this embodiment preferably have an activity enhanced by at least about 15%, preferably, at least about 25%, more preferably, at least about 35%, even more preferably, at least about 45%, and still more preferably, at least about 60% relative to an identical unconjugated FIX peptide in the same assay.

In another preferred embodiment, the branched or linear PEG species is covalently attached to an amino acid or glycosyl residue of the peptide. The PEG species are preferably attached to a sialic acid moiety of a glycosyl residue. When the PEG species are attached to an amino acid, they are preferably attached through a linker moiety to an amino acid which is a member selected from lysine, asparagine, serine and threonine. A generally preferred linker structure includes at least one glycosyl moiety. Additional embodiments in which the linking group is a glycosyl residue or includes at least one glycosyl moiety are discussed in detail in the sections that follow.

In a preferred embodiment, the water-soluble polymer is attached to a member selected from Asn 157, Asn 167; Ser 53, Ser 61, Thr 159, Thr 169, and Thr 172 of rhFIX.

The coagulation activities of the conjugated and unconjugated peptides are readily and routinely measured using art-standard coagulation assay methods, e.g., a standard mouse tail cut assay, aPTT assay, etc.

In another preferred embodiment, the conjugated FIX peptide has a terminal half life that is at least about 10% greater, preferably, at least about 30% greater, more preferably, at least about 50% greater, still more preferably, at least about 70% greater, and even more preferably at least about 100% greater than the terminal half-life of the identical unconjugated FIX peptide.

In each of the aspects and embodiments of the invention discussed herein, the Factor IX peptide may have the same sequence as a wild-type FIX peptide, or it may be a mutant peptide. A peptide conjugate can have one of several forms. In an exemplary embodiment, a peptide conjugate can comprise a Factor IX peptide and a modifying group linked to an amino acid of the peptide. In an exemplary embodiment, this modifying group is attached to the Factor IX peptide through a glycosyl linking group.

Thus, in a second aspect, the present invention provides a conjugate between a modified sugar and a Factor IX peptide.

In an exemplary embodiment, the glycosyl group is an intact glycosyl linking group. In another exemplary embodiment, the glycosyl group further comprises a modifying group. In another exemplary embodiment, the modifying group is a non-glycosidic modifying group. In another exemplary embodiment, the modifying group does not include a naturally occurring saccharide moiety.

In another exemplary embodiment, the peptide conjugate can comprise a Factor IX peptide and a glycosyl linking group which is bound to both a glycopeptide carbohydrate and directly to an amino acid residue of the peptide backbone. In yet another exemplary embodiment, a peptide conjugate can comprise a Factor IX peptide and a modifying group linked directly to an amino acid residue of the peptide. In this embodiment, the peptide conjugate may not comprise a glycosyl group. In any of these embodiments, the Factor IX peptide may or not be glycosylated. The present invention also encompasses a method for the modification of the glycan structure on Factor IX, providing a conjugate between Factor IX and a modifying group.

The conjugates of the invention will typically correspond to the general structure:

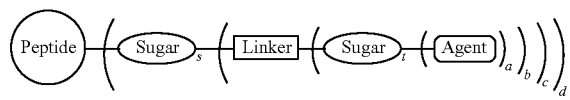

in which the symbols a, b, c, d and s represent a positive, non-zero integer; and t is either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

Factor IX Peptide

Factor IX has been cloned and sequenced. Essentially any Factor IX peptide having any sequence is of use as the Factor IX peptide component of the conjugates of the present invention. In an exemplary embodiment, the peptide has the sequence presented herein as SEQ ID NO:1:

YNSGKLEEFVQGNLERECMEEKCSFEEAREVFENTERTTEFWKQYVDG

DQCESNPCLNGGSCKDDINSYECWCPFGFEGKNCELDVTCNIKNGRCE

QFCKNSADNKVVCSCTEGYRLAENQKSCEPAVPFPCGRVSVSQTSKLT

RAEAVFPDVDYVNSTEAETILDNITQSTQSFNDFTRVVGGEDAKPGQF

PWQVVLNGKVDAFCGGSIVNEKWIVTAAHCVETGVKITVVAGEHNIEE

TEHTEQKRNVIRIIPHHNYNAAINKYNHDIALLELDEPLVLNSYVTPI

CIADKEYTNIFLKFGSGYVSGWGRVFHKGRSALVLQYLRVPLVDRATC

LRSTKFTIYNNMFCAGFHEGGRDSCQGDSGGPHVTEVEGTSFLTGIIS

WGEECAMKGKYGIYTKVSRYVNWIKEKTKLT.

The present invention is in no way limited to the sequence set forth herein. Factor IX variants are well known in the art, as described in, for example, U.S. Pat. Nos. 4,770,999, 5,521, 070 in which a tyrosine is replaced by an alanine in the first position, U.S. Pat. No. 6,037,452, in which Factor IX is linked to an alkylene oxide group, and U.S. Pat. No. 6,046,380, in which the DNA encoding Factor IX is modified in at least one splice site. As demonstrated herein, variants of Factor IX are well known in the art, and the present disclosure encompasses those variants known or to be developed or discovered in the future.

Methods for determining the activity of a mutant or modified Factor IX can be carried out using the methods described in the art, such as a one stage activated partial thromboplastin time assay as described in, for example, Biggs, *Human Blood Coagulation Haemostasis and Thrombosis* (Ed. 1), Oxford, Blackwell, Scientific, pg. 614 (1972). Briefly, to assay the biological activity of a Factor IX molecule developed according to the methods of the present invention, the assay can be performed with equal volumes of activated partial thromboplastin reagent, Factor IX deficient plasma isolated from a patient with hemophilia B using sterile phlebotomy techniques well known in the art, -and normal pooled plasma as standard, or the sample. In this assay, one unit of activity is defined as that amount present in one milliliter of normal pooled plasma. Further, an assay for biological activity based on the ability of Factor IX to reduce the clotting time of plasma from Factor IX-deficient patients to normal can be performed as described in, for example, Proctor and Rapaport (*Amer. J. Clin. Path.* 36: 212 (1961).

The peptides of the invention include at least one N-linked or O-linked glycosylation site, at least one of which is conjugated to a glycosyl residue that includes a polymeric modifying moiety, e.g., a PEG moiety. In an exemplary embodiment, the PEG is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which the glycosyl linking group is attached to both an amino acid residue and a glycosyl residue.

Preferably, neither the amino nor the carboxy terminus of the Factor IX peptide is derivatized with a polymeric modifying moiety.

Modified Sugar

In an exemplary embodiment, the peptides of the invention are reacted with a modified sugar, thus forming a peptide conjugate. A modified sugar comprises a "sugar donor moiety" as well as a "sugar transfer moiety". The sugar donor moiety is any portion of the modified sugar that will be attached to the peptide, either through a glycosyl moiety or amino acid moiety, as a conjugate of the invention. The sugar donor moiety includes those atoms that are chemically altered during their conversion from the modified sugar to the glycosyl linking group of the peptide conjugate. The sugar transfer moiety is any portion of the modified sugar that will be not be attached to the peptide as a conjugate of the invention. For example, a modified sugar of the invention is the PEGylated sugar nucleotide, CMP-SA-PEG. For CMP-SA-PEG, the sugar donor moiety, or PEG-sialyl donor moiety, comprises PEG-sialic acid while the sugar transfer moiety, or sialyl transfer moiety, comprises CMP.

In modified sugars of use in the invention, the saccharyl moiety is preferably a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the saccharyl moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any saccharyl moiety can be utilized as the sugar donor moiety of the modified sugar. The saccharyl moiety can be a known sugar, such as mannose, galactose or glucose, or a species having the stereochemistry of a known sugar. The general formulae of these modified sugars are:

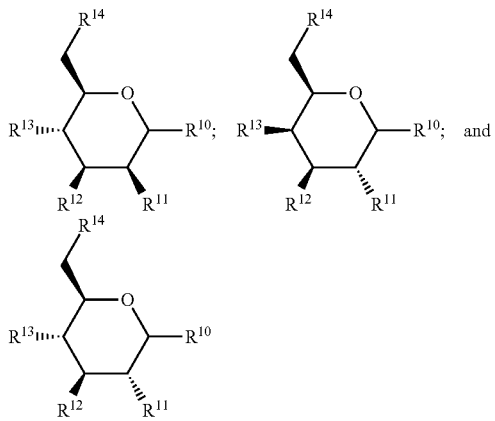

Other saccharyl moieties that are useful in forming the compositions of the invention include, but are not limited to fucose and sialic acid, as well as amino sugars such as glucosamine, galactosamine, mannosamine, the 5-amine analogue of sialic acid and the like. The saccharyl moiety can be a structure found in nature or it can be modified to provide a site for conjugating the modifying group. For example, in one embodiment, the modified sugar provides a sialic acid derivative in which the 9-hydroxy moiety is replaced with an amine. The amine is readily derivatized with an activated analogue of a selected modifying group.

Examples of modified sugars of use in the invention are described in PCT Patent Application No. PCT/US05/002522, which is herein incorporated by reference.

In a further exemplary embodiment, the invention utilizes modified sugars in which the 6-hydroxyl position is converted to the corresponding amine moiety, which bears a linker-modifying group cassette such as those set forth above. Exemplary glycosyl groups that can be used as the core of these modified sugars include Gal, GalNAc, Glc, GlcNAc, Fuc, Xyl, Man, and the like. A representative modified sugar according to this embodiment has the formula:

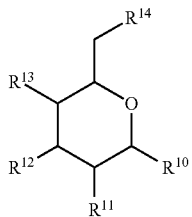

in which $R^{11}$-$R^{14}$ are members independently selected from H, OH, C(O)CH$_3$, NH, and NH C(O)CH$_3$. $R^{10}$ is a link to another glycosyl residue (—O-glycosyl) or to an amino acid of the Factor IX and/or Factor IX peptide (—NH— (Factor IX and/or Factor IX)). $R^{14}$ is $OR^1$, $NHR^1$ or NH-L-$R^1$. $R^1$ and NH-L-$R^1$ are as described above.

Glycosyl Linking Groups

In an exemplary embodiment, the invention provides a peptide conjugate formed between a modified sugar of the invention and a Factor IX peptide. In this embodiment, the sugar donor moiety (such as the saccharyl moiety and the modifying group) of the modified sugar becomes a "glycosyl linking group". The "glycosyl linking group" can alternatively refer to the glycosyl moiety which is interposed between the peptide and the modifying group.

Due to the versatility of the methods available for adding and/or modifying glycosyl residues on a peptide, the glycosyl linking groups can have substantially any structure. In the discussion that follows, the invention is illustrated by reference to the use of selected derivatives of furanose and pyranose. Those of skill in the art will recognize that the focus of the discussion is for clarity of illustration and that the structures and compositions set forth are generally applicable across the genus of glycosyl linking groups and modified sugars. The glycosyl linking group can comprise virtually any mono- or oligo-saccharide. The glycosyl linking groups can be attached to an amino acid either through the side chain or through the peptide backbone. Alternatively the glycosyl linking groups can be attached to the peptide through a saccharyl moiety. This saccharyl moiety can be a portion of an O-linked or N-linked glycan structure on the Factor IX peptide.

In an exemplary embodiment, the invention utilizes a glycosyl linking group that has the formula:

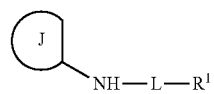

in which J is a glycosyl moiety, L is a bond or a linker and $R^1$ is a modifying group, e.g., a polymeric modifying group. Exemplary bonds are those that are formed between an $NH_2$ moiety on the glycosyl moiety and a group of complementary reactivity on the modifying group. For example, when $R^1$ includes a carboxylic acid moiety, this moiety may be activated and coupled with the $NH_2$ moiety on the glycosyl residue affording a bond having the structure $NHC(O)R^1$. J is preferably a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the species of the invention, e.g., between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

An exemplary species of NH-L-$R^1$ has the formula: —NH{C(O)(CH$_2$)$_a$NH}$_s${C(O)(CH$_2$)$_b$(OCH$_2$CH$_2$)$_c$—O—(CH$_2$)$_d$NH}$_t$$R^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —CH$_2$. As those of skill will appreciate one or more of the bracketed moieties corresponding to indices s and t can be replaced with a substituted or unsubstituted alkyl or heteroalkyl moiety.

More particularly, the invention utilizes compounds in which NH-L-$R^1$ is: NHC(O)$(CH_2)_a$NHC(O)$(CH_2)_b$ $(OCH_2CH_2)_cO(CH_2)_d$NH$R^1$, NHC(O)$(CH_2)_b$(OCH$_2$CH$_2$)$_c$O(CH$_2$)$_d$NH$R^1$, NHC(O)O(CH$_2$)$_b$(OCH$_2$CH$_2$)$_c$O(CH$_2$)$_d$NH$R^1$, NH(CH$_2$)$_a$NHC(O)(CH$_2$)$_b$(OCH$_2$CH$_2$)$_c$O(CH$_2$)$_d$NH$R^1$, NHC(O)(CH$_2$)$_a$NH$R^1$, NH(CH$_2$)$_a$NH$R^1$, and NH$R^1$. In these formulae, the indices a, b and d are independently selected from the integers from 0 to 20, preferably from 1 to 5. The index c is an integer from 1 to about 2500.

In an exemplary embodiment, c is selected such that the PEG moiety is approximately 1 kD, 5 kD, 10, kD, 15 kD, 20 kD, 25 kD, 30 kD, 35 kD, 40 kD, 45 kD, 50 kD, 55 kD, 60 kD or 65 kD.

For the purposes of convenience, the glycosyl linking groups in the remainder of this section will be based on a sialyl moiety. However, one of skill in the art will recognize that another glycosyl moiety, such as mannosyl, galactosyl, glucosyl, or fucosyl, could be used in place of the sialyl moiety.

In an exemplary embodiment, the glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. In an exemplary embodiment, the invention provides a peptide conjugate comprising an intact glycosyl linking group having a formula that is selected from:

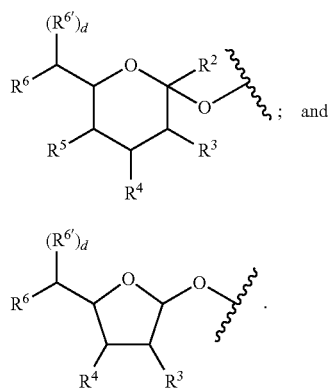

In Formulae I $R^2$ is H, CH$_2$O$R^7$, COO$R^7$ or O$R^7$, in which $R^7$ represents H, substituted or unsubstituted alkyl or substituted or unsubstituted heteroalkyl. When COO$R^7$ is a carboxylic acid or carboxylate, both forms are represented by the designation of the single structure COO$^-$ or COOH. In Formulae I and II, the symbols $R^3$, $R^4$, $R^5$, $R^6$ and $R^{6'}$ independently represent H, substituted or unsubstituted alkyl, O$R^8$, NHC(O) $R^9$. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes a modifying group. This modifying group can be a polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, the pyruvyl side chain is functionalized with the polymeric modifying group. In another exemplary embodiment, $R^6$ and $R^{6'}$, together with the carbon to which they are attached are components of the side chain of sialic acid and the polymeric modifying group is a component of $R^5$.

Exemplary modifying group-intact glycosyl linking group cassettes according to this motif are based on a sialic acid structure, such as those having the formulae:

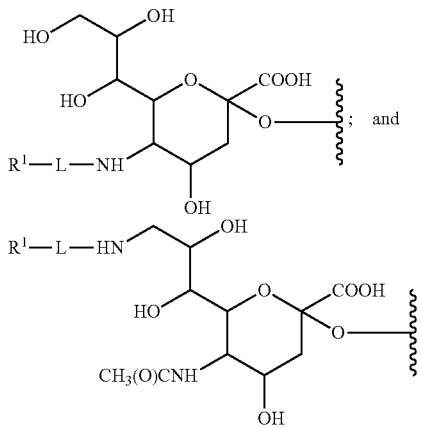

In the formulae above, $R^1$ and L are as described above. Further detail about the structure of exemplary $R^1$ groups is provided below.

In still a further exemplary embodiment, the conjugate is formed between a peptide and a modified sugar in which the modifying group is attached through a linker at the 6-carbon position of the modified sugar. Thus, illustrative glycosyl linking groups according to this embodiment have the formula:

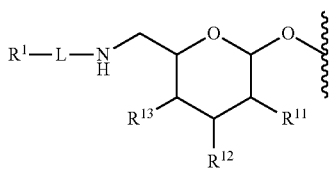

in which the radicals are as discussed above. Glycosyl linking groups include, without limitation, glucose, glucosamine, N-acetyl-glucosamine, galactose, galactosamine, N-acetyl-galactosamine, mannose, mannosamine, N-acetyl-mannosamine, and the like.

In one embodiment, the present invention provides a peptide conjugate comprising the following glycosyl linking group:

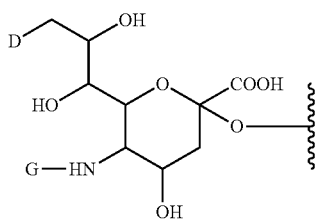

wherein D is a member selected from —OH and $R^1$-L-HN—; G is a member selected from H and $R^1$-L- and —C(O)(C$_1$-C$_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)($C_1$-$C_6$)alkyl, D is $R^1$-L-NH—.

The invention provides a peptide conjugate that includes a glycosyl linking group having the formula:

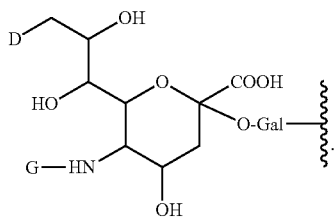

In other embodiments, the glycosyl linking group has the formula:

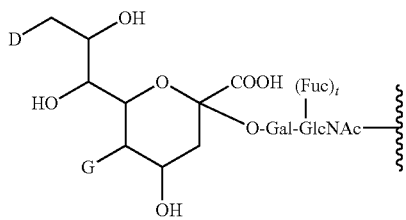

in which the index t is 0 or 1.

In a still further exemplary embodiment, the glycosyl linking group has the formula:

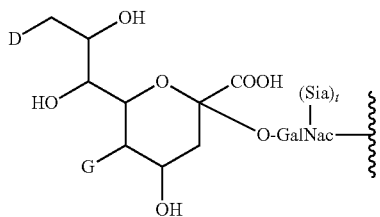

in which the index t is 0 or 1.

In yet another embodiment, the glycosyl linking group has the formula:

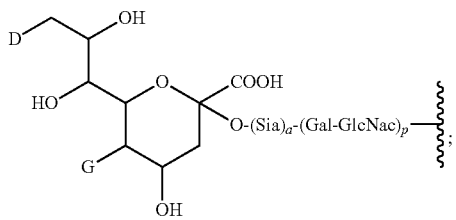

in which the index p represents and integer from 1 to 10; and a is either 0 or 1.

In an exemplary embodiment, a glycoPEGylated peptide conjugate of the invention selected from the formulae set forth below:

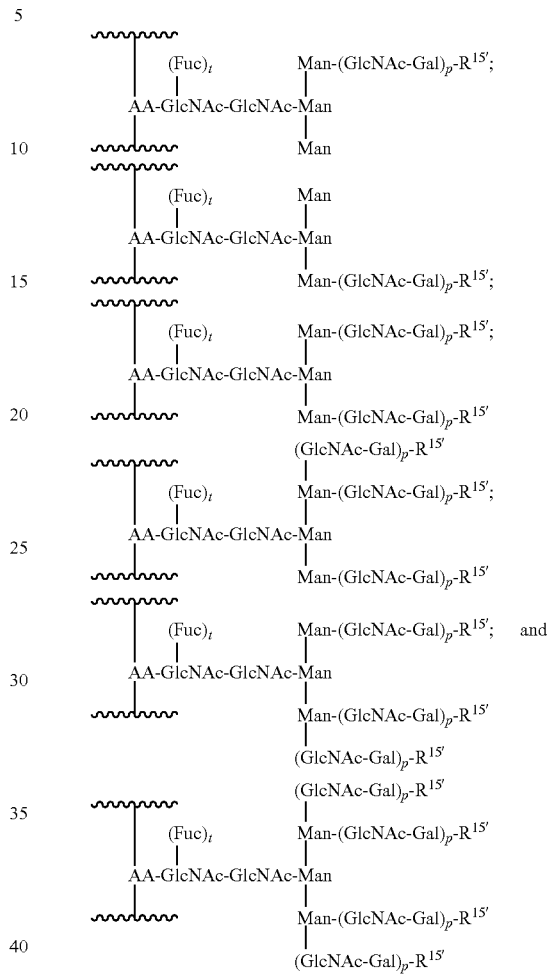

In the formulae above, the index t is an integer from 0 to 1 and the index p is an integer from 1 to 10. The symbol $R^{15'}$ represents H, OH (e.g., Gal-OH), a sialyl moiety, a sialyl linking group (i.e., sialyl linking group-polymeric modifying group (Sia-L-$R^1$), or a sialyl moiety to which is bound a polymer modified sialyl moiety (e.g., Sia-Sia-L-$R^1$) ("Sia-$Sia^{p'}$")). Exemplary polymer modified saccharyl moieties have a structure according to Formulae I and II. An exemplary peptide conjugate of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3-to the galactose residue. In another exemplary embodiment, the sialic acid is linked α2,6-to the galactose residue.

In an exemplary embodiment, the sialyl linking group is a sialyl moiety to which is bound a polymer modified sialyl moiety (e.g., Sia-Sia-L-$R^1$) ("Sia-$Sia^{p'}$"). Here, the glycosyl linking group is linked to a galactosyl moiety through a sialyl moiety:

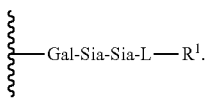

An exemplary species according to this motif is prepared by conjugating Sia-L-$R^1$ to a terminal sialic acid of a glycan using an enzyme that forms Sia-Sia bonds, e.g., CST-II, ST8Sia-II, ST8Sia-III and ST8Sia-IV.

In another exemplary embodiment, the glycans on the peptide conjugates have a formula that is selected from the group:

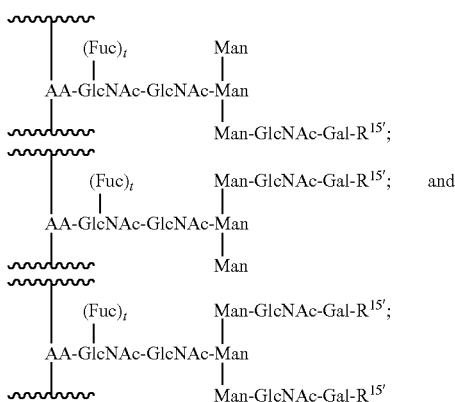

and combinations thereof.

In each of the formulae above, $R^{15'}$ is as discussed above. Moreover, an exemplary peptide conjugate of the invention will include at least one glycan with an $R^{15}$ moiety having a structure according to Formulae I or II.

In another exemplary embodiment, the glycosyl linking group comprises at least one glycosyl linking group having the formula:

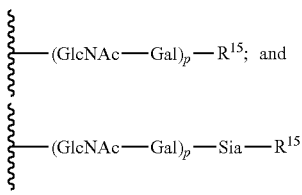

wherein $R^{15}$ is said sialyl linking group; and the index p is an integer selected from 1 to 10.

In an exemplary embodiment, the glycosyl linking moiety has the formula:

in which b is an integer from 0 to 1. The index s represents an integer from 1 to 10; and the index f represents an integer from 1 to 2500.

In an exemplary embodiment, the polymeric modifying group is PEG. In another exemplary embodiment, the PEG moiety has a molecular weight of about 20 kDa. In another exemplary embodiment, the PEG moiety has a molecular weight of about 5 kDa. In another exemplary embodiment, the PEG moiety has a molecular weight of about 10 kDa. In another exemplary embodiment, the PEG moiety has a molecular weight of about 40 kDa.

In an exemplary embodiment, the glycosyl linking group is a linear 10 kDa-PEG-sialyl, and one or two of these glycosyl linking groups are covalently attached to the peptide. In an exemplary embodiment, the glycosyl linking group is a branched 10 kDa-PEG-sialyl, and one or two of these glycosyl linking groups are covalently attached to the peptide. In an exemplary embodiment, the glycosyl linking group is a linear 20 kDa-PEG-sialyl, and one or two of these glycosyl linking groups are covalently attached to the peptide. In an exemplary embodiment, the glycosyl linking group is a branched 20 kDa-PEG-sialyl, and one or two of these glycosyl linking groups are covalently attached to the peptide. In an exemplary embodiment, the glycosyl linking group is a linear 5 kDa-PEG-sialyl, and one, two or three of these glycosyl linking groups are covalently attached to the peptide. In an exemplary embodiment, the glycosyl linking group is a branched 5 kDa-PEG-sialyl, and one, two or three of these glycosyl linking groups are covalently attached to the peptide. In an exemplary embodiment, the glycosyl linking group is a linear 40 kDa-PEG-sialyl, and one or two of these glycosyl linking groups are covalently attached to the peptide. In an exemplary embodiment, the glycosyl linking group is a branched 40 kDa-PEG-sialyl, and one or two of these glycosyl linking groups are covalently attached to the peptide.

Modifying Groups

The peptide conjugates of the invention comprise a modifying group. This group can be covalently attached to a FGF peptide through an amino acid or a glycosyl linking group. "Modifying groups" can encompass a variety of structures including targeting moieties, therapeutic moieties, biomolecules. Additionally, "modifying groups" include polymeric modifying groups, which are polymers which can alter a property of the peptide such as its bioavailability or its half-life in the body.

In an exemplary embodiment, the modifying group is a targeting agent that localizes selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood

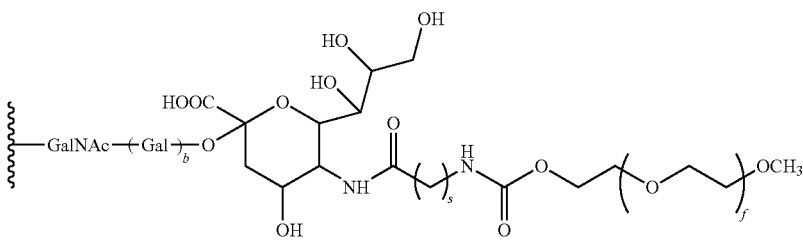

pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), and lipoprotein E.

For the purposes of convenience, the modifying groups in the remainder of this section will be largely based on polymeric modifying groups such as water soluble and water insoluble polymers. However, one of skill in the art will recognize that other modifying groups, such as targeting moieties, therapeutic moieties and biomolecules, could be used in place of the polymeric modifying groups.

Linkers of the Modifying Groups

The linkers of the modifying group serve to attach the modifying group (ie polymeric modifying groups, targeting moieties, therapeutic moieties and biomolecules) to the peptide. In an exemplary embodiment, the polymeric modifying group is bound to a glycosyl linking group, generally through a heteroatom, e.g., nitrogen, on the core through a linker, L, as shown below:

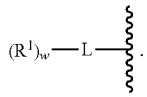

$R^1$ is the polymeric moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety.

An exemplary compound according to the invention has a structure according to Formulae I or II above, in which at least one of $R^2$, $R^3$, $R^4$, $R^5$, $R^6$ or $R^{6'}$ has the formula:

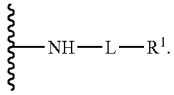

In another example according to this embodiment at least one of $R^2$, $R^3$, $R^4$, $R^5$, $R^6$ or $R^{6'}$ has the formula:

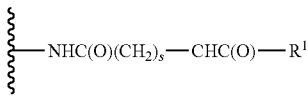

in which s is an integer from 0 to 20 and $R^1$ is a linear polymeric modifying moiety.

In an exemplary embodiment, the polymeric modifying group-linker construct is a branched structure that includes two or more polymeric chains attached to central moiety. In this embodiment, the construct has the formula:

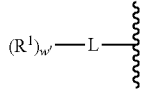

in which $R^1$ and L are as discussed above and w' is an integer from 2 to 6, preferably from 2 to 4 and more preferably from 2 to 3.

When L is a bond it is formed between a reactive functional group on a precursor of $R^1$ and a reactive functional group of complementary reactivity on the saccharyl core. When L is a non-zero order linker, a precursor of L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying group is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, $R^5$ includes the polymeric modifying group. In another exemplary embodiment, $R^5$ includes both the polymeric modifying group and a linker, L, joining the modifying group to the remainder of the molecule. As discussed above, L can be a linear or branched structure. Similarly, the polymeric modifying group can be branched or linear.

Water-Soluble Polymers

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids), e.g., poly(aspartic acid) and poly(glutamic acid); nucleic acids; synthetic polymers (e.g., poly(acrylic acid), poly (ethers), e.g., poly(ethylene glycol)); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Exemplary water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S.

Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly(ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly(ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

An exemplary water-soluble polymer is poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2000-60,000 is preferably used and preferably of from about 5,000 to about 40,000.

In other exemplary embodiments, the poly(ethylene glycol) molecule is selected from the following:

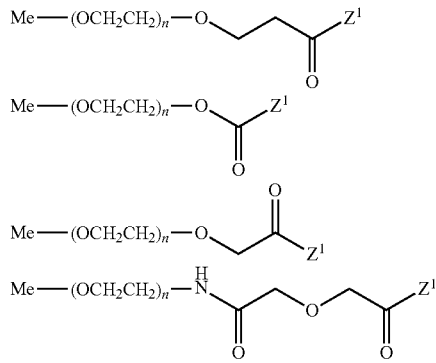

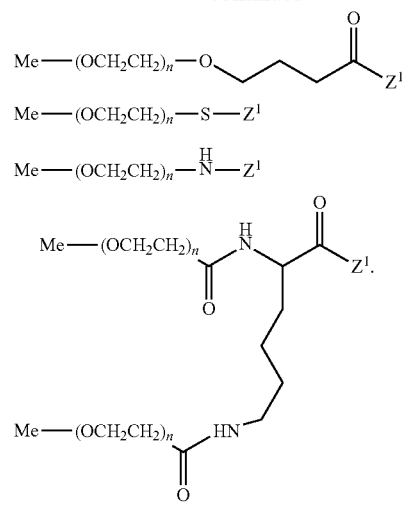

In another embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is less than or equal to 40,000 daltons.

Representative polymeric modifying moieties include structures that are based on side chain-containing amino acids, e.g., serine, cysteine, lysine, and small peptides, e.g., lys-lys. Exemplary structures include:

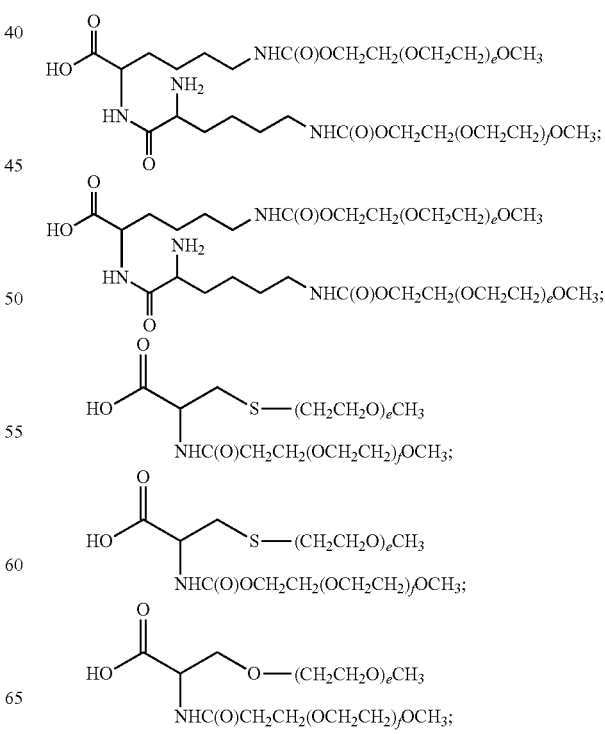

-continued

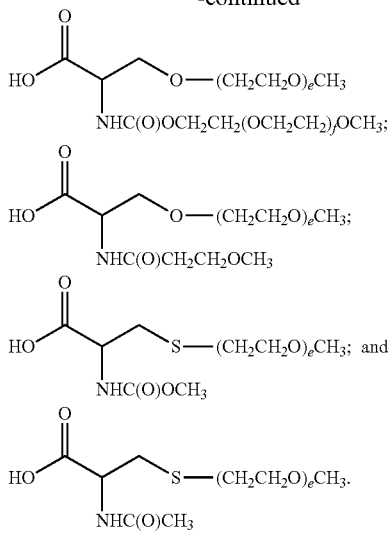

Those of skill will appreciate that the free amine in the di-lysine structures can also be pegylated through an amide or urethane bond with a PEG moiety.

In yet another embodiment, the polymeric modifying moiety is a branched PEG moiety that is based upon a tri-lysine peptide. The tri-lysine can be mono-, di-, tri-, or tetra-PEGylated. Exemplary species according to this embodiment have the formulae:

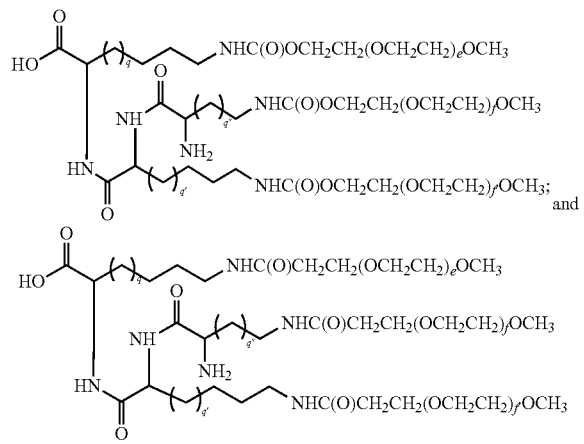

in which the indices e, f and f' are independently selected integers from 1 to 2500; and the indices q, q' and q'' are independently selected integers from 1 to 20.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

As discussed herein, the PEG of use in the conjugates of the invention can be linear or branched. An exemplary precursor of use to form the branched PEG containing peptide conjugates according to this embodiment of the invention has the formula:

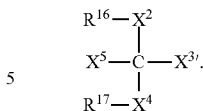

(III)

Another exemplary precursor of use to form the branched PEG containing peptide conjugates according to this embodiment of the invention has the formula:

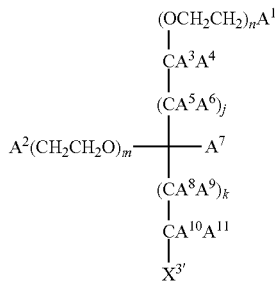

in which the indices m and n are integers independently selected from 0 to 5000. $A^1, A^2, A^3, A^4, A^5, A^6, A^7, A^8, A^9, A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^{12}A^{13}$, $-OA^{12}$ and $-SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

The branched polymer species according to this formula are essentially pure water-soluble polymers. $X^{3'}$ is a moiety that includes an ionizable (e.g., OH, COOH, $H_2PO_4$, $HSO_3$, $NH_2$, and salts thereof, etc.) or other reactive functional group, e.g., infra. C is carbon. $X^5$, $R^{16}$ and $R^{17}$ are independently selected from non-reactive groups (e.g., H, unsubstituted alkyl, unsubstituted heteroalkyl) and polymeric arms (e.g., PEG). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. When $X^{3'}$ is reacted with a reactive functional group of complementary reactivity on a linker, sugar or linker-sugar cassette, $X^{3'}$ is converted to a component of linkage fragment $X^3$.

Exemplary linkage fragments for $X^2$, $X^3$ and $X^4$ are independently selected and include a bond, S, SC(O)NH, HNC(O)S, SC(O)O, O, NH, NHC(O), (O)CNH and NHC(O)O, and OC(O)NH, $CH_2$, $CH_2S$, $CH_2O$, $CH_2CH_2O$, $CH_2OC(O)NH$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

For example, in one embodiment, $X^2$ is $CH_2$, $X^3$ is $CH_2OC(O)NH$, $X^4$ is a bond, $X^5$ is H, and $R^{16}$ and $R^{17}$ are polymeric arms (e.g., PEG).

Utilizing a branched PEG precursor described above, the branched PEG containing peptide conjugates according to this embodiment of the invention has the formula:

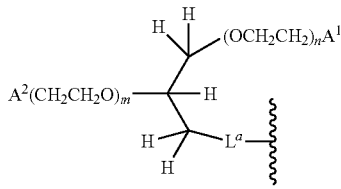

In an exemplary embodiment, $A^1$ and $A^2$ are each members selected from —OH and —OCH$_3$; m and n are each independently selected from an integer ranging from 1 to 2500; and $L^a$ comprises OC(O)NHCH$_2$C(O)NH.

Exemplary polymeric modifying groups according to this embodiment include:

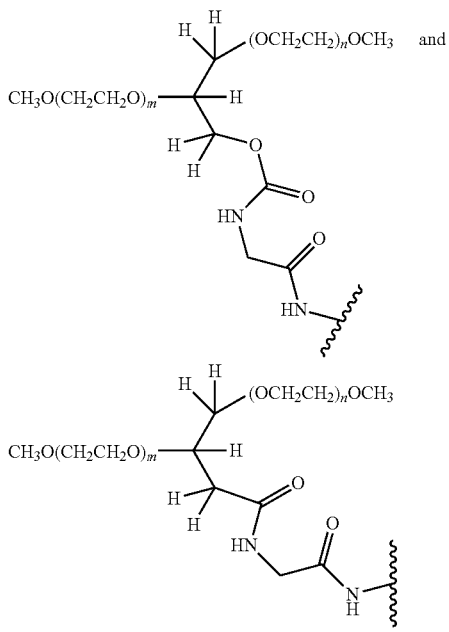

In an exemplary embodiment, the precursor (Formula III), or an activated derivative thereof, is reacted with, and thereby bound to a sugar, an activated sugar or a sugar nucleotide through a reaction between $X^{3'}$ and a group of complementary reactivity on the sugar moiety, e.g., an amine. Alternatively, $X^{3'}$ reacts with a reactive functional group on a precursor to linker, L. One or more of $R^2$, $R^3$, $R^4$, $R^5$, $R^6$ or $R^{6'}$ of Formulae I and II can include the branched polymeric modifying moiety, or this moiety bound through L.

In an exemplary embodiment, the moiety:

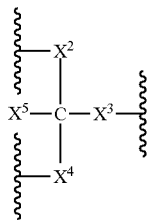

is the linker arm, L. In this embodiment, an exemplary linker is derived from a natural or unnatural amino acid, amino acid analogue or amino acid mimetic, or a small peptide formed from one or more such species. For example, certain branched polymers found in the compounds of the invention have the formula:

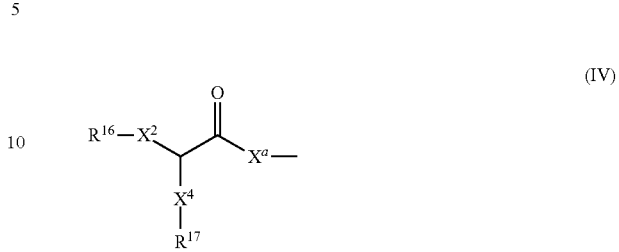

(IV)

$X^a$ is a linkage fragment that is formed by the reaction of a reactive functional group, e.g., $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an aminosaccharide (e.g., Sia, GalNH$_2$, GlcNH$_2$, ManNH$_2$, etc.), forming a $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

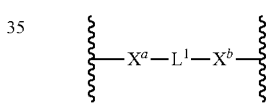

in which $X^b$ is a second linkage fragment and is independently selected from those groups set forth for $X^a$, and, similar to L, $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (e.g., Lys-Lys-Lys) in which the alpha-amine moiety(ies) and/or side chain heteroatom(s) are modified with a polymeric modifying moiety.

In a further exemplary embodiment, the peptide conjugates of the invention include a moiety, e.g., an $R^{15}$ moiety that has a formula that is selected from:

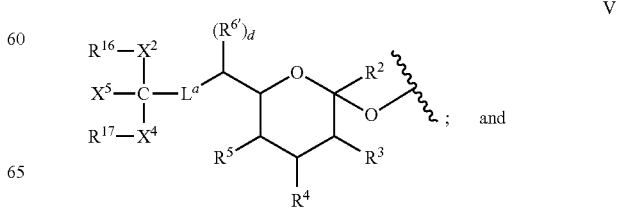

V

VI

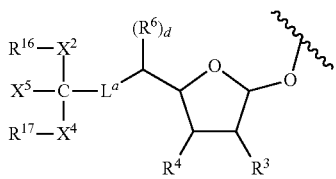

Va

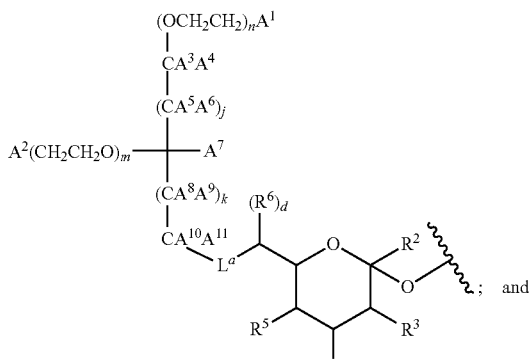

VIa

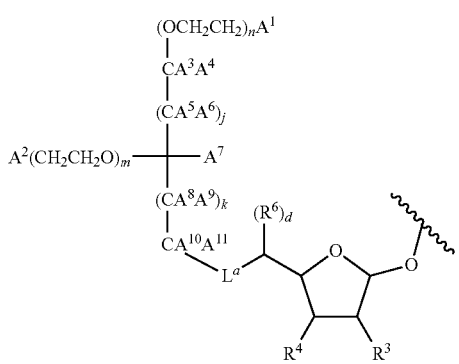

in which the identity of the radicals represented by the various symbols is the same as that discussed hereinabove. $L^a$ is a bond or a linker as discussed above for L and $L^1$, e.g., substituted or unsubstituted alkyl or substituted or unsubstituted heteroalkyl moiety. In an exemplary embodiment, $L^a$ is a moiety of the side chain of sialic acid that is functionalized with the polymeric modifying moiety as shown. Exemplary $L^a$ moieties include substituted or unsubstituted alkyl chains that include one or more OH or $NH_2$.

In yet another exemplary embodiment, the invention provides peptide conjugates having a moiety, e.g., an $R^{15}$ moiety with formula:

VII

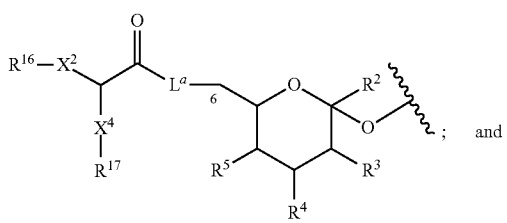

VIII

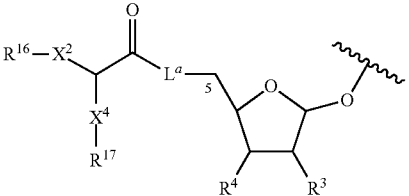

The identity of the radicals represented by the various symbols is the same as that discussed hereinabove. As those of skill will appreciate, the linker arm in Formulae VII and VIII is equally applicable to other modified sugars set forth herein. In exemplary embodiment, the species of Formulae VII and VIII are the $R^{15}$ moieties attached to the glycan structures set forth herein.

In yet another exemplary embodiment, the Factor IX peptide conjugate includes a $R^{15}$ moiety with a formula which is a member selected from:

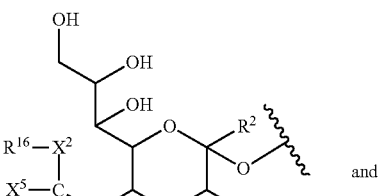

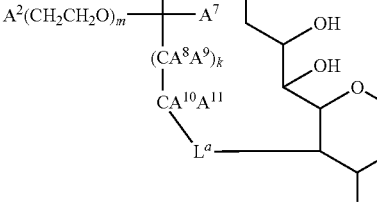

in which the identities of the radicals are as discussed above. An exemplary species for $L^a$ is $-(CH_2)_jC(O)NH(CH_2)_hC(O)NH-$, in which the indices h and j are independently selected integers from 0 to 10. A further exemplary species is $-C(O)NH-$. The indices m and n are integers independently selected from 0 to 5000. $A^1, A^2, A^3, A^4, A^5, A^6, A^7, A^8, A^9, A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^{12}A^{13}, -OA^{12}$ and $-SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the glycosyl linking group has a structure according to the following formula:

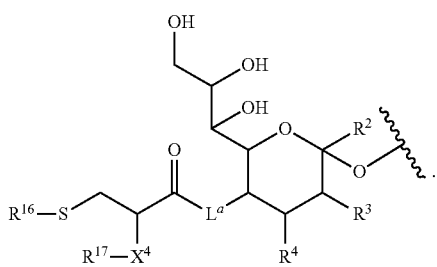

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g., 1 kDa, 2 kDa, 5 kDa, 10 kDa, 15 kDa, 20 kDa, 25 kDa, 30 kDa, 35 kDa, 40 kDa and 45 kDa is of use in the present invention.

In an exemplary embodiment, the $R^{15}$ moiety has a formula that is a member selected from the group:

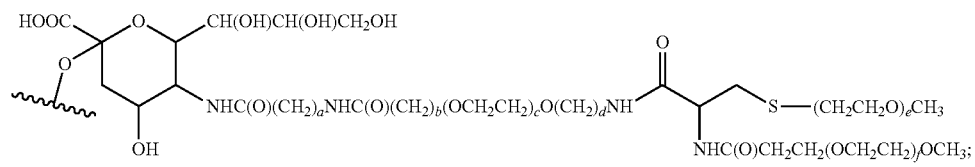

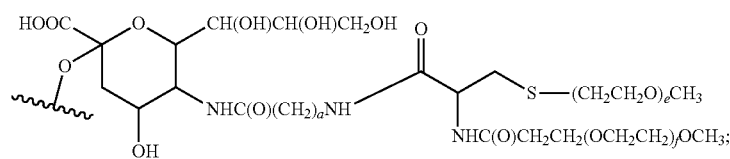

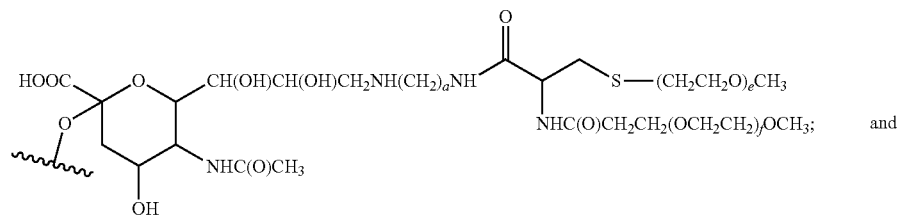

and

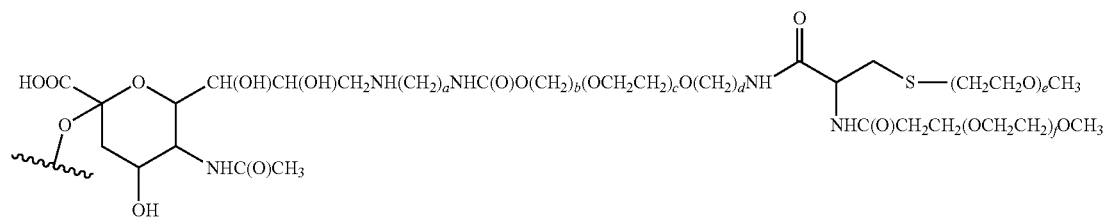

In each of the structures above, the linker fragment —NH(CH$_2$)$_a$- can be present or absent.

In other exemplary embodiments, the peptide conjugate includes an R$^{15}$ moiety selected from the group:

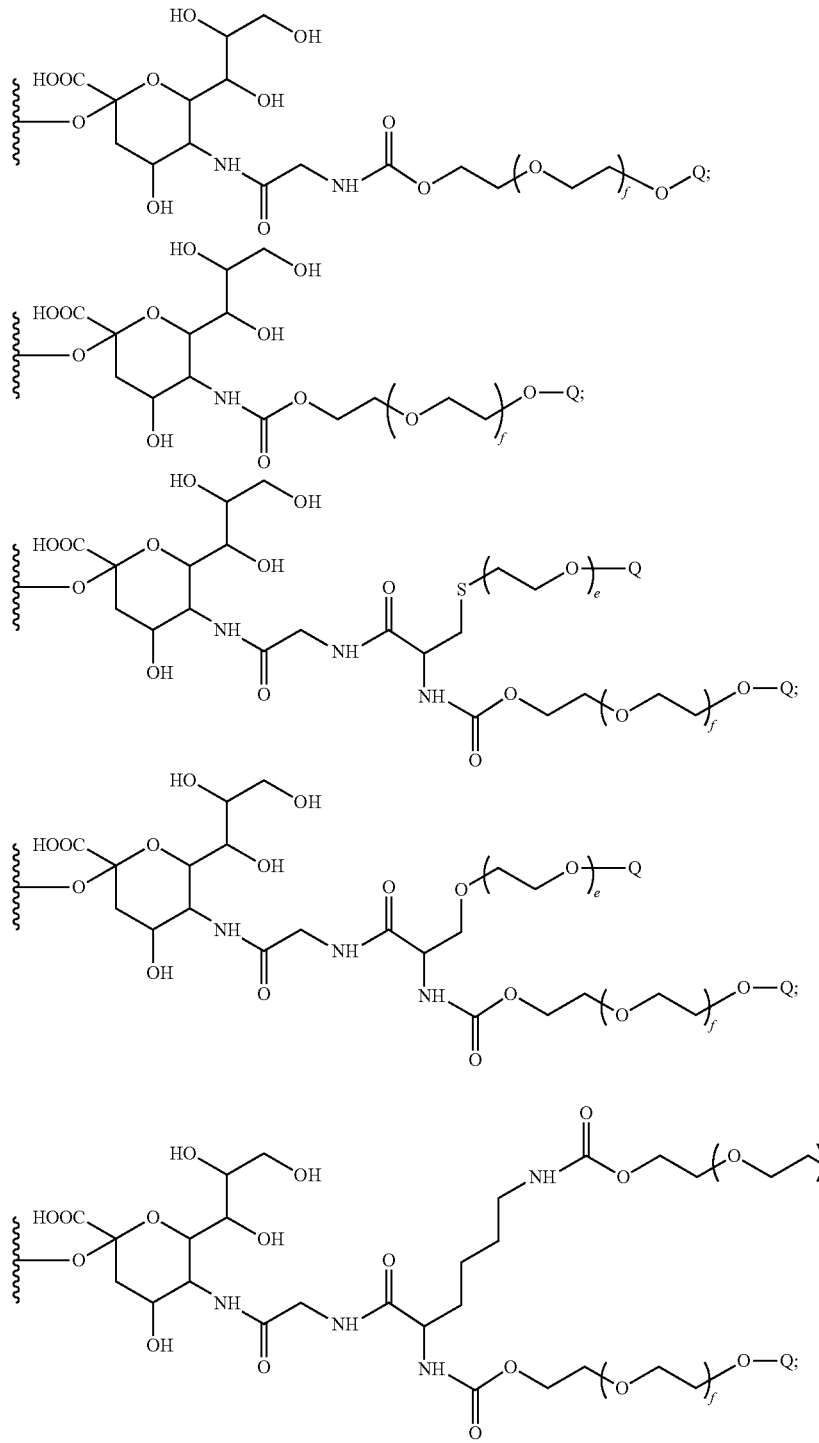

In each of the formulae above, the indices e and f are independently selected from the integers from 1 to 2500. In further exemplary embodiments, e and f are selected to provide a PEG moiety that is about 1 kDa, 2 kDa, 5 kDa, 10 kDa, 15 kDa, 20 kDa, 25 kDa, 30 kDa, 35 kDa, 40 kDa and 45 kDa.

The symbol Q represents substituted or unsubstituted alkyl (e.g., C$_1$-C$_6$ alkyl, e.g., methyl), substituted or unsubstituted heteroalkyl or H.

Other branched polymers have structures based on di-lysine (Lys-Lys) peptides, e.g.:

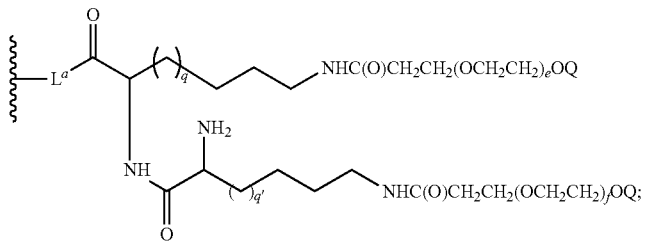
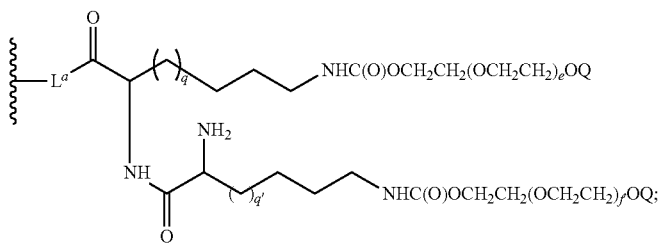
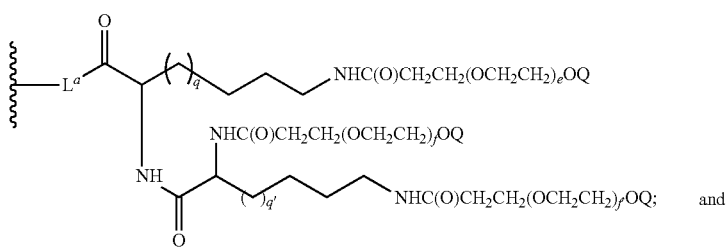
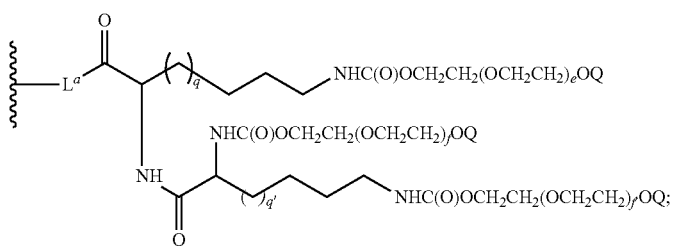
and tri-lysine peptides (Lys-Lys-Lys), e.g.:
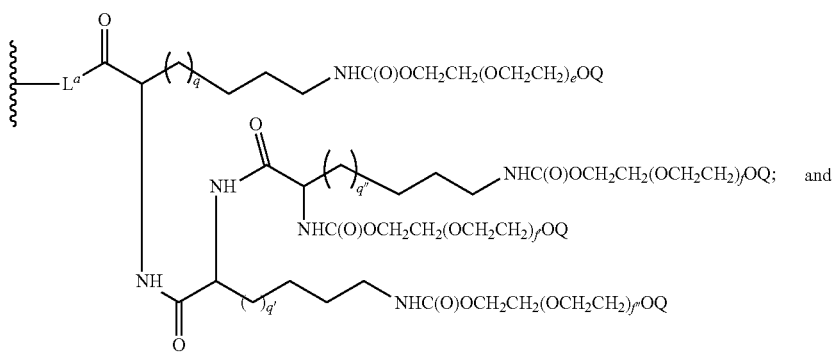

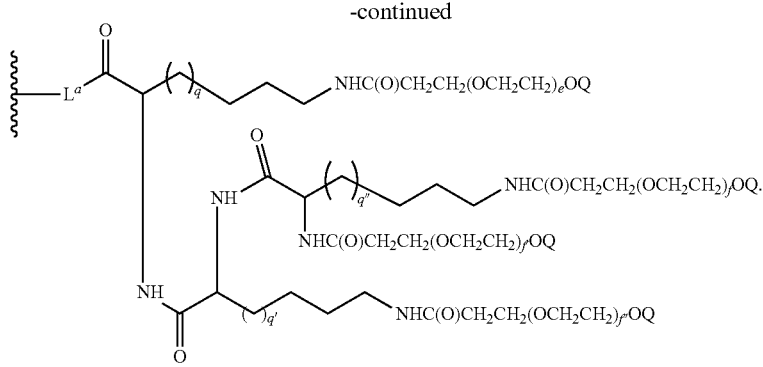

In each of the figures above, the indices e, f, f' and f" represent integers independently selected from 1 to 2500. The indices q, q' and q" represent integers independently selected from 1 to 20.

In another exemplary embodiment, the modifying group:

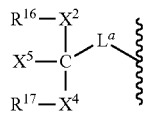

has a formula that is a member selected from:

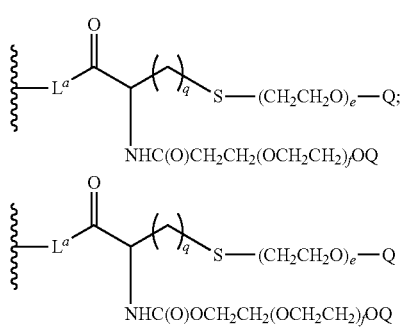

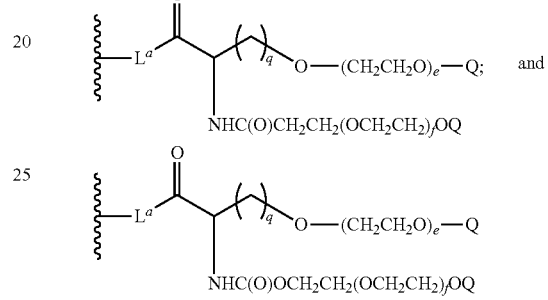

wherein Q is a member selected from H and substituted or unsubstituted $C_1$-$C_6$ alkyl. The indices e and f are integers independently selected from 1 to 2500, and the index q is an integer selected from 0 to 20.

In another exemplary embodiment, the modifying group:

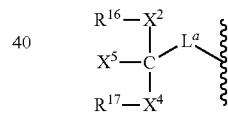

has a formula that is a member selected from:

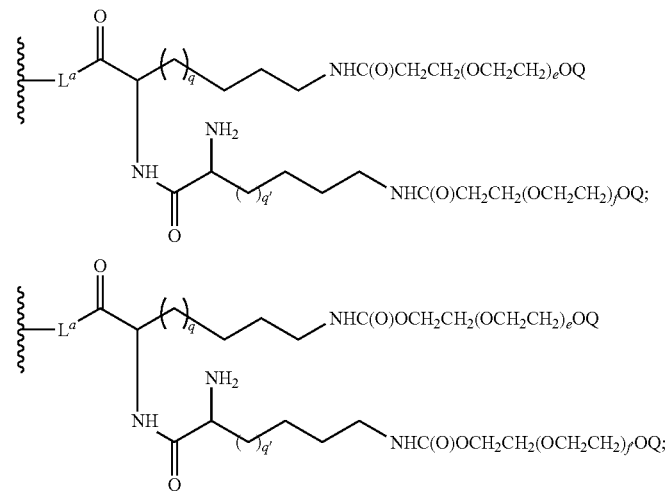

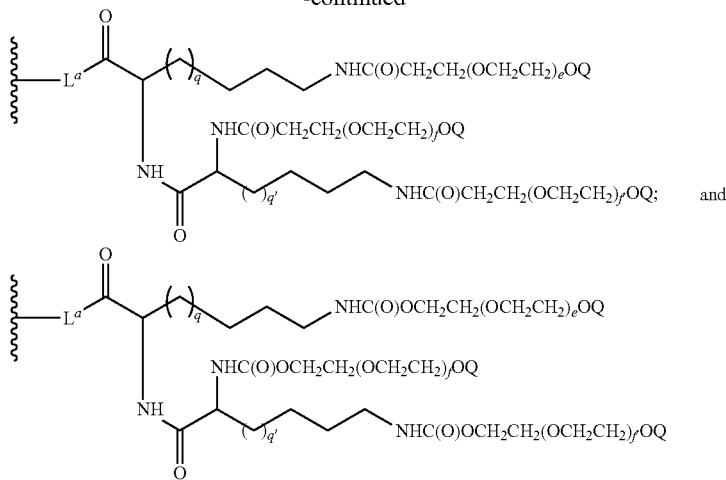

wherein Q is a member selected from H and substituted or unsubstituted $C_1$-$C_6$ alkyl. The indices e, f and f' are integers independently selected from 1 to 2500, and q and q' are integers independently selected from 1 to 20.

In another exemplary embodiment, the branched polymer has a structure according to the following formula:

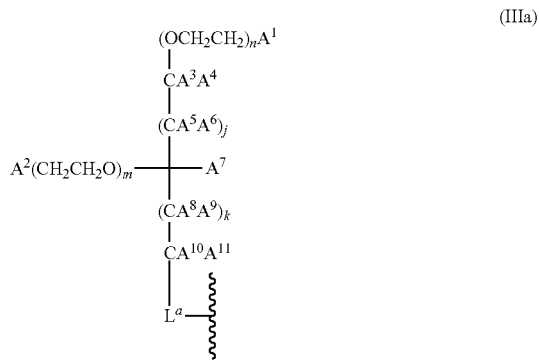

in which the indices m and n are integers independently selected from 0 to 5000. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^{12}A^{13}$, $-OA^{12}$ and $-SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Formula IIIa is a subset of Formula III. The structures described by Formula IIIa are also encompassed by Formula III.

In another exemplary embodiment according to the formula above, the branched polymer has a structure according to the following formula:

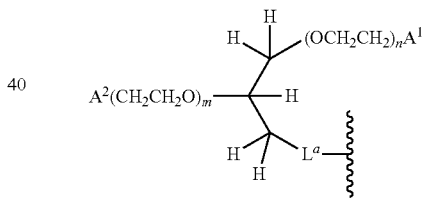

In an exemplary embodiment, $A^1$ and $A^2$ are each $-OCH_3$ or H.

In an illustrative embodiment, the modified sugar is sialic acid and selected modified sugar compounds of use in the invention have the formulae:

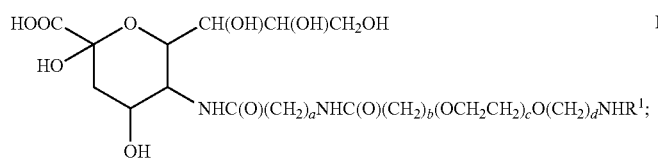 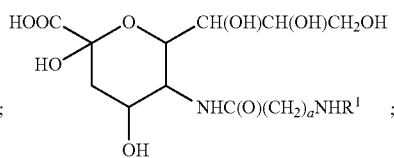

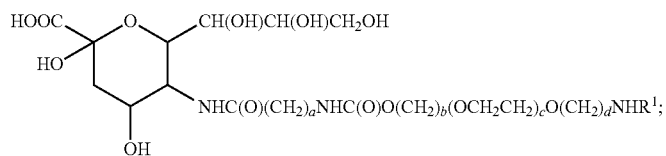 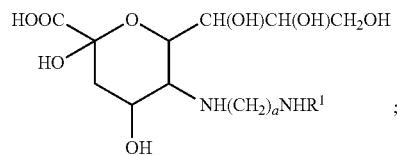

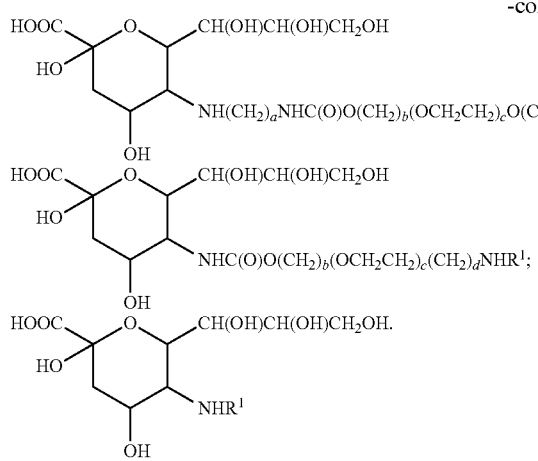
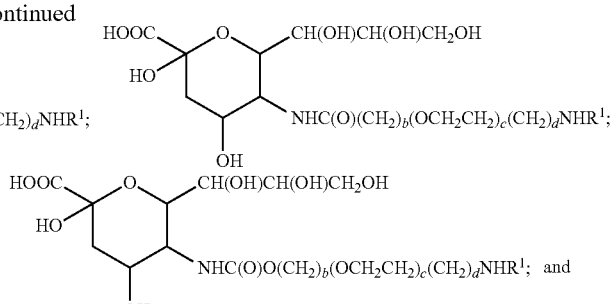

The indices a, b and d are integers from 0 to 20. The index c is an integer from 1 to 2500. The structures set forth above can be components of $R^{15}$.

In another illustrative embodiment, a primary hydroxyl moiety of the sugar is functionalized with the modifying group. For example, the 9-hydroxyl of sialic acid can be converted to the corresponding amine and functionalized to provide a compound according to the invention. Formulae according to this embodiment include:

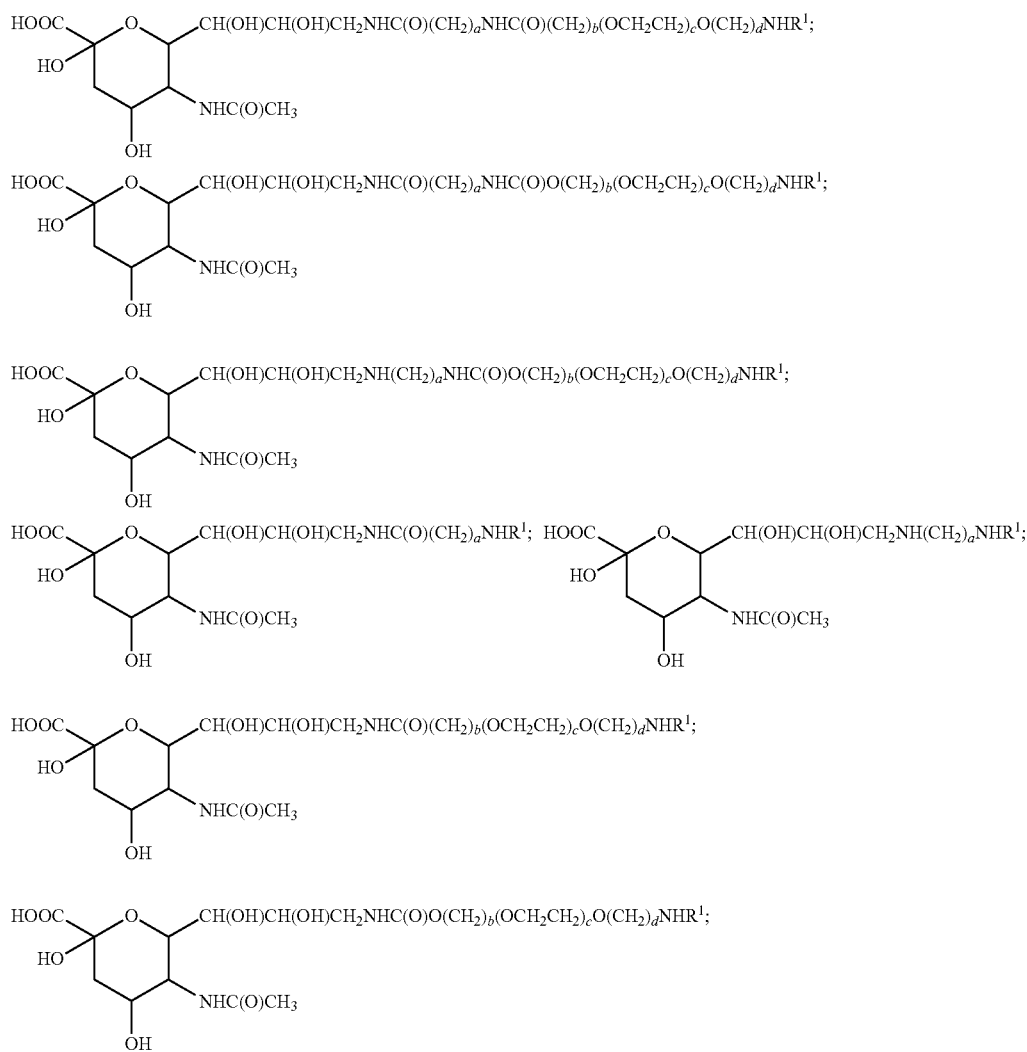

-continued

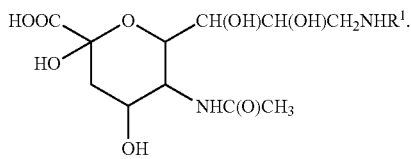

The structures set forth above can be components of $R^{15}$.

Although the present invention is exemplified in the preceding sections by reference to PEG, as those of skill will appreciate, an array of polymeric modifying moieties is of use in the compounds and methods set forth herein.

In selected embodiments, $R^1$ or $L\text{-}R^1$ is a branched PEG, for example, one of the species set forth above. In an exemplary embodiment, the branched PEG structure is based on a cysteine peptide. Illustrative modified sugars according to this embodiment include:

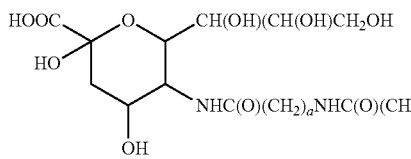

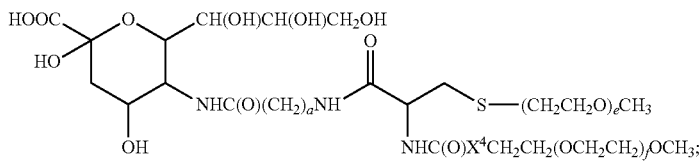

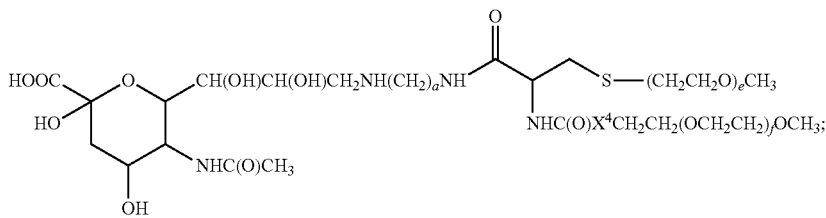

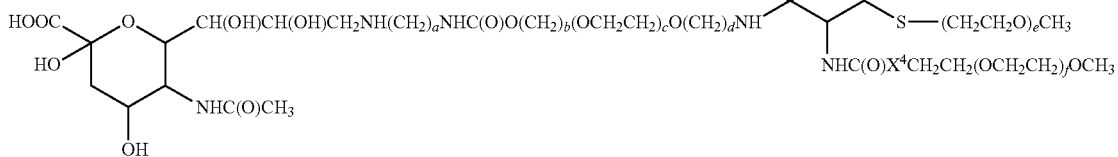

in which $X^4$ is a bond or O. In each of the structures above, the alkylamine linker —$(CH_2)_a NH$— can be present or absent. The structures set forth above can be components of $R^{15}/R^{15'}$.

As discussed herein, the polymer-modified sialic acids of use in the invention may also be linear structures. Thus, the invention provides for conjugates that include a sialic acid moiety derived from a structure such as:

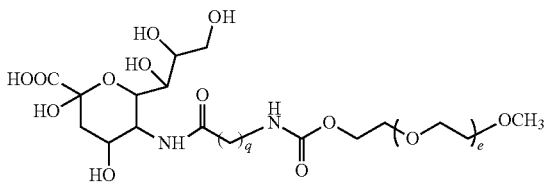

in which the indices q and e are as discussed above.

Exemplary modified sugars are modified with water-soluble or water-insoluble polymers. Examples of useful polymer are further exemplified below.

In another exemplary embodiment, the peptide is derived from insect cells, remodeled by adding GlcNAc and Gal to the mannose core and glycopegylated using a sialic acid bearing a linear PEG moiety, affording a Factor IX peptide that comprises at least one moiety having the formula:

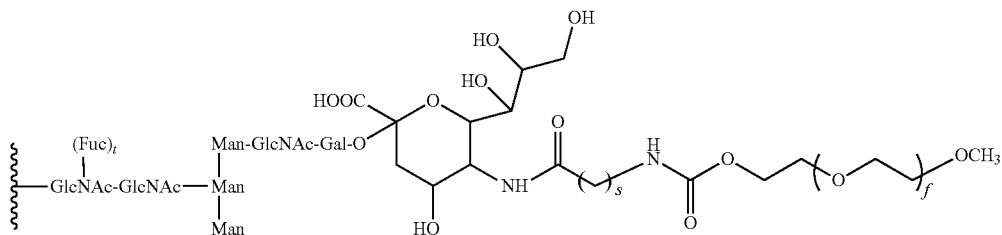

in which the index t is an integer from 0 to 1; the index s represents an integer from 1 to 10; and the index f represents an integer from 1 to 2500.

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

The motifs forth above for $R^1$, $L-R^1$, $R^{15}$, $R^{15'}$ and other radicals are equally applicable to water-insoluble polymers, which may be incorporated into the linear and branched structures without limitation utilizing chemistry readily accessible to those of skill in the art. Similarly, the incorporation of these species into any of the modified sugars discussed herein is within the scope of the present invention. Accordingly, the invention provides conjugates containing, and for the use of to prepare such conjugates, sialic acid and other sugar moieties modified with a linear or branched water-insoluble polymers, and activated analogues of the modified sialic acid species (e.g., CMP-Sia-(water insoluble polymer)).

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid' polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J. Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly(amino acids), poly(anhydrides), poly(orthoesters), poly (carbonates), poly(phosphazines), poly(phosphoesters), poly (thioesters), polysaccharides and mixtures thereof. More preferably still, the biosresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a difunctional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene)oxide. Such poly(alkylene) oxides can include, for example, poly(ethylene)oxide, poly (propylene)oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly(α-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyaluronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, is of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

Biomolecules

In another preferred embodiment, the modified sugar bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated peptide is elaborated by the attachment of an avidin or streptavidin moiety bearing one or more modifying groups.

Methods

In addition to the conjugates discussed above, the present invention provides methods for preparing these and other conjugates. Thus, in a further aspect, the invention provides a method of forming a covalent conjugate between a selected moiety and a peptide. Additionally, the invention provides methods for targeting conjugates of the invention to a particular tissue or region of the body. Furthermore, the present invention provides a method for preventing, curing, or ameliorating a disease state by administering a conjugate of the invention to a subject at risk of developing the disease or a subject that has the disease.

In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via an intact glycosyl linking group, which is interposed between, and covalently linked to both the peptide and the modifying group (e.g., water-soluble polymer).

In an exemplary embodiment, the conjugate is formed through a chemical process sometimes referred to as chemoPEGylation. Further discussion of the synthesis chemoPEGylated peptide conjugates is provided in PCT/US02/3226, filed Oct. 9, 2002 and U.S. patent application Ser. No. 10/287,994, filed Nov. 5, 2002, each of which are herein incorporated by reference in their entirety.

The method includes contacting the peptide with a mixture containing a modified sugar and a glycosyltransferase for which the modified sugar is a substrate. The reaction is conducted under conditions sufficient to form a covalent bond between the modified sugar and the peptide. The sugar moiety of the modified sugar is preferably selected from nucleotide sugars, activated sugars, and sugars that are neither nucleotides nor activated.

The acceptor peptide (glycosylated or non-glycosylated) is typically synthesized de novo, or recombinantly expressed in a prokaryotic cell (e.g., bacterial cell, such as *E. coli*) or in a eukaryotic cell such as a mammalian cell (e.g., CHO cells), yeast (e.g., *Saccharomyces*), insect, or plant cell. The peptide can be either a full-length protein or a fragment. Moreover, the peptide can be a wild type or mutated peptide. In an exemplary embodiment, the peptide includes a mutation that adds one or more consensus glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-aceylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used.

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation and O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In one embodiment, the invention provides a method for linking Factor IX and one or more peptide through a linking group. The linking group is of any useful structure and may be selected from straight-chain and branched chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosylunits, respectively. In practice, the $(glycosyl)^1$-PEG-$(glycosyl)^2$ linker is contacted with the first peptide and a first transferase for which the first glycosyl unit is a substrate, thereby forming $(peptide)^1$-$(glycosyl)^1$-PEG-$(glycosyl)^2$. Glycosyltransferase and/or unreacted peptide is then optionally removed from the reaction mixture. The second peptide and a second transferase for which the second glycosyl unit is a substrate are added to the $(peptide)^1$-$(glycosyl)^1$-PEG-$(glycosyl)^2$ conjugate, forming $(peptide)^1$-$(glycosyl)^1$-PEG-$(glycosyl)^2$-$(peptide)^2$. Those of skill in the art will appreciate that the method outlined above is also applicable to forming conjugates between more than two peptides by, for example, the use of a branched PEG, dendrimer, poly (amino acid), polysaccharide or the like.

Another exemplary embodiment is set forth in Scheme 1. Scheme 1 shows a method of preparing a conjugate comprising a polymer. The polymer increases the circulatory half-life of the Factor IX protein.

Scheme 1

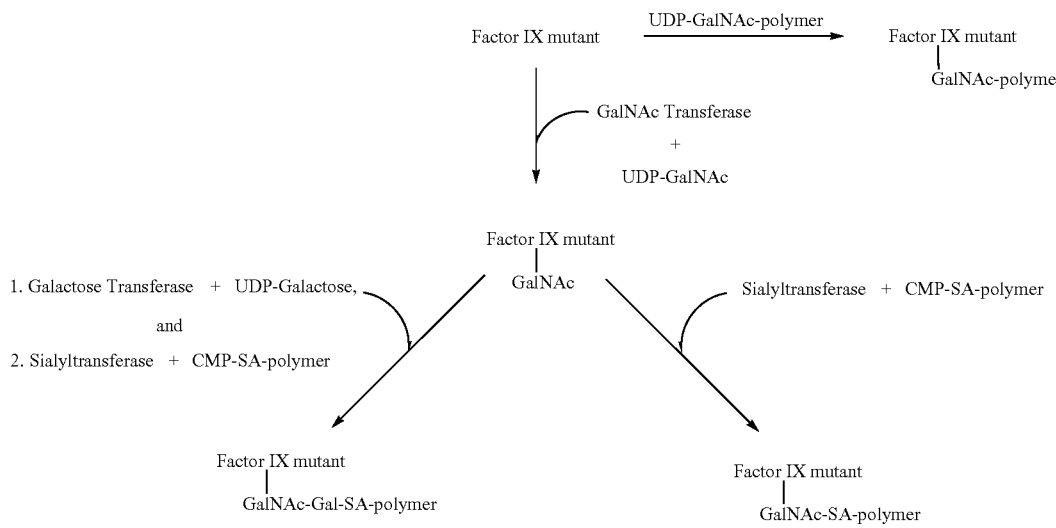

in which SA is sialic acid, and polymer is PEG, mPEG, poly sialic acid, a water soluble or water insoluble polymer. Though the method is exemplified by reference to a Factor IX mutant, those of skill will appreciate it is equally applicable to wild-type Factor IX peptides.

The use of reactive derivatives of PEG (or other linkers) to attach one or more peptide moieties to the linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990))); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

Preparation of Modified Sugars

In general, the sugar moiety and the modifying group are linked together through the use of reactive groups, which are typically transformed by the linking process into a new organic functional group or species that is unreactive under physiologically relevant conditions. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:
 (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
 (b) hydroxyl groups, which can be converted to, e.g., esters, ethers, aldehydes, etc.
 (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;
 (d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., Curr. Med. Chem. 6: 93 (1999); and Schafer et al., J. Org. Chem. 65: 24 (2000)).

In an exemplary embodiment, the peptide that is modified by a method of the invention is a glycopeptide that is produced in prokaryotic cells (e.g., E. coli), eukaryotic cells including yeast and mammalian cells (e.g., CHO cells), or in a transgenic animal and thus, contains N- and/or O-linked oligosaccharide chains, which are incompletely sialylated. The oligosaccharide chains of the glycopeptide lacking a sialic acid and containing a terminal galactose residue can be PEG-ylated, PPG-ylated or otherwise modified with a modified sialic acid.

Exemplary PEG-sialic acid derivatives include:

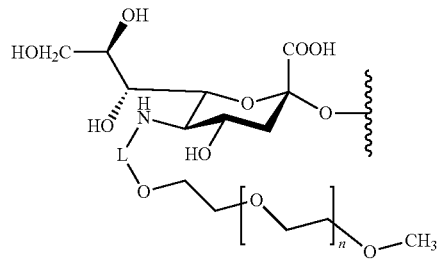

in which L is a substituted or unsubstituted alkyl or substituted or unsubstituted heteroalkyl linker moiety joining the sialic acid moiety and the PEG moiety, and "n" is 1 or greater; and

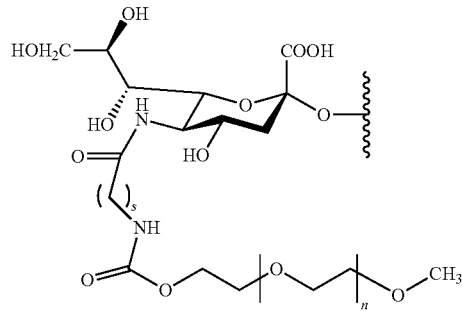

in which the index "s" represents an integer from 0 to 20, and "n" is 1 or greater.

In Scheme 2, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

Scheme 2

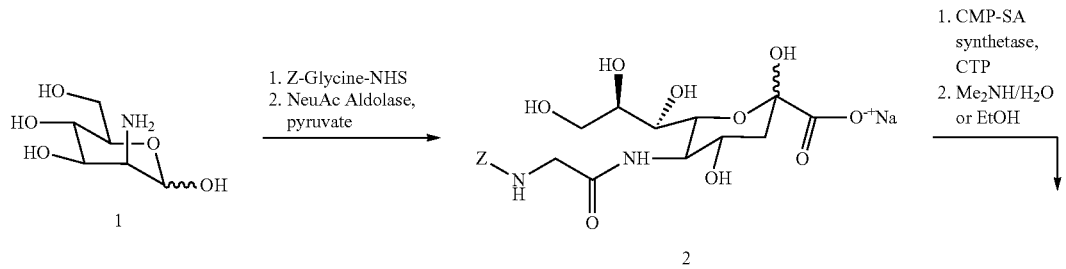

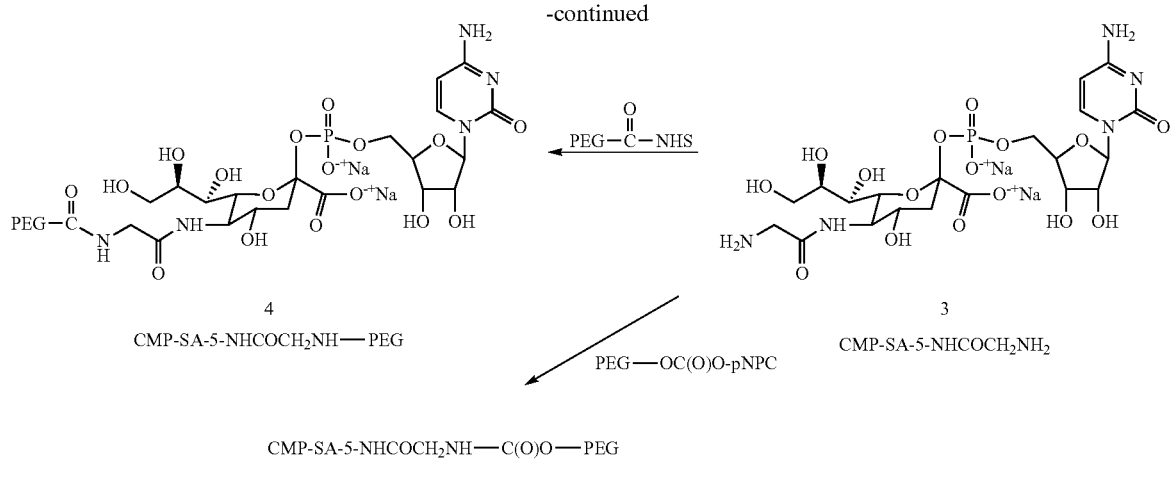

Table 1 sets forth representative examples of sugar monophosphates that are derivatized with a modifying group, such as a PEG or PPG moiety. Factor IX peptides can be modified by the method of Scheme 2. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 1

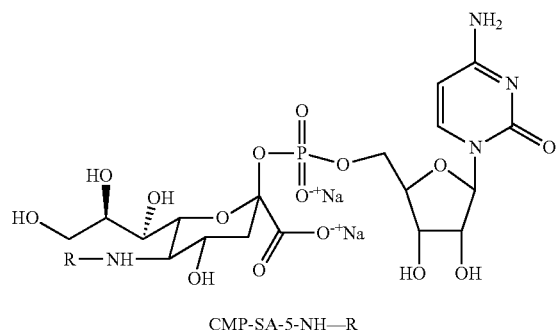

CMP-SA-5-NH—R

TABLE 1-continued

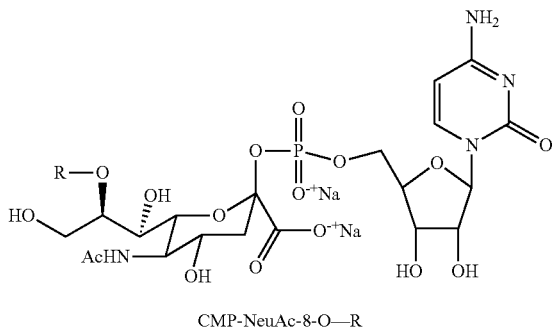

CMP-NeuAc-8-O—R

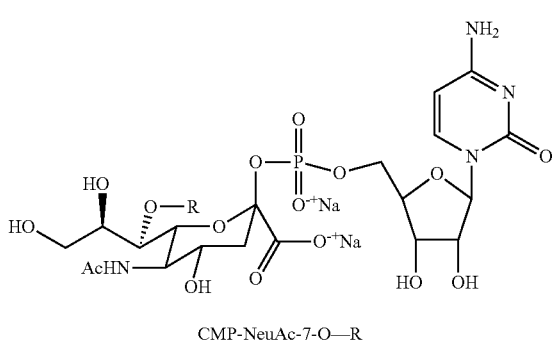

CMP-NeuAc-7-O—R

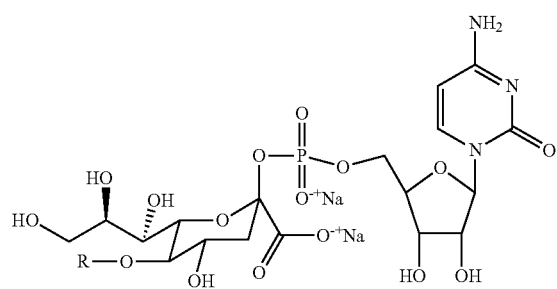

CMP-KDN-5-O—R

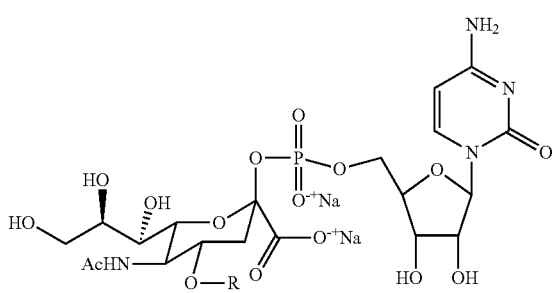

CMP-NeuAc-4-O—R

TABLE 1-continued

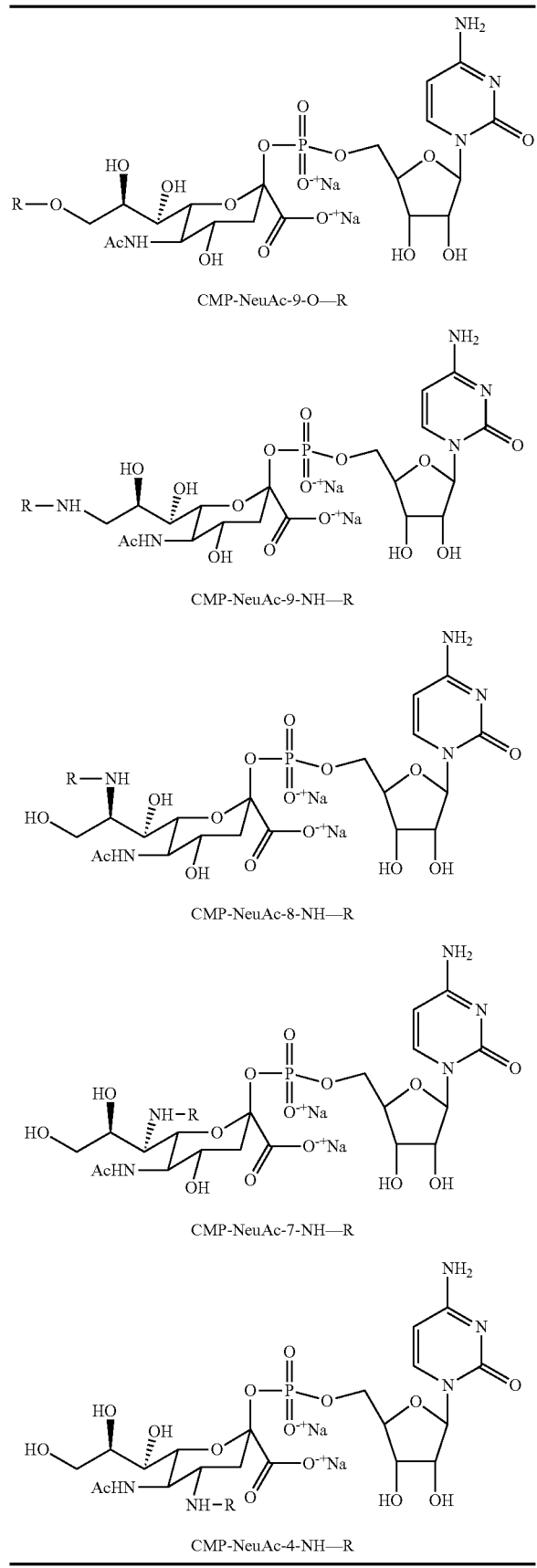

CMP-NeuAc-9-O—R

CMP-NeuAc-9-NH—R

CMP-NeuAc-8-NH—R

CMP-NeuAc-7-NH—R

CMP-NeuAc-4-NH—R wherein R represents a modifying group, e.g., linear or branched PEG or -$L^x$-$R^x$ in which $L^x$ is a linker selected from a bond (zero-order), substituted or unsubstituted alkyl and substituted or unsubstituted heteroalkyl, and $R^x$ is the modifying group.

The modified sugar phosphates of use in practicing the present invention can be substituted in other positions as well as those set forth above. Presently preferred substitutions of sialic acid are set forth in the following formula:

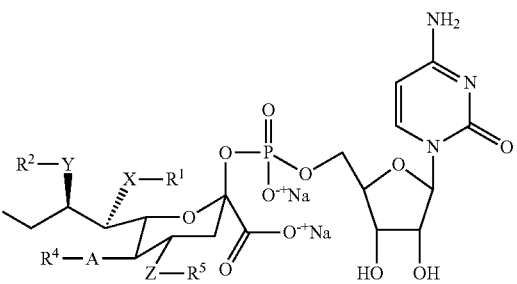

in which X is a linking group, which is preferably selected from —O—, —N(H)—, —S, $CH_2$—, and —N(R)$_2$, in which each R is a member independently selected from $R^1$-$R^5$. The symbols Y, Z, A and B each represent a group that is selected from the group set forth above for the identity of X. X, Y, Z, A and B are each independently selected and, therefore, they can be the same or different. The symbols $R^1$, $R^2$, $R^3$, $R^4$ and $R^5$ represent H, a water-soluble polymer, therapeutic moiety, biomolecule or other moiety. Alternatively, these symbols represent a linker that is bound to a water-soluble polymer, therapeutic moiety, biomolecule or other moiety.

Exemplary moieties attached to the conjugates disclosed herein include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, SLe$_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

Cross-Linking Groups

Preparation of the modified sugar for use in the methods of the present invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al.,

*Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

In still another embodiment, the invention utilizes photoactivatable groups, for example, thost that are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352, 670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated peptide. The exemplary modified sialic acid is labeled with m-PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than m-PEG including other water-soluble polymers, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, GalNAc, Galβ1,3GalNAc, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment, an O-linked carbohydrate residue is "trimmed" prior to the addition of the modified sugar. For example a GalNAc-Gal residue is trimmed back to GalNAc. A modified sugar bearing a water-soluble polymer is conjugated to one or more of the sugar residues exposed by the "trimming" In one example, a glycopeptide is "trimmed" and a water-soluble polymer is added to the resulting O-side chain amino acid or glycopeptide glycan via a saccharyl moiety, e.g., Sia, Gal, or GalNAc moiety conjugated to the water-soluble polymer. The modified saccharyl moiety is attached to an acceptor site on the "trimmed" glycopeptide. Alternatively, an unmodified saccharyl moiety, e.g., Gal can be added the terminus of the O-linked glycan.

In another exemplary embodiment, a water-soluble polymer is added to a GalNAc residue via a modified sugar having a galactose residue. Alternatively, an unmodified Gal can be added to the terminal GalNAc residue.

In yet a further example, a water-soluble polymer is added onto a Gal residue using a modified sialic acid.

In another exemplary embodiment, an O-linked glycosyl residue is "trimmed back" to the GalNAc attached to the amino acid. In one example, a water-soluble polymer is added via a Gal modified with the polymer. Alternatively, an unmodified Gal is added to the GalNAc, followed by a Gal with an attached water-soluble polymer. In yet another embodiment, one or more unmodified Gal residue is added to the GalNAc, followed by a sialic acid moiety modified with a water-soluble polymer.

Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, the water-soluble polymer is added to a terminal Gal residue using a polymer modified sialic acid. An appropriate sialyltransferase is used to add a modified sialic acid. The approach is summarized in Scheme 3.

Scheme 3

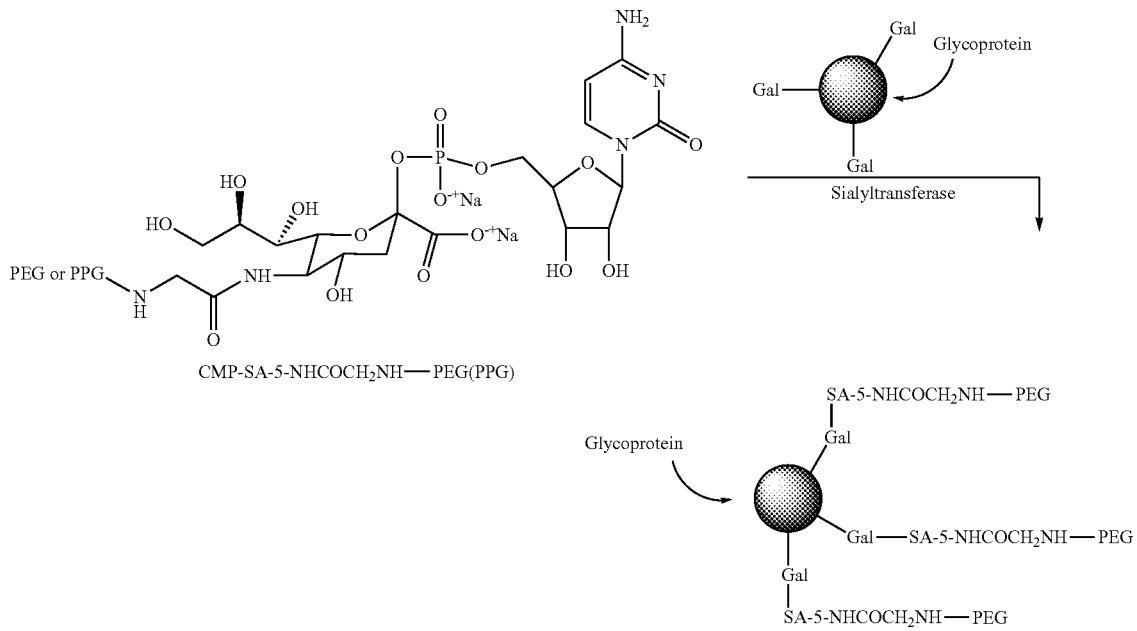

In yet a further approach, summarized in Scheme 4, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

Any modified sugar can be used with its appropriate glycosyltransferase, depending on the terminal sugars of the oligosaccharide side chains of the glycopeptide (Table 2). As discussed above, the terminal sugar of the glycopeptide required for introduction of the PEG-ylated or PPG-ylated structure can be introduced naturally during expression or it can be produced post expression using the appropriate glycosidase(s), glycosyltransferase(s) or mix of glycosidase(s) and glycosyltransferase(s).

Scheme 4

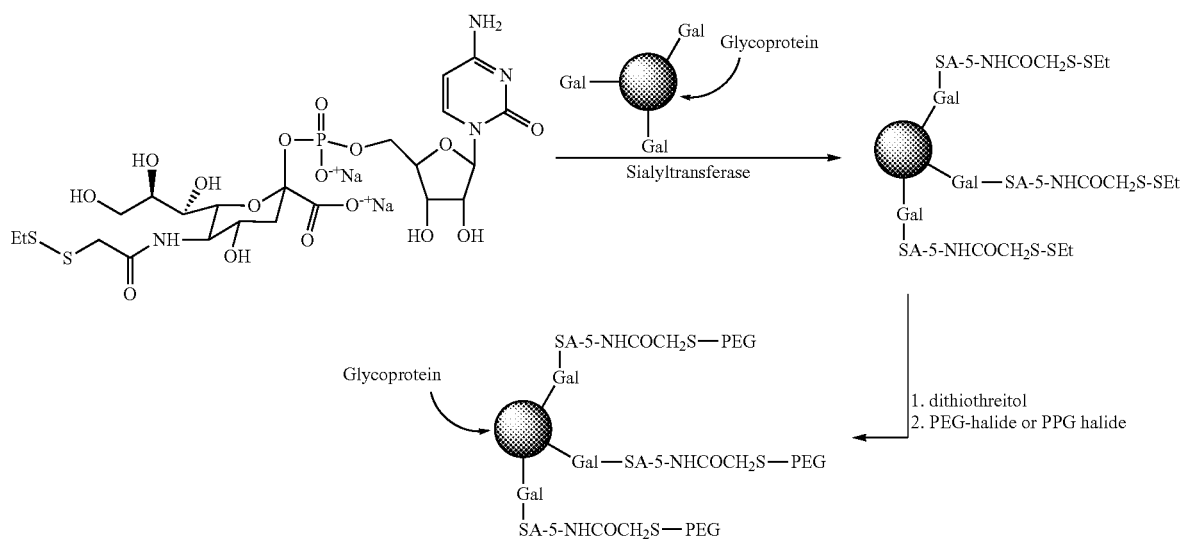

TABLE 2

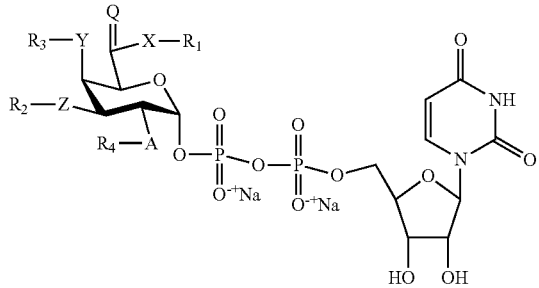

UDP-galactose-derivatives

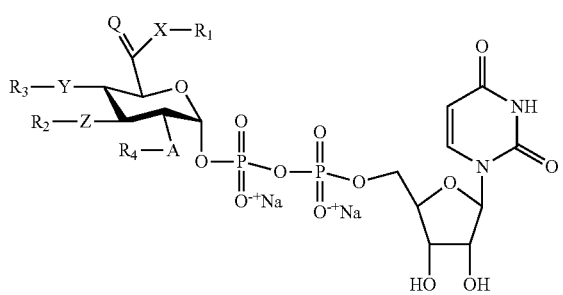

UDP-Glucose-derivatives

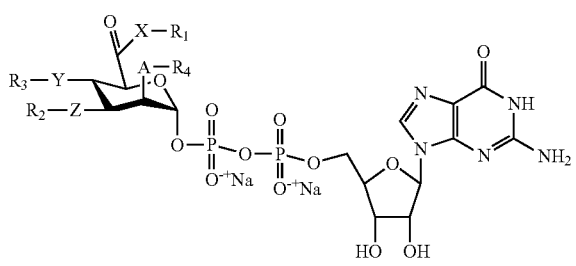

GDP-Mannose-derivatives

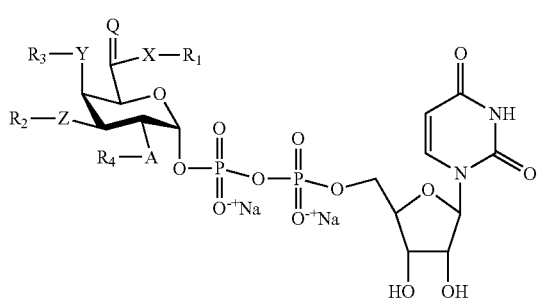

UDP-galactosamine-derivatives
(when A = NH, R$_4$ may be acetyl)

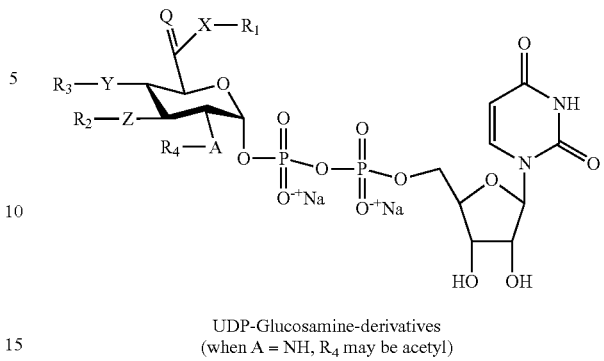

UDP-Glucosamine-derivatives
(when A = NH, R$_4$ may be acetyl)

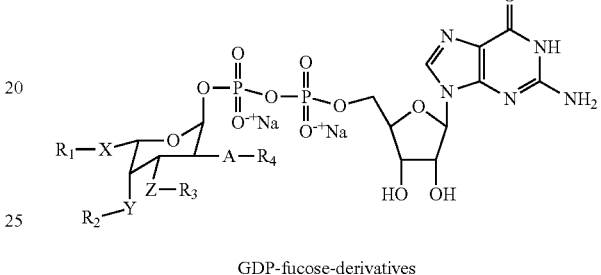

GDP-fucose-derivatives

X = O, NH, S, CH$_2$, N—(R$_{1-5}$)$_2$.
Y = X;
Z = X;
A = X;
B = X.
Q = H$_2$, O, S, NH, N—R.
R, R$_{1-4}$ = H. Linker-M, M.
M = Ligand of interest
Ligand of interest = acyl-PEG, acyl-PPG, alkyl-PEG, acyl-alkyl-PEG, acyl-alkyl-PEG, carbamoyl-PEG, carbamoyl-PPG, PEG, PPG, acyl-aryl-PEG, acyl-aryl-PPG, aryl-PEG, aryl-PPG, Mannose-6-phosphate, heparin, heparan, SLex, Mannose, FGF, VFGF, protein, chondroitin, keratan, dermatan, albumin, integrins, peptides, etc.

In a further exemplary embodiment, UDP-galactose-PEG is reacted with bovine milk β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcN to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG- or PPG-galactose functionality onto the exposed GlcNAc.

In an alternative embodiment, the modified sugar is added directly to the peptide backbone using a glycosyltransferase known to transfer sugar residues to the peptide backbone. This exemplary embodiment is set forth in Scheme 5. Exemplary glycosyltransferases useful in practicing the present invention include, but are not limited to, GalNAc transferases (GalNAc T1-20), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

molecular weight cutoff of about 3000 to about 10,000 can be used to remove proteins such as glycosyl transferases.

If the peptide is produced intracellularly, as a first step, the particulate debris, either host cells or lysed fragments, is removed. Following glycoPEGylation, the PEGylated peptide is purified by art-recognized methods, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices

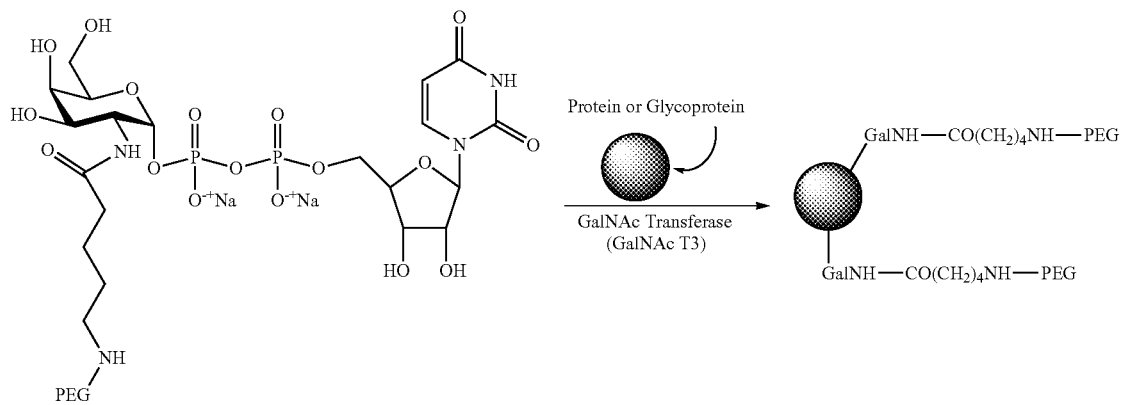

Scheme 5

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

Purification of Factor IX Conjugates

The products produced by the above processes can be used without purification. However, it is usually preferred to recover the product and one or more of the intermediates, e.g., nucleotide sugars, branched and linear PEG species, modified sugars and modified nucleotide sugars. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps. Additionally, the modified glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics or preservatives may be included to prevent the growth of adventitious contaminants. In an exemplary embodiment, the protease inhibitor is antipain.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Other methods of use in purification include size exclusion chromatography (SEC), hydroxyapatite chromatography, hydrophobic interaction chromatography and chromatography on Blue Sepharose.

One or more RP-HPLC steps employing hydrophobic RP-HPLC media, e.g., silica gel having pendant methyl or other aliphatic groups, may be employed to further purify a polypeptide conjugate composition. Some or all of the foregoing purification steps, in various combinations, can also be employed to provide a homogeneous or essentially homogeneous modified glycoprotein.

The modified glycopeptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

Pharmaceutical Compositions

Descriptions of the pharamceutical compositions of use in the invention are further described in U.S. Provisional Patent Application No. 60/684,729, filed May 25, 2005, and U.S. Provisional Patent Application No. 60/527,089, filed Sep. 13, 2004, both of which are herein incorporated by reference.

The following examples are provided to illustrate the conjugates, and methods and of the present invention, but not to limit the claimed invention.

EXAMPLES

Example 1

Preparation of Cysteine-PEG$_2$ (2)

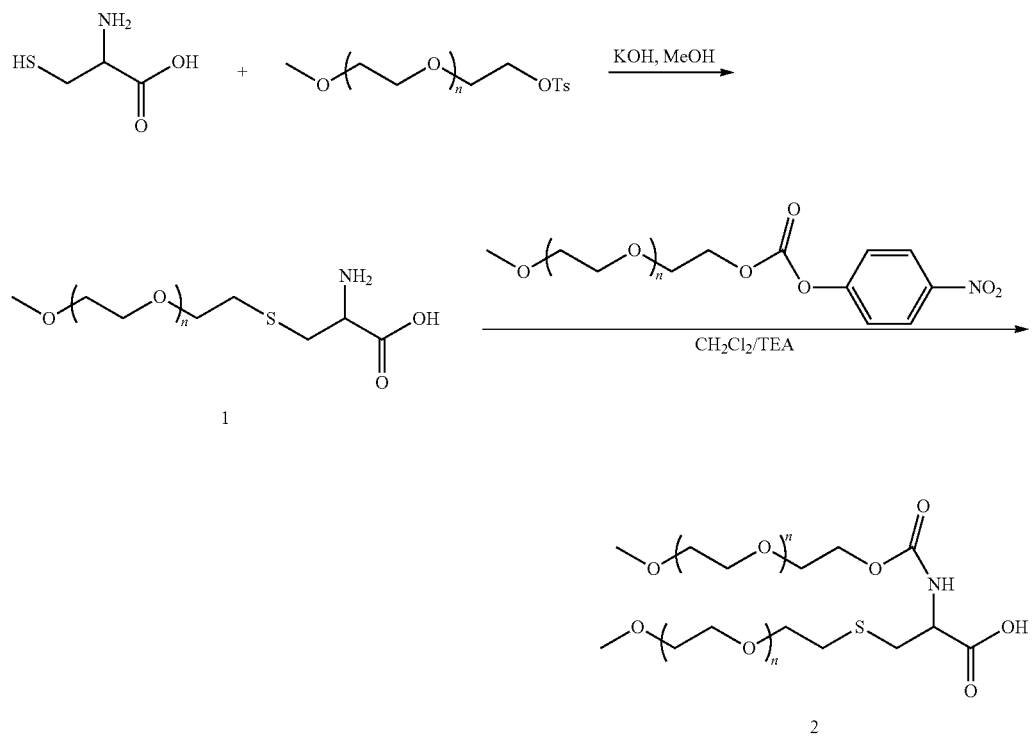

1.1 Synthesis of (1)

Potassium hydroxide (84.2 mg, 1.5 mmol, as a powder) was added to a solution of L-cysteine (93.7 mg, 0.75 mmol) in anhydrous methanol (20 mL) under argon. The mixture was stirred at room temperature for 30 min, and then mPEG-O-tosylate of molecular mass 20 kilodalton (Ts; 1.0 g, 0.05 mmol) was added in several portions over 2 hours. The mixture was stirred at room temperature for 5 days, and concentrated by rotary evaporation. The residue was diluted with water (30 mL), and stirred at room temperature for 2 hours to destroy any excess 20 kilodalton mPEG-O-tosylate. The solution was then neutralized with acetic acid, the pH adjusted to pH 5.0 and loaded onto a reverse phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 mL, hydroxide form; gradient of water to water/acetic acid—0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 453 mg (44%) of a white solid (1). Structural data for the compound were as follows: $^1$H-NMR (500 MHz; $D_2O$) δ 2.83 (t, 2H, O—C—C$\underline{H}_2$—S), 3.05 (q, 1H, S—C$\underline{H}$H—CHN), 3.18 (q, 1H, (q, 1H, S—C$\underline{H}$H—CHN), 3.38 (s, 3H, C$\underline{H}_3$O), 3.7 (t, OC$\underline{H}_2$C$\underline{H}_2$O), 3.95 (q, 1H, C$\underline{H}$N). The purity of the product was confirmed by SDS PAGE.

1.2 Synthesis of (2)

Triethylamine (~0.5 mL) was added dropwise to a solution of 1 (440 mg, 22 μmol) dissolved in anhydrous $CH_2Cl_2$ (30 mL) until the solution was basic. A solution of 20 kilodalton mPEG-O-p-nitrophenyl carbonate (660 mg, 33 μmol) and N-hydroxysuccinimide (3.6 mg, 30.8 μmol) in $CH_2Cl_2$ (20 mL) was added in several portions over 1 h at room temperature. The reaction mixture was stirred at room temperature for 24 h. The solvent was then removed by rotary evaporation, the residue was dissolved in water (100 mL), and the pH adjusted to 9.5 with 1.0 N NaOH. The basic solution was stirred at room temperature for 2 h and was then neutralized with acetic acid to a pH 7.0. The solution was then loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 mL, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 575 mg (70%) of a white solid (2). Structural data for the compound were as follows: $^1$H-NMR (500 MHz; $D_2O$) δ 2.83 (t, 2H, O—C—C$\underline{H}_2$—S), 2.95 (t, 2H, O—C—C$\underline{H}_2$—S), 3.12 (q, 1H, S—C$\underline{H}$H—CHN), 3.39 (s, 3H C$\underline{H}_3$O), 3.71 (t, OC$\underline{H}_2$C$\underline{H}_2$O). The purity of the product was confirmed by SDS PAGE.

Example 2

GlycoPEGylation of Factor IX Produced in CHO Cells

This example sets forth the preparation of asialoFactor IX and its sialylation with CMP-sialic acid-PEG.

2.1 Desialylation of rFactor IX

A recombinant form of Coagulation Factor IX (rFactor IX) was made in CHO cells. 6000 IU of rFactor IX were dissolved in a total of 12 mL USP $H_2O$. This solution was transferred to a CENTRICON® Plus 20, PL-10 centrifugal filter with another 6 mL USP $H_2O$. The solution was concentrated to 2 mL and then diluted with 15 mL 50 mM Tris-HCl pH 7.4, 0.15 M NaCl, 5 mM $CaCl_2$, 0.05% $NaN_3$ and then reconcentrated. The dilution/concentration was repeated 4 times to effectively change the buffer to a final volume of 3.0 mL. Of this solution, 2.9 mL (about 29 mg of rFactor IX) was transferred to a small plastic tube and to it was added 530 mU α2-3,6,8-Neuraminidase-agarose conjugate (*Vibrio cholerae*, Calbiochem, 450 μL). The reaction mixture was rotated gently for 26.5 hours at 32° C. The mixture was centrifuged 2 minutes at 10,000 rpm and the supernatant was collected. The agarose beads (containing neuraminidase) were washed 6 times with 0.5 mL 50 mM Tris-HCl pH 7.12, 1 M NaCl, 0.05% $NaN_3$. The pooled washings and supernatants were centrifuged again for 2 minutes at 10,000 rpm to remove any residual agarose resin. The pooled, desialylated protein solution was diluted to 19 mL with the same buffer and concentrated down to ~2 mL in a CENTRICON® Plus 20 PL-10 centrifugal filter. The solution was twice diluted with 15 mL of 50 mM Tris-HCl pH 7.4, 0.15 M NaCl, 0.05% $NaN_3$ and reconcentrated to 2 mL. The final desialyated rFactor IX solution was diluted to 3 mL final volume (~10 mg/mL) with the Tris Buffer. Native and desialylated rFactor IX samples were analyzed by IEF-Electrophoresis. Isoelectric Focusing Gels (pH 3-7) were run using 1.5 μL (15 μg) samples first diluted with 10 μL Tris buffer and mixed with 12 μL sample loading buffer. Gels were loaded, run and fixed using standard procedures. Gels were stained with Colloidal Blue Stain (FIG. 154), showing a band for desialylated Factor IX.

Example 3

Preparation of PEG (1 kDa and 10 kDa)-SA-Factor IX

Desialylated rFactor-IX (29 mg, 3 mL) was divided into two 1.5 mL (14.5 mg) samples in two 15 mL centrifuge tubes. Each solution was diluted with 12.67 mL 50 mM Tris-HCl pH 7.4, 0.15 M NaCl, 0.05% $NaN_3$ and either CMP-SA-PEG-1k or 10k (7.25 μmol) was added. The tubes were inverted gently to mix and 2.9 U ST3Gal3 (326 μL) was added (total volume 14.5 mL). The tubes were inverted again and rotated gently for 65 hours at 32° C. The reactions were stopped by freezing at −20° C. 10 μg samples of the reactions were analyzed by SDS-PAGE. The PEGylated proteins were purified on a Toso Haas Biosep G3000SW (21.5×30 cm, 13 um) HPLC column with Dulbecco's Phosphate Buffered Saline, pH 7.1 (Gibco), 6 mL/min. The reaction and purification were monitored using SDS Page and IEF gels. Novex Tris-Glycine 4-20% 1 mm gels were loaded with 10 μL (10 μg) of samples after dilution with 2 μL of 50 mM Tris-HCl, pH 7.4, 150 mM NaCl, 0.05% $NaN_3$ buffer and mixing with 12 μL sample loading buffer and 1 μL 0.5 M DTT and heated for 6 minutes at 85° C. Gels were stained with Colloidal Blue Stain (FIG. 155) showing a band for PEG (1 kDa and 10 kDa)-SA-Factor IX.

Example 4

Direct Sialyl-GlycoPEGylation of Factor IX

This example sets forth the preparation of sialyl-PEGylation of Factor IX without prior sialidase treatment.

4.1 Sialyl-PEGylation of Factor-IX with CMP-SA-PEG-(10 KDa)

Factor IX (1100 IU), which was expressed in CHO cells and was fully sialylated, was dissolved in 5 mL of 20 mM histidine, 520 mM glycine, 2% sucrose, 0.05% $NaN_3$ and 0.01% polysorbate 80, pH 5.0. The CMP-SA-PEG-(10 kDa) (27 mg, 2.5 μmol) was then dissolved in the solution and 1 U of ST3Gal3 was added. The reaction was complete after gently mixing for 28 hours at 32° C. The reaction was analyzed by SDS-PAGE as described by Invitrogen. The product protein was purified on an Amersham Superdex 200 (10×300 mm, 13 μm) HPLC column with phosphate buffered saline, pH 7.0 (PBS), 1 mL/min. $R_t$=9.5 min.

Example 5

Sialyl-PEGylation of Factor-IX with CMP-SA-PEG-(20 kDa)

Factor IX (1100 IU), which was expressed in CHO cells and was fully sialylated, was dissolved in 5 mL of 20 mM histidine, 520 mM glycine, 2% sucrose, 0.05% $NaN_3$ and 0.01% polysorbate 80, pH 5.0. The CMP-SA-PEG-(20 kDa) (50 mg, 2.3 µmol) was then dissolved in the solution and CST-II was added. The reaction mixture was complete after gently mixing for 42 hours at 32° C. The reaction was analyzed by SDS-PAGE as described by Invitrogen.

The product protein was purified on an Amersham Superdex 200 (10×300 mm, 13 µm) HPLC column with phosphate buffered saline, pH 7.0 (Fisher), 1 mL/min. $R_t$=8.6 min.

Example 6

Sialic Acid Capping of GlycoPEGylated Factor IX

This examples sets forth the procedure for sialic acid capping of sialyl-glycoPEGylated Factor IX.

6.1 Sialic Acid Capping of N-Linked and O-Linked Glycans of Factor-IX-SA-PEG (10 kDa)

Purified r-Factor-IX-PEG (10 kDa) (2.4 mg) was concentrated in a CENTRICON® Plus 20 PL-10 (Millipore Corp., Bedford, Mass.) centrifugal filter and the buffer was changed to 50 mM Tris-HCl pH 7.2, 0.15 M NaCl, 0.05% $NaN_3$ to a final volume of 1.85 mL. The protein solution was diluted with 372 µL of the same Tris buffer and 7.4 mg CMP-SA (12 µmol) was added as a solid. The solution was inverted gently to mix and 0.1 U ST3Gal1 and 0.1 U ST3Gal3 were added. The reaction mixture was rotated gently for 42 h at 32° C.

A 10 ng sample of the reaction was analyzed by SDS-PAGE. Novex Tris-Glycine 4-12% 1 mm gels were performed and stained using Colloidal Blue as described by Invitrogen. Briefly, samples, 10 µL (10 ng), were mixed with 12 µL sample loading buffer and 1 µL 0.5 M DTT and heated for 6 minutes at 85° C.

Example 7

Glycopegylated Factor IX Pharmacokinetic Study

Four glycoPEGylated FIX variants (PEG-9 variants) were tested in a PK study in normal mice. The activity of the four compounds had previously been established in vitro by clot, endogenous thrombin potential (ETP), and thromboelastograph (TEG) assays. The activity results are summarized in Table I.

TABLE I

| Compound | Clot activity (% of plasma) | ETP (relative specific activity) | TEG (relative specific activity) |
|---|---|---|---|
| rhFIX | 45% | 1.0 | 1.0 |
| PEG-9-2K (LS) | 27% | 0.3 | 0.2 |
| PEG-9-2K (HS) | 20% | 0.2 | 0.1 |
| PEG-9-10K | 11% | 0.6 | 0.3 |
| PEG-9-30K | 14% | 0.9 | 0.4 |

To assess the prolongation of activity of the four PEG-9 compounds in circulation, a PK study was designed and performed. Non-hemophilic mice were used, 2 animal per time point, 3 samples per animal. Sampling time points were 0, 0.08, 0.17, 0.33, 1, 3, 5, 8, 16, 24, 30, 48, 64, 72, and 96 h post compound administration. Blood samples were centrifuged and stored in two aliquots; one for clot analysis and one for ELISA. Due to material restrictions, the PEG-9 compounds were dosed in different amounts: rhFIX 250 U/kg; 2K(low substitution: "LS" (1-2 PEG substitutions per peptide molecule) 200 U/kg; 2K(high substitution: "HS" (3-4 PEG substitutions per peptide molecule) 200 U/kg; 10K 100 U/kg; 30K 100 U/kg. All doses were based on measured clotting assay units.

The results are outlined in Table II.

TABLE II

| Compound | Dose (U/kg) | Cmax (U/mL) | AUC (h-U/mL) | CL (mL/h/kg) |
|---|---|---|---|---|
| rhFIX | 250 | 0.745 | 1.34 | 187 |
| PEG-9-2K (LS) | 200 | 0.953 | 4.69 | 42.7 |
| PEG-9-2K (HS) | 200 | 0.960 | 9.05 | 22.1 |
| PEG-9-10K | 100 | 0.350 | 2.80 | 35.7 |
| PEG-9-30K | 100 | 1.40 | 8.83 | 11.3 |

The results demonstrate a trend towards prolongation for all the PEG-9 compounds. The values of AUC and $C_{max}$ were not compared directly. However, clearance (CL) was compared and CL is lower for the PEG-9 compounds compared to rhFIX, indicating a longer residence time in the mice. The time for the last detectable clot activity is increased for the PEG-9 compounds compared to rhFIX, even though rhFIX was administered at the highest dose.

Example 8

Preparation of LS and HS GlycoPEGylated Factor IX

GlycoPEGylated Factor IX with a low degree of substitution with PEG were prepared from native Factor IX by an exchange reaction catalyzed by ST3Gal-III. The reactions were performed in a buffer of 10 mM histidine, 260 mM glycine, 1% sucrose and 0.02% Tween 80, pH 7.2. For PEGylation with CMPSA-PEG (2 kD and 10 kD), Factor IX (0.5 mg/mL) was incubated with ST3GalIII (50 mU/mL) and CMP-SA-PEG (0.5 mM) for 16 h at 32° C. For PEGylation with CMP-SA-PEG 30 kD, the concentration of Factor IX was increased to 1.0 mg/mL, and the concentration of CMP-SA-PEG was decreased to 0.17 mM. Under these conditions, more than 90% of the Factor IX molecules were substituted with at least one PEG moiety.

GlycoPEGylated Factor IX with a high degree of substitution with PEG was prepared by enzymatic desialylation of native Factor IX. The Factor IX peptide was buffer exchanged into 50 mM mES, pH 6.0, using a PD10 column, adjusted to a concentration of 0.66 mg/mL and treated with AUS sialidase (5 mU/mL) for 16 h at 32° C. Desialylation was verified by SDS-PAGE, HPLC and MALDI glycan analysis. Asialo Factor IX was purified on Q Sepharose FF to remove the sialidase. The $CaCl_2$ fraction was concentrated using an Ultra15 concentrator and buffer exchanged into MES, pH 6.0 using a PD10 column.

2 kD and 10 kD PEGylation of asialo-Factor IX (0.5 mg/mL) was carried out by incubation with ST3Gal-III (50 mU/mL) and CMP-SA-PEG (0.5 mM) at 32° C. for 16 h. For PEGylation with CMPSA-PEG-30 kD, the concentration of Factor IX was increased to 1.0 mg/mL and the concentration of CMP-SA-PEG was decreased to 0.17 mM. After 16 h of PEGylation, glycans with terminal galactose were capped with sialic acid by adding 1 mM CMP-SA and continuing the incubation for an additional 8 h at 32° C. Under these conditions, more than 90% of the Factor IX molecules were substituted with at least one PEG moiety. Factor IX produced by this method has a higher apparent molecular weight in SDS-PAGE.

Example 9

Preparation of O-GlycoPEGylated Factor IX

O-glycan chains were introduced de novo into native Factor IX (1 mg/mL) by incubation of the peptide with GalNAcT-II (25 mU/mL) and 1 mM UDP-GalNAc at 32° C. After 4 h of incubation, the PEGylation reaction was initiated by adding CMPSA-PEG (2 Kd or 10 Kd at 0.5 mM or 30 kDd at 0.17 mM) and ST6GalNAc-I (25 mU/mL) and incubating for an additional 20 h.

Example 10 aPTT Assay of Compound a (PEG 30K FIX), Compound B (PEG 2K FIX), and FIX (rhFIX) in FIX-Deficient Knockout Mice 10.1 Materials and Methods All mice used in the experiment were FIX knockout mice (Lin et al., Blood 1997), crossed into a C57B1/6 strain background. Mice were aged 9-19 weeks at the time of the pharmacokinetic study. Both male and female mice were studied. Mice were distributed between groups to give a mean weight for each group which was similar and to give a distribution of weights in each of the groups. Additional mice were maintained for regular phlebotomy to provide FIX deficient serum for dilution of samples and standards.

Test animals were anesthetized with Avertin or Domitor. Right and left neck was shaved, and prepared in a sterile fashion. A small incision was made in the right neck to expose the external jugular vein. Factor IX was delivered (150 U/kg) in a total volume of approximately 100-120 microliters. The needle was withdrawn and gelfoam/surgifoam was applied with pressure to supplement local hemostasis. The neck incision was sutured closed. The mouse was placed under a warming lamp and whole blood was collected into 9 volumes:1 volume sodium citrate at the following times: prebleed (24 h or 48 h pre-dosing or 72 h post); 15 min; 1 h; 4 h; 24 h; 48 h; 72 h (for cross-over groups or in place of prebleed). Plasma from each aliquot was used for aPTT analysis using a Start 4 Coagulation Analyzer and Dapttin Tc-reagent.

Compound A was a FIX glycoPEGylated with sialic acid branched PEG (30 kD) based on cysteine bearing a PEG at the S atom and a PEG at NH. Compound B was a FIX glycoPEGylated with a sialic acid linear PEG (2 kD) glycine construct with PEG at the NH moiety.

10.2 Results

| Pre | 24 hours (Mean; range) | 48 hours (M/R) | 72 hours (M/R) |
|---|---|---|---|
| Factor IX (n = 12) | | | |
| <1% | 7.5% (2-16%) | 3.0% (1.2-4.1%) | 1.6% (<1-2.5%) |
| Compound A (n = 9) | | | |
| <1% | 187% (95-200%) | 140% (79-200%) | 77% (36-118%) |
| Compound B (n = 11) | | | |
| <1% | 62% (39-89%) | 24% (9-40%) | 10.1% (6-19%) |

The terminal phase half-life of conjugated and unconjugated FIX in these mice was determined by plotting the average values at each timepoint (60 minutes, 24 hour, 48 hour, 72 hour for terminal phase), generating the linear curve of the fall-off, and then using the slope of that line in the following formula:

$$T_{1/2}=\log_e(2)/b_2$$

Where $b_2$ is the slope. (Ewenstein, et al. *Transfusion* 2002). The unconjugated FIX $T_{1/2}$ in the mice was 12.8 hours.

The values for the unconjugated FIX samples were determined from undiluted (1:1) samples, because all values fell within the linear range for the aPTT standard. The 15 minutes sample was actually run at 1:1 and 1:2, and each gave a consistent result of 74% at 15 minutes. The dose of 150 U/kg would give an expected recovery after dosing of plasma-derived FIX to a human of 150%. Unconjugated FIX is known to have a decreased recovery (~55-80% of expected) when compared to PD FIX in humans. This could be even lower in mice, accounting for the FIX recovery of about 50% of expected seen in these animals (74% observed/150% expected).

Determination of the values for Neose A samples had to account for the unexpectedly high initial values, which rose above the top standard (200%) even when diluted 1:2 and 1:4. The recoversie in the first hour appear to be in the 700-800% range, which is to about 500% of the expected recovery after a dose of 150 U/kg. The terminal half-life is 23 hours, calculated as above.

The values for the Neose B samples were in the range of 325-350% in the first hour after injection, indicating a recovery of >200% of expected. The terminal phase $T_{1/2}$ was 14.4 hours.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A PEGylated Factor IX protein comprising SEQ ID NO:1 and a poly(ethylene glycol) moiety, wherein the poly(ethylene glycol) moiety is conjugated to an amino acid selected from Asn 157 and Asn 167 of SEQ ID NO:1 via a glycosyl linking group of a glycosyl residue, and having a composition according to the formula:

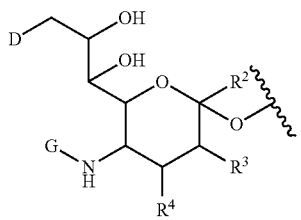

wherein
$R^2$ is COOH;
$R^3$ is H;
$R^4$ is OH;
D is OH; and
G is $R^1$-L-
   wherein
   L is C(O)CH$_2$NHC(O); and
   $R^1$ is the poly(ethylene glycol) moiety, wherein the poly(ethylene glycol) moiety comprises a branched poly(ethylene glycol) having a core glycerol moiety, and wherein the branched poly(ethylene glycol) has a molecular weight of about 40 kDa.

2. A pharmaceutical formulation comprising the Factor IX conjugate of claim 1 and a pharmaceutically acceptable carrier.

3. A method of stimulating blood coagulation in a mammal, said method comprising administering to said mammal the PEGylated Factor IX conjugate of claim 1.

4. A method of treating hemophilia in a subject, said method comprising administering to said subject said Factor IX conjugate of claim 1.

5. The method of treating hemophilia of claim 4, wherein hemophilia is hemophilia B.

6. A Factor IX conjugate comprising a Factor IX protein comprising SEQ ID NO:1 and a poly(ethylene glycol) (PEG) moiety, wherein the PEG moiety is conjugated to an amino acid of SEQ ID NO:1 via a glycosyl linking group of a glycosyl residue, and having a composition according to the formula:

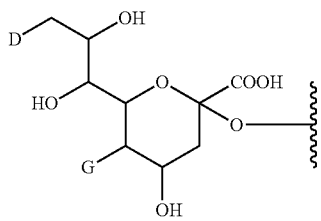

wherein
D is OH; and
G has the formula

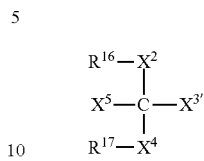

wherein
$X^2$ is CH$_2$,
$X^{3'}$ is CH$_2$OC(O)NHCH$_2$C(O)NH,
$X^4$ is a bond,
$X^5$ is H, and
$R^{16}$ and $R^{17}$ are poly(ethylene) gycol, that compose a branched PEG moiety.

7. The Factor IX conjugate of claim 6, wherein the PEG moiety is conjugated to an amino acid of SEQ ID NO:1 selected from the group consisting of Asn157 and Asn167 1 via a glycosyl linking group of a glycosyl residue.

8. The Factor IX conjugate of claim 7, wherein the PEG moiety is conjugated to amino acids Asn 157 and Asn167 of SEQ ID NO:11 via a glycosyl linking group of a glycosyl residue.

9. The Factor IX conjugate of claim 6, wherein the branched PEG moiety has a molecular weight of about 40 kD.

10. A pharmaceutical formulation comprising the Factor IX conjugate of claim 6 and a pharmaceutically acceptable carrier.

11. A method of stimulating blood coagulation in a mammal, said method comprising administering to said mammal the Factor IX conjugate of claim 6.

12. A method of treating hemophilia in a subject, said method comprising administering to said subject said Factor IX conjugate of claim 6.

13. The method of treating hemophilia of claim 12, wherein hemophilia is hemophilia B.

14. A Factor IX conjugate comprising a Factor IX protein comprising SEQ ID NO:1 and a poly(ethylene glycol) (PEG) moiety, wherein the PEG moiety is conjugated to an amino acid selected from Asn 157 and Asn 167 of SEQ ID NO:1 via a glycosyl linking group of a glycosyl residue, and having a composition according to the formula:

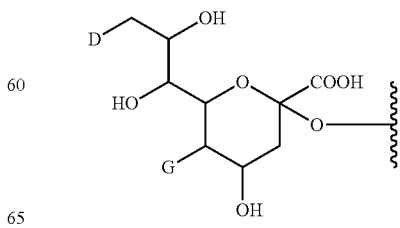

wherein
  D is OH; and
  G is a composition according to the formula

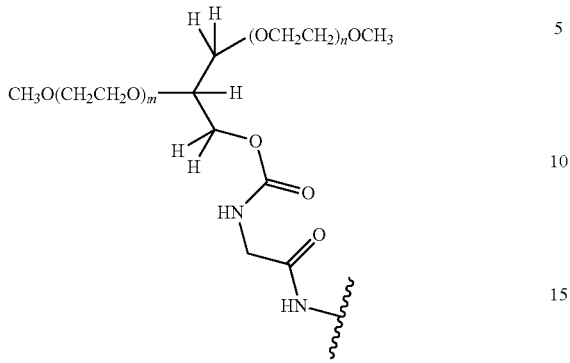

wherein m and n are integers independently selected from 1 to 2500.

15. The Factor IX conjugate of claim 14, wherein the PEG moiety has a molecular weight of about 40 kD.

16. A pharmaceutical formulation comprising the Factor IX conjugate of claim 14 and a pharmaceutically acceptable carrier.

17. A method of stimulating blood coagulation in a mammal, said method comprising administering to said mammal said Factor IX conjugate of claim 14.

18. A method of treating hemophilia in a subject, said method comprising administering to said subject said Factor IX conjugate of claim 14.

19. A Factor IX conjugate comprises a glycosyl residue having the formula:

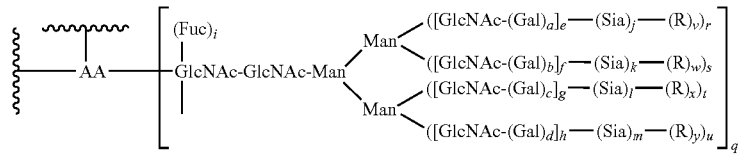

wherein a, b, c, d, i, r, s, t, and u are integers independently selected from 0 and 1;

q is 1;

e, f, g, and h are members independently selected from the integers from 0 to 6;

j, k, l, and m are members independently selected from the integers from 0 and 100;

v, w, x, and y are independently selected from 0 and 1, and at least one of v, w, x, and y is 1;

AA is an amino acid residue of said Factor IX peptide selected from the group consisting of Asn 157, Asn 167 and combinations thereof;

Sia-(R) has the formula:

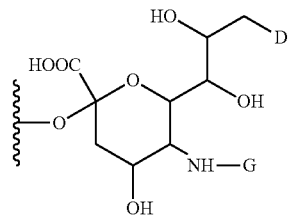

wherein
  D is —OH; and
  G is $R^1$-L-
    wherein
      L is $C(O)CH_2NHC(O)$; and
      $R^1$ is the poly(ethylene glycol) moiety, wherein the poly(ethylene glycol) moiety comprises a branched poly(ethylene glycol) having a core glycerol moiety, and wherein the branched poly(ethylene glycol) has a molecular weight of about 40 kDa.

20. A Factor IX conjugate of claim 19, wherein j, k, l, and m are 1, and e, f, g, and h are 3 or less.

* * * * *